US009278070B2

(12) United States Patent
Coulter et al.

(10) Patent No.: US 9,278,070 B2
(45) Date of Patent: Mar. 8, 2016

(54) COMPOSITION COMPRISING OIL DROPS

(75) Inventors: Ivan Coulter, Dublin (IE); Bernard Francis McDonald, Castleblayney (IE); Vincenzo Aversa, Dublin (IE)

(73) Assignee: Sigmoid Pharma Limited, Dublin (IE)

( * ) Notice: Subject to any disclaimer, the term of this patent is extended or adjusted under 35 U.S.C. 154(b) by 176 days.

(21) Appl. No.: 13/321,149

(22) PCT Filed: May 18, 2010

(86) PCT No.: PCT/EP2010/056838
§ 371 (c)(1),
(2), (4) Date: Feb. 9, 2012

(87) PCT Pub. No.: WO2010/133609
PCT Pub. Date: Nov. 25, 2010

(65) Prior Publication Data
US 2012/0141531 A1 Jun. 7, 2012

Related U.S. Application Data

(60) Provisional application No. 61/179,121, filed on May 18, 2009.

(30) Foreign Application Priority Data

May 18, 2009 (IE) .................................... 2009/0381

(51) Int. Cl.
| | | |
|---|---|---|
| *A61K 9/10* | (2006.01) | |
| *A61K 9/113* | (2006.01) | |
| *A61K 9/48* | (2006.01) | |
| *A61K 38/13* | (2006.01) | |
| *A61K 9/16* | (2006.01) | |
| *A61K 9/107* | (2006.01) | |
| *A61K 9/50* | (2006.01) | |
| *A61K 31/436* | (2006.01) | |
| *A61K 47/10* | (2006.01) | |
| *A61K 47/14* | (2006.01) | |
| *A61K 47/44* | (2006.01) | |
| *A61K 38/00* | (2006.01) | |

(52) U.S. Cl.
CPC ............... *A61K 9/1658* (2013.01); *A61K 9/107* (2013.01); *A61K 9/1617* (2013.01); *A61K 9/1635* (2013.01); *A61K 9/1652* (2013.01); *A61K 9/1694* (2013.01); *A61K 9/5026* (2013.01); *A61K 9/5036* (2013.01); *A61K 9/5047* (2013.01); *A61K 9/5073* (2013.01); *A61K 31/436* (2013.01); *A61K 47/10* (2013.01); *A61K 47/14* (2013.01); *A61K 47/44* (2013.01); *A61K 9/1075* (2013.01); *A61K 38/00* (2013.01)

(58) Field of Classification Search
CPC ............ A61K 9/4858; A61K 2300/00; A61K 9/1075; A61K 38/13; A61K 47/44; A61K 47/10; A61K 9/4866; A61K 9/161; A61K 9/4808; A61K 47/14; A61K 31/00; A61K 9/107
USPC ........ 514/20.5, 937, 938, 786, 939, 942, 962, 514/970; 424/400, 455, 451, 456, 484
See application file for complete search history.

(56) References Cited

U.S. PATENT DOCUMENTS

| | | |
|---|---|---|
| 4,279,632 A | 7/1981 | Frosch et al. |
| 4,379,454 A | 4/1983 | Campbell et al. |
| 4,388,307 A | 6/1983 | Cavanak |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |

(Continued)

FOREIGN PATENT DOCUMENTS

| | | |
|---|---|---|
| AU | 1977031116 | 12/1976 |
| AU | 627220 B2 | 8/1992 |

(Continued)

OTHER PUBLICATIONS

Madene et al. 2006. Flavour encapsulation and controlled release—a review; International Journal of Food Science and Technology 41:1-21.*

(Continued)

*Primary Examiner* — Gary Nickol
*Assistant Examiner* — Mary Lyons
(74) *Attorney, Agent, or Firm* — Klarquist Sparkman, LLP

(57) ABSTRACT

A composition comprises a water-soluble polymer matrix in which are dispersed droplets of oil, the composition comprising an active principle. The invention includes embodiments in which the active principle is included in at least some of the oil droplets as well as embodiments in which the oil droplets are free of active principle. The oil droplets are released as the matrix containing them dissolves in an aqueous medium. In one embodiment, the oil droplets are substantially immobilized in or by the matrix and the immobilizing feature is lost as the matrix dissolves in aqueous media. In certain embodiments, the oil drops may collectively be referred to as the oil phase of the composition of the invention. The product may be in the form of mini-beads. The oil phase and/or the polymer matrix may each include a surfactant.

18 Claims, No Drawings

(56) References Cited

U.S. PATENT DOCUMENTS

| | | | |
|---|---|---|---|
| 4,749,574 | A | 6/1988 | Ueda et al. |
| 4,751,241 | A | 6/1988 | Motoyama et al. |
| 4,857,335 | A | 8/1989 | Bohm |
| 5,102,668 | A | 4/1992 | Eichel et al. |
| 5,145,684 | A | 9/1992 | Liversidge et al. |
| 5,330,835 | A | 7/1994 | Kikuchi et al. |
| 5,342,625 | A | 8/1994 | Hauer et al. |
| 5,362,564 | A | 11/1994 | Suzuki et al. |
| 5,385,737 | A | 1/1995 | Shigeno et al. |
| 5,411,952 | A | 5/1995 | Kaswan |
| 5,418,010 | A | 5/1995 | Janda et al. |
| 5,478,508 | A | 12/1995 | Suzuki et al. |
| 5,480,655 | A | 1/1996 | Jizomoto et al. |
| 5,492,701 | A | 2/1996 | Cervos et al. |
| 5,500,224 | A | 3/1996 | Vranckx et al. |
| 5,510,118 | A | 4/1996 | Bosch et al. |
| 5,529,777 | A | 6/1996 | Andrianov et al. |
| 5,529,783 | A | 6/1996 | Burke et al. |
| 5,571,533 | A | 11/1996 | Santus et al. |
| 5,645,856 | A | 7/1997 | Lacy et al. |
| 5,650,232 | A | 7/1997 | Glenn et al. |
| 5,665,386 | A | 9/1997 | Benet et al. |
| 5,674,495 | A | 10/1997 | Bowersock et al. |
| 5,795,590 | A | 8/1998 | Kiefer et al. |
| 5,827,531 | A | 10/1998 | Morrison et al. |
| 5,843,347 | A | 12/1998 | Nguyen et al. |
| 5,851,275 | A | 12/1998 | Amidon et al. |
| 5,858,401 | A | 1/1999 | Bhalani et al. |
| 5,871,774 | A | 2/1999 | Lemelson |
| 5,882,680 | A | 3/1999 | Suzuki et al. |
| 5,958,876 | A | 9/1999 | Woo et al. |
| 5,961,970 | A | 10/1999 | Lowell et al. |
| 6,022,562 | A | 2/2000 | Autant et al. |
| 6,113,936 | A | 9/2000 | Takebayashi et al. |
| 6,146,663 | A | 11/2000 | Bissery et al. |
| 6,174,466 | B1 | 1/2001 | Kiefer et al. |
| 6,190,692 | B1 | 2/2001 | Busetti et al. |
| 6,251,661 | B1 | 6/2001 | Urabe et al. |
| 6,267,985 | B1 | 7/2001 | Chen et al. |
| 6,284,271 | B1 | 9/2001 | Lundberg et al. |
| 6,309,663 | B1 | 10/2001 | Patel et al. |
| 6,361,298 | B1 | 3/2002 | Kiefer et al. |
| 6,429,089 | B1 | 8/2002 | Matsuki |
| 6,457,339 | B2 | 10/2002 | Komura |
| 6,531,150 | B1 | 3/2003 | Sunohara et al. |
| 6,569,463 | B2 | 5/2003 | Patel et al. |
| 6,585,997 | B2 | 7/2003 | Moro et al. |
| 6,761,903 | B2 | 7/2004 | Chen et al. |
| 6,923,988 | B2 | 8/2005 | Patel et al. |
| 6,972,132 | B1 | 12/2005 | Kudo et al. |
| 7,097,857 | B2 | 8/2006 | Tracy et al. |
| 7,267,813 | B2 | 9/2007 | Watanabe et al. |
| 7,374,779 | B2 | 5/2008 | Chen et al. |
| 7,727,551 | B2 | 6/2010 | Massironi |
| 2001/0003589 | A1 | 6/2001 | Neuer et al. |
| 2001/0024658 | A1 | 9/2001 | Chen et al. |
| 2002/0009457 | A1 | 1/2002 | Bowersock et al. |
| 2002/0098242 | A1 | 7/2002 | Darder |
| 2003/0045516 | A1 | 3/2003 | Luly et al. |
| 2003/0078194 | A1 | 4/2003 | Cho et al. |
| 2003/0104048 | A1 | 6/2003 | Patel et al. |
| 2003/0124061 | A1 | 7/2003 | Roberts |
| 2003/0180352 | A1 | 9/2003 | Patel et al. |
| 2003/0193102 | A1 | 10/2003 | Yan |
| 2003/0232076 | A1 | 12/2003 | Makino et al. |
| 2003/0235595 | A1 | 12/2003 | Chen et al. |
| 2004/0029855 | A1 | 2/2004 | Klaveness et al. |
| 2004/0062802 | A1 | 4/2004 | Hermelin |
| 2004/0126428 | A1 | 7/2004 | Hughes et al. |
| 2004/0258701 | A1 | 12/2004 | Dominowski et al. |
| 2004/0258702 | A1 | 12/2004 | Blonder et al. |
| 2005/0037077 | A1 | 2/2005 | Legrand et al. |
| 2005/0095288 | A1 | 5/2005 | Honea |
| 2005/0249807 | A1 | 11/2005 | Brown et al. |
| 2006/0018965 | A1 | 1/2006 | Moodley et al. |
| 2006/0034937 | A1* | 2/2006 | Patel ............................ 424/497 |
| 2006/0135441 | A1 | 6/2006 | Khodadoust et al. |
| 2006/0222701 | A1 | 10/2006 | Kulkarni et al. |
| 2007/0154554 | A1 | 7/2007 | Burgermeister et al. |
| 2007/0292523 | A1 | 12/2007 | Moodley et al. |
| 2008/0020018 | A1 | 1/2008 | Moodley et al. |
| 2008/0107694 | A1 | 5/2008 | Trogden et al. |
| 2008/0113031 | A1* | 5/2008 | Moodley et al. ............. 424/490 |
| 2008/0124279 | A1 | 5/2008 | Andremont et al. |
| 2008/0311201 | A1 | 12/2008 | Der-Yang et al. |
| 2008/0317769 | A1 | 12/2008 | Kang et al. |
| 2008/0318912 | A1 | 12/2008 | Fox et al. |
| 2010/0136105 | A1 | 6/2010 | Chen et al. |
| 2010/0203120 | A1 | 8/2010 | Coulter |
| 2010/0215737 | A1 | 8/2010 | Coulter |
| 2010/0239665 | A1 | 9/2010 | Coulter |
| 2010/0255087 | A1 | 10/2010 | Coulter |
| 2010/0297221 | A1 | 11/2010 | Coulter |
| 2011/0052645 | A1 | 3/2011 | Coulter |

FOREIGN PATENT DOCUMENTS

| | | |
|---|---|---|
| CA | 2170748 | 3/1995 |
| CA | 2376261 | 6/2000 |
| CN | 1557283 | 12/2004 |
| DE | 19848849 | 10/1998 |
| EP | 0 348 910 A2 | 1/1990 |
| EP | 0396425 | 11/1990 |
| EP | 0525731 | 2/1993 |
| EP | 0550067 | 7/1993 |
| EP | 0621775 | 11/1994 |
| EP | 0650721 | 5/1995 |
| EP | 0760237 | 3/1997 |
| EP | 0778083 | 6/1997 |
| EP | 0922451 | 6/1999 |
| EP | 0813876 | 3/2002 |
| EP | 0789561 | 4/2004 |
| EP | 1811979 | 11/2008 |
| EP | 2105129 | 9/2009 |
| GB | 2257359 | 1/1993 |
| JP | A-58 013508 | 1/1983 |
| JP | A-58 077810 | 5/1983 |
| JP | 59-088420 | 5/1984 |
| JP | S61126016 A | 6/1986 |
| JP | A-61 151119 | 7/1986 |
| JP | 64-000015 | 1/1989 |
| JP | H0549899 A | 3/1993 |
| JP | H06254382 A | 9/1994 |
| JP | 7247215 A | 9/1995 |
| JP | 2000-247911 | 9/2000 |
| JP | 2000-302654 | 10/2000 |
| JP | 2004-43332 A | 2/2004 |
| JP | 2005-500336 | 1/2005 |
| JP | 2008-512371 | 4/2008 |
| JP | 64 000015 | 8/2010 |
| WO | WO 91/06282 | 5/1991 |
| WO | WO 93/00063 | 1/1993 |
| WO | WO 93/13753 | 7/1993 |
| WO | WO 94/15636 | 7/1994 |
| WO | WO 96/36322 | 11/1996 |
| WO | WO 97/02017 | 1/1997 |
| WO | WO 97/02042 | 1/1997 |
| WO | WO 98/18610 | 5/1998 |
| WO | WO 98/50018 | 11/1998 |
| WO | WO 98/50033 | 11/1998 |
| WO | WO 99/06024 | 2/1999 |
| WO | WO 99/13914 | 3/1999 |
| WO | WO 00/00179 | 1/2000 |
| WO | WO 00/33862 | 6/2000 |
| WO | WO 00/69420 | 11/2000 |
| WO | WO 01/08666 | 2/2001 |
| WO | WO 01/32142 | 5/2001 |
| WO | WO 01/37808 | 5/2001 |
| WO | WO 01/51008 | 7/2001 |
| WO | WO 02/064162 | 8/2002 |
| WO | WO 03/009812 | 2/2003 |
| WO | WO 03/018134 | 3/2003 |
| WO | WO 03/020243 | 3/2003 |
| WO | WO 03/053404 | 7/2003 |

(56) References Cited

FOREIGN PATENT DOCUMENTS

| WO | WO 03/056938 | 7/2003 |
| --- | --- | --- |
| WO | WO 03/092741 | 11/2003 |
| WO | WO 2004/022220 | 3/2004 |
| WO | WO 2004/042024 | 5/2004 |
| WO | WO 2004/064997 | 8/2004 |
| WO | WO 2004/084870 | 10/2004 |
| WO | WO 2004/087204 A2 | 10/2004 |
| WO | WO 2004/108121 A1 | 12/2004 |
| WO | WO 2005/020993 | 3/2005 |
| WO | WO 2005/020994 | 3/2005 |
| WO | WO 2005/030205 | 4/2005 |
| WO | WO 2005/048998 | 6/2005 |
| WO | WO 2005/072088 | 8/2005 |
| WO | WO 2005/074913 | 8/2005 |
| WO | WO 2005/100454 | 10/2005 |
| WO | WO 2005/107721 | 11/2005 |
| WO | WO 2006/026592 | 3/2006 |
| WO | WO 2006/027685 | 3/2006 |
| WO | WO 2006/035416 | 4/2006 |
| WO | WO 2006/110802 | 10/2006 |
| WO | WO 2007/007946 A1 | 1/2007 |
| WO | WO 2007/012478 | 2/2007 |
| WO | WO 2007/014445 | 2/2007 |
| WO | WO 2007/018943 | 2/2007 |
| WO | WO 2007/095092 | 8/2007 |
| WO | WO 2008/122967 | 10/2008 |
| WO | WO 2009/002533 | 12/2008 |
| WO | WO 2009/014774 | 1/2009 |
| WO | WO 2009/060305 | 5/2009 |
| WO | WO 2010/005980 | 1/2010 |
| WO | WO 2010/043630 | 4/2010 |

OTHER PUBLICATIONS

Gao et al. 1998 (Physicochemical characterization and evaluation of a microemulsion system for oral delivery of cyclosporin A: Intern. J. or Pharm. 161: 75-86).*

Wakerly et al. 1996 (Pectin/Ethylcellulose Film Coating Formulations for Colonic Drug Delivery; Pharm Res 13(8):1210-12).*

Al-Meshal et al., "Oral administration of liposomes containing cyclosporine: a pharmacokinetic study," *International Journal of Pharmaceutics* 168:163-168, 1998.

Anderberg et al., "Sodium Caprate Elicits Dilatations in Human Intestinal Tight Junctions and Enhances Drug Absorption by the Paracellular Route," *Pharmaceutical Research* 10(6):857-864, 1993.

Barnes et al., "Theophylline: New Perspectives for an Old Drug," *AM J Respir Crit Care Med* 167:813-818, 2003.

Borel et al., "Carotenoids in biological emulsions: solubility, surface-to-core distribution, and release from lipid droplets," *Journal of Lipid Research* 37:250-261, 1996.

Cannon, "Oral Solid Dosage Forms of Lipid-based Drug Delivery Systems," *AM Pharm Rev* 8(1):108-115, 2005.

Chourasia et al., "Pharmaceutical approaches to colon targeted drug delivery systems," *J. Pharm. Pharmaceut. Sci.* 6(1):33-66-2003.

Chowdary et al., "Controlled Nifedipine Release from Microcapsules of its Dispersions in PVP-MCC and HPC-MCC," *Drug Development and Industrial Pharmacy* 21(10):1183-1192, 1995.

Drewe et al., "The absorption site of cyclosporine in the human gastro-intestinal tract," *Br. J. clin. Pharmac.* 33:39-43, 1992.

Gao et al., "Physiochemical characterization and evaluation of a microemulsion system for oral delivery of yclosporine A," *International Journal of Pharmaceutics* 161:75-86, 1998.

Gursoy et al., "Self-emulsifying drug delivery systems (SEDDS) for improved oral delivery of lipophilic drugs," *Biomedicine & Pharmacotherapy* 58:173-182, 2004.

Ikegawa et al., Inhibition of P-glycoprotein by flavonoid derivatives in Adriamycin-resistant human myelogenous leukemia (K562/ADM)cells, *Cancer Letters* 177:89-93, 2002.

Kim et al., "Once-a-Day Oral Dosing Regimen of Cyclosporin A: Combined Therapy of Cyclosporin A Premicroemulsion Concentrates and Enteric Coated Solid-State Premicroemulsion Concentrates," *Pharmaceutical Research* 18(4):454-459, 2001.

Liu et al., "Gelatin-Stabilised Microemulsion-Based Organogels Facilitates Percutaneous Penetration of Cyclosporin A In Vitro and Dermal Pharmacokinetics In Vivo," *Journal of Pharmaceutical Sciences* 96(11):3000-3009, Nov. 2007.

Manakova et al., "Failure of FK506 (tacrolimus) to alleviate apomorphine-induced circling in rat Parkinson model in spite of some cytoprotective effects in SH-SY5Y dopaminergic cells," *Brain Research* 1038:83-91, 2005.

McGinity et al., Aqueous Polymeric Coatings for Pharmaceuticals Dosage Forms, Marcel Dekker, Inc., 1997.

Miller et al., "Controlled Trial of Nimodipine in Amyotrophic Lateral Sclerosis," *Neuromusc. Disord.*, 6(2):101-104, 1996.

Ribeiro et al., "Microencapsulation of lipophilic drugs in chitosan-coated alginate microspheres," *International Journal of Pharmaceutics* 187:115-123, 1999.

Strowig et al., Comparison of Insulin Monotherapy and Combination Therapy with Insulin and Metformin or Insulin and Troglitazone in Type 2 Diabetes, *Diabetes Care* 25(10):1691-1698, 2002.

Sweetman and Martindale, "Nimodipine," *Cardiovascular Drugs* p. 946, 2002.

Yang et al., "Transport and uptake characteristics of a new derivative of berberine (CPU-86017) by human intestinal epithelial cell line: Caco-2," *Acta Pharmacol Sin* 24(12):1185-1191, 2003.

Yeh et al., "Effect of Medium-Chain Glycerides on Physiological Properties of Rabbit Intestinal Epithelium in Vitro," *Pharmaceutical Research* 11(8):1148-1154, 1994.

Zhang et al., "P-glycoprotein restricted transport of nimodipine across blood-brain barrier," *Acta Pharmacol Sin* 24(9):903-906, 2003.

Zuber et al., "Reversible cerebral angiopathy," *J. Neurol* 253:1585-1588, 2006.

Final Office Action dated Jun. 17, 2011, from U.S. Appl. No. 11/663,834, filed Mar. 27, 2007.

Non-Final Office Action dated Jul. 15, 2011, from U.S. Appl. No. 11/236,549, filed Sep. 28, 2005.

Non-Final Office Action from U.S. Appl. No. 11/236,549 dated May 5, 2009.

Non-Final Office Action from U.S. Appl. No. 11/236,549 dated Oct. 6, 2010.

Final Office Action from U.S. Appl. No. 11/236,549 dated Apr. 1, 2011.

Non-Final Office Action from U.S. Appl. No. 11/663,834 dated Mar. 3, 2010.

Cannon, "Oral solid dosage forms of lipid-based drug delivery systems," *American Pharmaceutical Review* 8(1):108, Jan. 2005.

Liu et al., "Gelatin-stabilised microemulsion-based organogels facilitates percutaneous penetration of Cyclosporin A In Vitro and dermal pharmacokinetics In Vivo," *Journal of Pharmaceutical Sciences* 96:11:3000-3009, Nov. 2007.

International Search Report from International PCT Application No. PCT/EP2010/056838, dated Oct. 4, 2011.

Loufrani et al., "Vasodilator treatment with hydralazine increases blood flow in mdx mice resistance arteries without vascular wall remodeling or endothelium function improvement," *Journal of Hypertension* 23:1855-1860, 2005.

Milojevic et al., "Amylose as a coating for drug delivery to the colon: Preparation and in vitro evaluation using 5-aminosalicylic acid pellets," *Journal of Controlled Release* 38:75-84, 1996.

Murthy et al., "Treatment of Dextran Sulfate Sodium-Induced Murine Colitis by Intracolonic Cyclosporin," *Digestive Diseases and Sciences* 38(9):1722-1734, Sep. 1993.

Riviere et al., "Effects of Vasoactive Drugs on Transdermal Lidocaine Iontophoresis," *Journal of Pharmaceutical Sciences* 80(7):615-620, Jul. 1991.

NIMOTOP FDA approved labeling text, Dec. 2005.

Non-final Office action from U.S. Appl. No. 12/594,534, dated Mar. 30, 2012, 31pp.

Non-final Office action from U.S. Appl. No. 12/598,395, dated Mar. 26, 2012, 11pp.

Final Office action from U.S. Appl. No. 11/236,549, dated Mar. 15, 2012, 25pp.

(56) References Cited

OTHER PUBLICATIONS

Non-Final Office Action dated Apr. 23, 2012, from U.S. Appl. No. 12/594,553.
Non-Final Office Action dated Jun. 21, 2012, from corresponding U.S. Appl. No. 12/597,154.
Xu et al. "Structure Evolution of Gelatin Particles Induced by pH and Ionic Strength," *Microscopy Research and Technique*, 76:272-281, 2013.
Xu et al. "Effects of anionic surfactants on grafting density of gelatin modified with PDMS-E," *Colloids and Surfaces B: Biointerfaces*, 114:310-315, 2014.
Bowersock et al. "Oral vaccination with alginate microsphere systems," *Journal of Controlled Release*, 39: 209-230, 1996.
Florindo et al. "The enhancement of the immune response against *S. equi* antigens through the intranasal administration of poly-ε-caprolactone-based nanoparticles," *Biomaterials*, 30: 879-891, 2009.
Shioji, Yusaku "Manufacturing technology of solid formulation", CMC Publishing Co. Ltd., pp. 46-48 and 174-177, Jan. 27, 2003.
Office action issued for Japanese Patent Application No. 2006-507572.
Drug Bank, www.drugbank.ca/drugs/DB00244, 12 pages.
Ismailos et al., "Unusual solubility behaviour of cyclosporin A in aqueous media," *J. Pharm. Pharmacol.* 43:287-289, 1990.
McGinity et al., "Enteric Film Coating of Soft Gelatin Capsules," *Drug Development & Delivery* 3(6), Sep. 6, 2003.
Newman et al., "Use of Nonionic Block Copolymers in Vaccines and Therapeutics," *Critical Reviews™ in Therapeutic Drug Carrier Systems* 15(2): 89-142; 1998.
Qiu et al., "Developing Solid Oral Dosage Forms: Pharmaceutical Theory & Practice," *Academic Press* p. 445 only, 2009.
Reich, "Formulation and physical properties of soft capsules," *Chapter 11, Pharmaceutical Capsules*, $2^{nd}$ edition, Edited by Fridrun Podczeck and Brian E Jones, p. 208, 2004.
Westerink et al., "ProJuvant™ (Pluronic F127®/chitosan) enhances the immune response to intranasally administered tetanus toxoid," *Vaccine* 20:711-723; 2002.
Dhara et al., "Stability of Sodium Dodecyl Sulfate Micelles in the Presence of a Range of Water-Soluble Polymers: A Pressure-Jump Study," *J. Phys. Chem. B.*, 105:7133-7138; 2001.
Greener et al., "Interaction of Anionic Surfactants with Gelatin: Viscosity Effects," *Macromolecules*, 20: 2490-2498; 1987.
Holmberg et al., *Surfactants and Polymers in Aqueous Solution*. John Wiley & Sons, Ltd. 2002.
Muller et al. "Competitive Adssorption of Gelatin and Sodium Dodecylbenzenesulfonate at Hydrophobic Surfaces," *Langmuir*, 14: 3107-3114; 1998.
Wesley et al., "Structure of Polymer/Surfactant Complexes Formed by Poly(2-(dimethylamino)ethyl metharylate) and Sodium Dodecyl Sulfate," *Langmuir* 18: 5704-5707; 2002.
Holmgren et al. "Mucosal immunity and vaccines," *Nature Medicine Supplement.* 11(4): 545-553, Apr. 2005.
Sandborn et al. "The Pharmacokinetics and Colonic Tissue Concentrations of Cyclosporine After IV, Oral, and Enema Administration," *J. Clin. Pharmacol.* 31:76-80, 1991.
Rodriguez et al., "Colonic budesonide delivery from ph-dependent microcapsules containing lipidic cores," *Acta Technologiae et Legis Medicamenti* 11(1):45-52, 2000.
Non-Final Office Action from co-pending U.S. Appl. No. 12/594,542 dated Oct. 5, 2012.
Final Office Action from co-pending U.S. Appl. No. 12/594,553 dated Sep. 10, 2012.
Non-Final Office Action from co-pending U.S. Appl. No. 13/441,780 dated Nov. 28, 2012.

\* cited by examiner

COMPOSITION COMPRISING OIL DROPS

CROSS REFERENCE TO RELATED APPLICATIONS

This is the U.S. National Stage of International Application No. PCT/EP2010/056838, filed May 18, 2010, which was published in English under PCT Article 21(2), which in turn claims the benefit of U.S. Provisional Application No. 61/179,121, filed May 18, 2009, and Ireland Application No. 2009/0381, filed May 18, 2009. The U.S. provisional application and Ireland application are incorporated herein in their entirety.

This invention relates to compositions for delivering active principles, in particular active principles in a liquid state. The composition may be used for example in pharmaceuticals, cosmetics, healthcare, veterinary, aquaculture, fermentation, diagnostics, food clean-tech and environmental applications. The invention also relates to methods of making the compositions, methods of using them, and other subject matter.

BACKGROUND

For a variety of reasons, it is desirable in the fields of pharmaceuticals, cosmetics, food, clean-tech, photography and the environment to maintain, deliver and administer (or use) active principles in a fluid state. Fluid or solubilized active principles generally act faster (eg pass more quickly through or are more quickly absorbed by membranes especially natural membranes such as skin, mucous membranes or other cell membranes) than solid or dry forms of the active principle. For specific applications such as oral administration of food supplements and pharmaceuticals, it is desirable to formulate the active principles as solutions or liquids in order to increase and/or accelerate absorption or effect and/or to enhance the control and/or predictability of absorption or effect. However, fluids and liquids tend to be less stable e.g. to light and air and tend to require special containment for transport (eg vials, tankers) and for administration (eg syringes). Further processing of solids (eg applying additional layers or coats of other materials) is generally easier than further processing of liquids which at least require a filling step into a receptacle of predefined geometry such as, for example, liquid-filled soft-gel capsules, used in the food supplements and pharmaceuticals industries, which are essentially limited in size in part by the machinery required to achieve the filling. Thus fluids are generally more difficult to formulate in discrete (individual) forms e.g. dosage forms than solids. It would therefore be desirable to have a form which presents fluid active ingredients in a way which can be easily and directly manufactured and shaped while retaining the benefits of fluids described above.

Shingel et al. (J Mater Sci: Mater Med 2008) describe a solid emulsion gel for topical delivery of hydrophilic and lipophilic drugs. A solid emulsion is normally a type of colloid in which a solid is dispersed in a liquid. However, Shingel et al. use the term to denote an oil-in-water (o/w) emulsion in which the aqueous continuous phase is a solid gel resulting from cross-linking between protein (acting also as stabilizer) and a poly ethylene glycol (PEG) derivative (activated PEG synthesised by reacting the polymer with nitrophenyl chloroformate). The researchers cast solid emulsion gel between two films to form a 1.2 mm thick sheet. According to Shingel et al., the solid aqueous phase acts like a hydrogel in its ability to absorb and then impart water e.g. when placed on skin requiring hydration. The emulsion, however, is not re-established on rehydration of the solid emulsion gel. Rather, the cross-linking has created protein-coated oil droplets (diameter range 5-20 μm) immobilized individually or as coalesced neighbouring droplets.

A particular industrial application of the present invention is in formulation for oral administration of active pharmaceuticals, nutraceuticals and food additives as well as immunomodulators, immunomodulating therapeutics and supplements.

For successful oral administration in these fields, the active principle must be in solution for local effect or systemic absorption, it must usually be stabilized before release (including protection from degrading stomach acids, pH degradation, proteolytic enzymes etc) and it must be permeable, with degrees of necessary permeability depending on whether local or systemic effect is required.

Additional requirements which pose problems in developing oral dosage forms are ease and cost of manufacture including scaleability, reproducibility and shelf-life.

If the active principle is to be delivered to the colon, as may be desirable eg. for local treatment of colonic disease, for presentation of the active principle to specific immune cells or for systemic or lymphatic absorption, additional constraints and requirements arise. Related or separate issues must be overcome if the active principle (and/or associated excipients) is desired to sequester, absorb or adsorb toxins, pollutants or other exogenous agents.

A variety of solutions to these individual problems have been identified but it is more challenging to resolve multiple such problems simultaneously in a single oral dosage form. The above described formulation issues are often greater for water-insoluble or poorly water-soluble active entities.

The above described formulation issues are often greater for water-insoluble or poorly water-soluble active entities.

Some of the issues mentioned above can be subdivided into more specific challenges. For example, the general requirement for the active principle to be in solution can be addressed by formulating it in a dissolved state and maintaining that dissolved state until release so avoiding reliance on dissolution in vivo (a "pre-dissolved" active principle). The technical challenge then becomes how to maintain the solubilized state and prevent release until the target release zone (eg colon) is reached.

A further specific need within the general requirement for the active principle to be in solution is the maintenance of the formulated active principle in a dissolved state as well as immediately after dispersion/egress from its carrier or matrix.

A particular problem in formulating active principles in a dissolved state (eg by encapsulation of solution in minispheres) arises when such dosage forms are coated with polymers intended to modify drug release characteristics. The coating may prevent full, sufficient or predictable release of active principle in the gastro-intestinal tract (GIT) or, through unpredictable swelling of or poration (pore formation) in the coating, create excess variability in release within a population.

For hydrophobic active principles, it is particularly desirable to increase water solubility or miscibility as well as to increase stability and reduce volatility. It is likewise a goal to control the availability of the active principle, particularly the bioavailability. One approach to these issues has been to use cyclodextrins, especially modified cyclodextrins as described e.g. in US 2006/0148756 A1 (Darcy et al). However, use of cyclodextrins although valuable in particular situations, can add manufacturing and quality control complexity to oral drug formulation and manufacture.

The oral delivery of combinations of otherwise physico-chemically incompatible drugs or of drugs (especially oil-soluble drugs) in soluble ("pre-solubliized") form or to mask the unpleasant or undesirable taste or smell of active principles, has been addressed by drug delivery systems having distinct compartments within a single administrative form—see for example U.S. Pat. No. 7,431,943 (Villa et al.). In such cases, the objective is often to prevent a first drug (eg hydrophobic drug with limited stability in aqueous milieu) from coming into contact with a second drug (eg hydrophilic drug dissolved in aqueous milieu) or in the case of a single active principle to maintain it in liquid form (eg as a liquid core within a capsule) either to mask taste/smell or to ensure it is delivered in active ("pre-dissolved") form at the desired intestinal location. In such situations, particularly when an enteric, sustained or delayed release coating is also applied to the drug form, the spatial asymmetries in the dosage form potentially lead to unpredictable release characteristics and/or unacceptable variability of drug release, bioavailability or dynamic/clinical response. In other words, distinct kinetic release characteristics apply to each compartment. This can make it difficult to achieve controlled e.g. simultaneous release of multiple drugs contained in a single form.

A related challenge in co-delivery (following co-administration) of more than one active principle is control (avoidance or enhancement, depending on the desired outcome) of interactions between the two or more active principles (or indeed, excipients) at the point(s) of release.

A further complication arising from inclusion of a liquid core within a capsule or minicapsule format is that for minicapsules to form, there is a very low threshold for surfactant in the core and this places a constraint on formulation options should it be desirable (see below) to include a surfactant in the liquid core. This is because the need for surface tension to create and maintain capsules precludes or limits use of surfactants as the reduction in surface tension caused by the surfactant in the core can destroy the integrity of the capsule or cause a more monolithic format where for example a shell or capsular layer may be desired. Thus it can be difficult to formulate liquid, emulsified or pre-solubilized active principles with surfactants which, as mentioned, may for a variety of reasons be desirable.

US Pharmacopoiea (USP), European Pharmacopoiea (EP), Japanese Pharmacopoiea (JP) and others are official public standards-setting authorities for medicines and other health care products manufactured or sold in the United States, Europe, Japan etc. Among other things, the Pharmacopoiea set recognized standards for the quality control of drug formulations to help ensure the consistency of products made for public consumption. These standards include dissolution methods, apparatus and media, often referred to as "compendial" e.g. "compendial media" meaning standard dissolution media described in USP, EP, JP etc. In the dissolution testing of sparingly water-soluble drug products, surfactants may be added to the medium to improve simulation of the environment in the GI tract—see eg. Noory et al. Dissolution Technologies, February 2000, Article 3.

The advantage of compendial methods is their relative simplicity. Their perceived disadavantage is their relatively poor predictive value in terms of assessing likely in vivo performance even with addition of surfactant to the medium. In order to enhance predictability, various non-compendial media as well as more elaborate dissolution apparatus and methods achieving improved in vivo/in vitro correlation (IVIVIC) have been developed particularly to measure colonic release—see e.g. Klein et al., J. Controlled Release, 130 (2008) 216-219.

Surfactants are also known to have been incorporated in oral pharmaceutical formulations, often as components of (usually) oil-in-water emulsions or self-emulsifying drug delivery systems (SEDDS) which are oil-phase-only formulations which spontaneously form emulsions on addition to water (sometimes therefore referred to as pre-emulsions). Where the oil droplets in these emulsions are very small, they are referred to as microemulsions (and their precursors as SMEDDS).

In general, the presence of surfactants in pharmaceutical formulations can be said to be an attempt to mimic the effect of bile salts and others, the natural surfactants synthesised in the liver and present in the GI tract. One of the main functions of bile salts is to solubilise fats in the GI tract and to facilitate their absorption into the systemic circulation and this gives an indication as to why it can be advantageous to use emulsion systems to enhance the systemic absorption of oil soluble and/or hydrophobic drugs. However, the goal of oral drug delivery is not always (or not solely) systemic absorption. If systemic absorption was not wanted, for example if local delivery with reduced, limited or negligible systemic absorption was the objective, the requirement or role, if any, for surfactants may be different.

With the rapid progress in biotechnology, peptide drugs are becoming important as therapeutic agents. A wide variety of peptides have been used as drugs, including hormones, nucleic acids, synthetic peptides, enzyme substrates and inhibitors. Although they are highly potent and specific in their physiological functions, most of them are difficult to administer orally because of the unique physicochemical properties of peptides including molecular size, poor solubility, short plasma half-life, requirement for specialised mechanisms for membrane transport and susceptibility to enzymatic breakdown (intestinal, pre-systemic and systemic). Many different approaches have been used to improve the oral absorption and enhance the bioavailability of peptide drugs. In recent years, enhanced bioavailability after oral administration has been reported by using microemulsion systems which are thermodynamically stable, isotropically clear dispersions of two immiscible liquids such as oil and water stabilized by an interfacial film of surfactant molecules. The advantages of microemulsions as drug delivery systems is the improvement of drug solubilization and protection against enzymatic hydrolysis, as well as the potential for enhanced absorption (eg from the jejunum but also the colon) due to surfactant-induced permeability changes.

However, there are a large number of technical variables which must be understood in order to design a microemulsion system suitable for a particular purpose or drug. The physicochemical properties such as drug stability, proportions of oil and water phases and the size of microemulsion droplets all affect outcome. If one or more surfactants are used, additional uncertainties arise such as the influence of surfactant to co-surfactant ratio, a consideration which is itself affected by the choice of oil in the oil phase and/or choice of surfactant or surfactant type.

A peptide drug which has been widely studied for the optimisation of microemulsion systems is ciclosporin A (International Non-Proprietary Name or INN) also known as cyclosporin(e) A.

In a microemulsion system of ciclosporin A obtained by using polyoxyethylated castor oil (CREMOPHOR® EL) as a surfactant, TRANSCUTOL® as a co-surfactant and caprylic/capric tryglyceride (CAPTEX® 355) as an oil, Gao et al (1998) in International Journal of Pharmaceutics 161 (1998) 75-86 achieved microemulsion stability with high ciclosporin A solubility, small droplet size and fast dispersion rate when selecting a CREMOPHOR® EL: TRANSCUTOL®: CAP- TEX® 355 ratio of 10:5:4. No further formulation of these microemulsions was described.

UK patent application 2,222,770 (SANDOZ LTD) describes galenic formulations which contain cyclosporines in the form of microemulsions (comprising a hydrophilic phase, a lipophilic phase and a surfactant) or microemulsion preconcentrates (no hydrophilic phase) also known as premicroemulsion concentrates. Such preconcentrates spontaneously form microemulsions in an aqueous medium for example in water or in the gastric juices after oral administration. With a maximisation of systemic absorption with good inter-subject variability being the objectives, this British patent application did not describe or address the challenges and problems of formulating cyclosporine A (also spelt cyclosporin A or ciclosporin A) for delivery to the colon and/or to sections of the GIT where absorption of cyclosporin is limited.

Kim et al. (Pharmaceutical Research, Vol 18, N° 4, 2001) describe a combined oral dosing regimen of premicroemulsion concentrates (as in UK patent application 2,222,770) and enteric coated solid-state premicroemulsion concentrates with the objective of achieving high systemic absorption following oral administration. In both cases, microemulsions are formed on addition to water/aqueous media. The enteric coated solid state preconcentrates are powders made by mixing the oil phase (premicroemulsion concentrate) with polymer dissolved in acetone. Removal of acetone leaves a film which is then powdered.

For colonic disease or to achieve absorption of drugs from the colon, colon-specific delivery systems must prevent the release of the drug in the upper part of the GIT yet release it on reaching the colon. Apart from pro-drugs activated by contact with the colonic milieu (eg specific bacteria or their enzymes), pure formulation approaches include pH and time-dependent polymer-mediated technologies. However, while variations in pH between the small intestine and the colon are well documented, the differences can be small and can vary between individuals. This can make pH-dependent systems unreliable in obtaining a predictable drug release profile. Time-dependent systems depend on the transit time of the delivery system in the GIT. A major limitation with these systems is that in vivo variation in the small intestinal transit time may lead to release of the bioactive (active principle) in the small intestine (too early) or in the terminal part of the colon (too late). The patho-physiological state of the individual recipient of such oral drug delivery systems also has a significant effect on the performance of these time-dependent systems—patients with irritable bowel syndrome and inflammatory bowel disease (including Crohn's disease and ulcerative colitis) often exhibit accelerated transit through the colon. Independently of these considerations, the size of the dosage form at the point of entry into the small intestine (pylorus) can have a significant effect on GI transit time and/or variability of response.

A number of other colon targeted delivery systems have been investigated. These systems include: intestinal pressure-controlled colon delivery capsules which rely on peristaltic waves occurring in the colon but not in the stomach and small intestine; combination of pH-sensitive polymer coatings (remaining intact in the upper GIT) with a coating of polysaccharides degradable only by bacteria found in the colon; pectin and galatomannan coating, degraded by colonic bacteria; and azo hydrogels progressively degraded by azoreductase produced by colonic bacteria. The preceding four systems are reviewed by Yang et al., International Journal of Pharmaceutics 235 (2002) 1-15, the entirety of which is incorporated herein by reference. Polysaccharide based delivery systems are of particular interest—see e.g. Kosaraju, Critical Reviews in Food Science and Nutrition, 45:251-258 (2005) the entirety of which is incorporated herein by reference. Nevertheless, for systems solely reliant on specific enzymatic activity in the colon, disease state can once again cause variability in the drug release profile as a result of pathological derangements in colonic flora (eg resulting from pH changes and changing amounts/activity of bacterial enzymes).

Beads of oil-in-water (o/w) emulsions are known. PCT application WO/2008/122967 (Sigmoid Pharma Limited) describes an oral composition comprising minicapsules having a liquid, semi-solid, or solid core and Figure 2 therein is a schematic of a semi-solid- or solid-filled minicapsule/minisphere wherein the active principle is solubilised or in a suspension form, with controlled release polymer coatings. Example 20 describes beads of an extruded emulsion drug suspension made from mixing an aqueous solution with an oil solution made up of squalene (a natural unsaturated hydrocarbon), Gelucire 44/14 and LABRAFIL® MS 1944 CS. The water-soluble active principle hydralazine is in the aqueous phase and the oil phase is 1.12 dry wt % of the formulation.

Dried oil-in-water (o/w) emulsions are known. U.S. Pat. No. 4,045,589 (Petrowski et al) describes a stable, dry, non-dairy fat emulsion product suitable for use as a coffee whitener. Such whiteners are prepared as dry emulsion concentrates which, on addition to an aqueous media such as coffee or tea, form a reconstituted oil-in-water emulsion which whitens and flavours the beverage. A first emulsifier is included in the liquid emulsion concentrate to promote the stability of the liquid emulsion and a second emulsifier (modified starch) is added to stabilize the emulsion through the drying step. Before drying, the fat particles in the emulsion average 1-3 μm in diameter. This liquid emulsion concentrate is dried to a moisture content not in excess of about 3%. In addition to spray drying, various other drying methods are described as possible including freeze drying, drying on heated drums etc.

U.S. Pat. No. 4,615,892 (Morehouse et al.) describes a dry imitation margarine or butter product which can be easily reconstituted to form a butter-like spread by slowly stirring the dry product into water accompanied by mixing with kitchen blenders. The dry product is made from an oil-in-water emulsion of an edible fat and a starch hydrolyzate and water. This emulsion is then dried e.g. by freeze or spray drying to reduce the moisture content to less than about 6%. During drying, agitation must be minimised and temperatures maintained above about 30° C. to prevent phase inversion prior to drying. The result is a protective film of starch hydrolyzate around the fat droplets in powder form.

U.S. Pat. No. 4,540,602 (Motoyama et al.) describes an activated pharmaceutical composition containing a solid drug that is scarcely soluble in water. When the composition is administered orally, the drug is readily absorbed to attain its high blood concentration quickly. To achieve this, the drug is dispersed in water in the presence of a water-soluble high-molecular weight substance to form finely divided particles not greater than 10 μm in diameter and then the water is removed to generate a finely divided drug coated with the water-soluble high-molecular substance in the form of a powder or granules. Emphasis is placed on achieving powders or granulates of particle size in the sub-micron range to optimise absorption from the intestinal mucosa. The water-soluble high-molecular weight substance can be a polymeric substance such as gelatin or gum arabic (Example 8 illustrates a combination of these two) or a cellulose derivative such as hydroxymethyl cellulose, methyl cellulose, hydroxyethyl cellulose, hydroxypropyl methylcellulose, hydroxypropyl ethylcellulose, carboxymethyl cellulose sodium and the like. Where the scarcely soluble drug is first dissolved in a hydrophobic organic solvent, the dispersion can be an emulsion. The solvent can be low-boil or non-volatile in which case it remains after drying and can be orally administered without harmful effect (eg glycerides, liquid paraffin, squalane, squalene, lecithin, pristine, etc).

LiuXing et al in J. Controlled Release 93 (2003) 293-300 describe entrapment of peptide-loaded liposomes in calcium alginate gel beads ranging from 0.95 to 1.10 mm in size. The goal was to obtain a colonic release form of the entrapped peptide (bee venom) and to protect the peptide from enzymatic degradation and to disrupt the mucosal membrane to increase peptide absorption. The objective was to address the low drug incorporation efficiency arising from the porosity of alginate beads.

Other problems with use of alginate results from loss of active principle during gelation due to diffusion from the concentrated gel to a less concentrated large volume cross-linking solution—see e.g. Wells et al., Eur J. of Pharmaceutics and Biopharmaceutics 65 (2007) 329-335.

Toorisaka et al. (J. Controlled Release 107 (2005) 91-96) addressed the problem of physical-chemical instability of a solid-in-oil-in water (S/O/W) emulsion. The instability led to a need for storage at low temperatures, a major impediment to pharmaceutical development. The researchers resolved this by creating a dry S/O/W emulsion in which the active principle (insulin) coated with a surfactant was the solid phase dispersed in soybean oil (oil internal phase). This was then homogenized with aqueous hydroxypropylmethylcellulose phthalate (HPMCP) to form the S/O/W emulsion. This was then dropped into hydrochloric acid to gellify the HPMCP and the resultant spherical microparticles were lyophilized to yield 1 μm diameter oil droplets coated with HPMCP. This process has many steps and is therefore complex to industrialise.

BRIEF SUMMARY OF THE DISCLOSURE

In accordance with the present invention there is provided a composition comprising a water-soluble polymer matrix in which are dispersed droplets of oil, the composition comprising an active principle. The invention includes embodiments in which the active principle is included in at least some of the oil droplets as well as embodiments in which the oil droplets are free of active principle. The oil droplets are released as the matrix containing them dissolves in an aqueous medium. In one embodiment, the oil droplets are substantially immobilized in or by the matrix and the immobilizing feature is lost as the matrix dissolves in aqueous media. In certain embodiments, the oil drops may collectively be referred to as the oil phase of the composition of the invention.

In one embodiment, the invention provides a composition comprising a water-soluble polymer matrix in which are dispersed droplets of oil, the matrix including a surfactant and the composition comprising an active principle. In another embodiment, the invention provides a composition comprising a water-soluble polymer matrix in which are dispersed droplets of oil, the oil comprising a surfactant and the composition comprising an active principle. In a further embodiment, the invention provides a composition comprising a water-soluble polymer matrix in which are dispersed droplets of oil, the matrix including a surfactant, the oil comprising a surfactant, and the composition comprising an active principle.

The extent to which dissolution may affect the composition's physical form and features depends on the initial shape, size and make-up of the composition. Where the composition bears a coat, the rate and manner of dissolution can be modified (see below).

In one aspect, the present invention can be described as a dried oil-in-water (o/w) emulsion, one embodiment of which is non-powdered. Another embodiment is moulded and/or shaped e.g. in the form of beads, especially mini-beads e.g. spherical mini-beads. The composition of the invention generally comprises multiple oil drops or droplets within a moulded or shaped form e.g. a mini-bead.

Another aspect of the present invention provides a composition (suitable e.g. for pharmaceutical or nutraceutical use) comprising a plurality of optionally coated mini-beads of a water-soluble polymer matrix. In a particular embodiment, the present invention provides a composition comprising a plurality of mini-beads of dried oil-in-water emulsion.

In either case, at least some of the mini-beads (eg a first population) may comprise an active principle (or more than one) and optionally other beads (eg a second population) which comprise an active principle (or more than one) or one population may be free of active principles or include "deactivating" principles e.g. enzyme or toxin sequesters or include active excipients, such as, for example, permeability enhancers, which may enhance, moderate or potentiate the effect of an active principle in another population. In related embodiments, the composition of the invention may comprise multiple populations of mini-spheres. The active principles may be the same or different as between populations.

In a specific embodiment, one or more active principle(s) is (are) incorporated in the oil phase of the composition or dried emulsion. In another specific embodiment, one or more active principle(s) is (are) incorporated in the aqueous phase of the composition or dried emulsion. In another embodiment, the beads may be coated with a polymer to alter the release profile or to protect the bead and/or the active principle within the bead from degradation or oxidation or hydrolysis or proteolysis or degradation mediated by high or low pH.

The composition of the invention is of particular interest for active principles of low aqueous solubility and/or liposoluble compounds (active principles) where incorporation into the oil phase brings particular advantages.

Thus in one aspect, the relation relates to formulating active principles for oral administration as mini-beads of dried oil-in-water emulsions in which the active principle can be incorporated in the oil phase of the emulsion and with the beads being optionally coated with a polymer.

The water-soluble immobilizing polymer matrix (or in one aspect, the aqueous phase of a dried emulsion) comprises, in one embodiment, a cross-linked water-soluble polymer e.g. resulting from chemical or physico-chemical (eg drying) solidification of a fluid aqueous continuous phase such that, in the matrix or dried emulsion, water is substantially absent and the oil droplets are immobilized. In this embodiment, the dried aqueous phase can therefore be referred to as an immobilization matrix.

The term "dried emulsion" generally means an emulsion whose internal (discontinuous) phase has been immobilized in a substantially solid or solidified external phase. The solid external phase dissolves on contact with an aqueous medium.

The term "matrix" is a term well-known in the art and generally means, according to context, a solid, semi-solid, undissolved or not-yet-dissolved material which provides structure and volume to a composition. In some contexts, the term "matrix" may mean a scaffold.

Solidification of the external phase may have arisen through various means including chemically (eg by cross-linking) or physically (eg by cooling or heating). By use of the term "dried", it is not sought to imply that a drying step is necessary to produce the dried emulsion (although this is not excluded) rather that the solid or solidified aqueous external phase is substantially free of water or free of available water. In this respect, the term "aqueous phase" is nevertheless employed in this document to denote the external (continuous) phase of the composition of the invention even though water, in certain embodiments, is largely absent from (or trapped within the cross-linked matrix of) the composition of the invention, particularly when in the form of mini-beads. The external phase of the composition of the invention is however water-soluble and dissolves in aqueous media. In one embodiment, the oil droplets are released when the aqueous phase dissolves or is exposed to aqueous media.

The term "released" in relation to the oil droplets means free to move, egress, coalesce, dissolve, (re)emulsify etc. although actual movement, egression, coalescence, association or (re)emulsification is not a requirement ie. may not occur and indeed may intentionally be constrained e.g. by presence of a coat or coating and/or by incorporation of certain constraining or retarding substances into the water-soluble polymer matrix.

It has additionally been found, to the inventors' surprise, that within the broad invention described herein, i.e. in certain embodiments, the constituents of the oil phase can be chosen to produce particular advantages in relation to certain active principles, particularly hydrophobic and/or lipophilic active principles. In particular it has been found that judicious choice of oil components one of which may be a surfactant allows certain lipophilic active principles to be solubilized in such a way as to maintain the solubilized state until the target release zone of the GI tract (eg colon) is reached. Indeed, selection of a particular kind of oil e.g. with surfactant properties, can in certain embodiments yield compositions whose oil phase is otherwise free of surfactant and in other embodiments yield compositions in which the aqueous phase is free of surfactant. In this group of embodiments, the inclusion of a surfactant in the aqueous phase is however preferred, particularly if it is desired to obtain a microemulsion according to the invention.

Another surprising development from the work leading to the present invention is that, for certain embodiments, the inclusion in the aqueous phase of a surfactant (described below) leads to improved dissolution of the active principle. In particular, it has been found that, when the composition of the invention is in the form of beads bearing a polymeric coating, inclusion of a surfactant in the aqueous phase enhances dispersion/egress through pores or other openings in the polymer coat (or other local removal, swelling or weakening of the polymer coat). Where the oil phase comprises a surfactant, the surfactant included in the aqueous phase may be different from any surfactant included in the oil phase.

For certain of the mini-bead embodiments, a further unexpected benefit arising from the work leading to the present invention is that selection of the appropriate combination of surfactants for the aqueous and oil phases leads to the maintenance of the API in a dissolved (or semi-dissolved or pre-dissolved) state on or immediately after dispersion/egress from the water-soluble matrix and (if present) polymer coating on the beads. For certain active principles, a particular choice of surfactant combination (described below) ensures immediate or early activity (or absorption) of the active principle at the site of release from the mini-bead.

Against the background of increasing sophistication and complexity of dissolution methods, media and apparatus, the present applicant and inventors have also surprisingly found that USP/EP/JP etc (compendial) methods and media can, contrary to expectations, provide for certain embodiments a valuable guide to in vivo performance—for example the time required for a given proportion of sample (composition or dosage form) to dissolve and/or release active principle. This surprising finding applies in a particular embodiment to poorly water-soluble drugs where the inventors/applicants have found that no surfactant need be added to the medium to achieve full dissolution/dispersion within a reasonable time frame noting, however, that low levels of surfactant in the medium may be desirable to maintain dissolution for longer periods.

In relation to specific embodiments, the present applicants/inventors have found that the advantages of compendial methods and media are particularly applicable to the development of novel compositions which incorporate a colonic release component. In addition, the present applications/inventors have found in relation to certain embodiments that the use of surfactants in compendial dissolution media, while aiding full dissolution for testing purposes, do not reflect in vivo conditions, particularly in the colon.

According to certain embodiments, complete or substantially complete dissolution of active principle (API) in USP/EP/JP etc dissolution apparatus using standard media can be achieved without addition of surfactant to the dissolution medium (and that maintenance of dissolution can be achieved with addition of very low quantities of surfactant to the dissolution medium) by incorporating in the composition according to this embodiment of the invention one or more surfactants even when the quantity of surfactant incorporated into the composition is much smaller than would have been required in the medium to achieve a comparable degree of dissolution of a composition (or formulation) containing no surfactant. In fact, one aspect of the present invention (described in more detail below) is the incorporation of surfactants in the composition of the invention, particularly in the mini-bead embodiment of the invention.

In particular, it has surprisingly been found in relation to certain embodiments that the composition according to the invention leads to complete or substantially complete dissolution of active principle (API) in USP/EP/JP etc dissolution apparatus using standard media without addition (or with addition of only small amounts of) surfactant to the dissolution medium (sufficient to maintain rather than establish dissolution) by incorporating in to the formulation or composition (preferably the aqueous phase thereof) one or more surfactants which facilitate complete or substantially complete dissolution/egress of API such that the quantity of surfactant incorporated into the composition is much smaller than would have been required in the medium to achieve a comparable degree of dissolution of a composition containing no surfactant. In essence, the invention provides in this embodiment a composition which dissolves in standard dissolution medium independently of the medium's surfactant content.

Another surprising feature emerging from experiments leading to the present invention is the make up of the optional polymeric coating. For instance, it has been discovered that judicious combination of different types of polymeric coating (described in more detail below) can produce unexpected advantages in relation to the in vitro dissolution and in vivo performance of the composition of the invention. In particular, it has now been discovered for these embodiments that inclusion of a polymer which degrades in the presence of bacterial enzymes present in the colon (and/or a polymer which encourages the formation of pores in the coating—a "pore-former") with a pH-independent polymer leads to release of active principle substantially in the colon or other pre-determined site of the GI tract. In a particular embodiment, the above mentioned polymer degradable by bacterial enzymes is water-soluble. At least in embodiments, the invention ameliorates or solves one or more of the shortcomings of the prior art. In particular, the invention comprises formulations or compositions which enable multiple problems of the prior art to be solved.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

DETAILED DESCRIPTION

As previously described, the present invention relates to a water-soluble polymer matrix composition in which are dispersed droplets of oil, the composition comprising an active principle.

The invention will now be described in detail by reference to the various components which the composition of the invention may comprise. The term "excipient" may be used occasionally to describe all or some of the components other than the active principle(s) bearing in mind that some excipients can be active and that some active principles can have excipient character.

If not otherwise stated, ingredients, components, excipients etc of the composition of the invention are suitable for one or more of the intended purposes discussed elsewhere herein e.g. are cosmetically acceptable, environmentally acceptable, pharmaceutically acceptable, acceptable as food additives etc.

Surfactants

In the description and claims of this specification, the term "surfactant" is employed as a contraction for "surface active agent". For the purposes of this description and claims, it is assumed that there are four major classifications of surfactants: anionic, cationic, nonionic, and amphoteric (zwitterionic). The nonionic surfactant remains whole, has no charge in aqueous solutions, and does not dissociate into positive and negative ions. Anionic surfactants are water-soluble, have a negative charge and dissociate into positive and negative ions when placed in water. The negative charge lowers the surface tension of water and acts as the surface-active agent. Cationic surfactants have a positive charge, and also dissociate into positive and negative ions when placed in water. In this case, the positive ions lower the surface tension of the water and act as the surfactant. The amphoteric (zwitterionic) surfactant assumes a positive charge in acidic solutions and performs as a cationic surfactant, or it assumes a negative charge in an alkaline solution and acts as an anionic surfactant.

Surfactants can also be classified according to their hydrophilic-lipophilic balance (HLB) which is a measure of the degree to which the surfactant is hydrophilic or lipophilic, determined by calculating values for the different regions of the molecule, as described (originally for non-ionic surfactants) by Griffin in 1949 and 1954 and later by Davies. The methods apply a formula to the molecular weight of the whole molecule and of the hydrophilic and lipophilic portions to give an arbitrary (semi-empirical) scale up to 40 although the usual range is between 0 and 20. An HLB value of 0 corresponds to a completely hydrophobic molecule, and a value of 20 would correspond to a molecule made up completely of hydrophilic components. The HLB value can be used to predict the surfactant properties of a molecule:

| HLB Value | Expected properties |
| --- | --- |
| 0 to 3 | antifoaming agent |
| from 4 to 6 | W/O emulsifier |
| from 7 to 9 | wetting agent |
| from 8 to 18 | an O/W emulsifier |
| from 13 to 15 | typical of detergents |
| 10 to 18 | solubiliser or hydrotrope |

Although HLB numbers are assigned to surfactants other than the non-ionic, for which the system was invented, HLB numbers for anionic, cationic, nonionic, and amphoteric (zwitterionic) surfactants can have less significance and often represent a relative or comparative number and not the result of a mathematical calculation. This is why it is possible to have surfactants above the "maximum" of 20. HLB numbers can however be useful to describe the HLB requirement of a desired application for a given emulsion system in order to achieve good performance.

Surfactants in Aqueous Phase

Surfactants which may be included in the aqueous phase of the inventive composition are preferably readily diffusing or diffusible surfactants to facilitate manufacturing and processing of the composition of the invention. Such surfactants can be of any particular type (ionic, non-ionic, zwitterionic) and may comprise as a proportion of dry weight of the composition from 0.1% to 6%, e.g. 0.1% to 5%. 0.1% to 4% or 0.1% to 3%, more preferably in a proportion of at least 1% and in particular between 1.0 and 4.5 or 5%, ideally within or just outside the 2-4% range, for example from 2 to 3% or approximately 2% or approximately 4%.

Unless otherwise stated or required, all percentages and ratios are by weight.

Preferred anionic surfactants for inclusion in the aqueous phase include perfluoro-octanoate (PFOA or PFO), perfluoro-octanesulfonate (PFOS), sodium dodecyl sulphate (SDS), ammonium lauryl sulphate, and other alkyl sulfate salts, sodium laureth sulphate, also known as sodium lauryl ether sulphate (SLES) and alkyl benzene sulphonate. A preferred anionic surfactant in the aqueous phase is SDS. Mixtures of anionic surfactants are also contemplated.

The physical form of the surfactant at the point of introduction into the aqueous phase during preparation plays a role in the ease of manufacture of the composition according to the invention. As such, although liquid surfactants can be employed, it is preferred to utilize a surfactant which is in solid form (eg crystalline, granules or powder) at room temperature, particularly when the aqueous phase comprises gelatin.

Possible non-ionic surfactants for the aqueous phase include perfluorocarbons, polyoxyethyleneglycol dodecyl ether (eg Brij such as, for example, Brij 35), Myrij, ® 20 or 80 (also known as Polysorbate), ® 80 or 85. Brij, Myrj and ® products are available commercially from Croda, formerly ICI.

In general, mixtures of surfactants can be utilised eg. to achieve optimum long term stability of the composition of the invention with shorter chain surfactants in general facilitating shorter term stability (an aid to processing) and longer chain surfactants facilitating longer term stability (an aid to shelf life). In some embodiments, shorter chain surfactants have up to $C_{10}$ alkyl (e.g. $C_6$-$C_{10}$ alkyl) as the hydrophobic portion of the surfactant whilst longer chain surfactants have $C_{10}$ or higher alkyl (e.g. $C_{10}$-$C_{22}$ alkyl) as the hydrophobic portion of the surfactant. It is envisaged that $C_{10}$ alkyl surfactants may facilitate processing or facilitate prolongation of shelf life, or both, depending on the identity of the other excipients and of the active principle(s). Higher alkyl may in particular implementations of the invention be $C_{11}$-$C_{22}$ or $C_{12}$-$C_{22}$ alkyl, and in some embodiments has a length of no greater than $C_{18}$.

Instead of (or as complement to) the surfactant in the aqueous phase, the invention also contemplates use of surfactant-like emulsifiers (also known as crystalisation inhibitors) such as, for example, HPMC (also known as hypromellose) although their use is generally contemplated in relatively smaller amounts to avoid high viscosity which may constrain processing options.

Other non-ionic surfactants which may be included in the aqueous phase include poloxamers which are nonionic triblock copolymers composed of a central hydrophobic chain of polyoxypropylene (poly(propylene oxide)) flanked by two hydrophilic chains of polyoxyethylene (poly(ethylene oxide)). Poloxamers are available commercially under the trade name Pluronics™. Such surfactants or similar larger polymeric surfactants are aqueously soluble and are therefore presented here as optional components of the aqueous phase. However, they may be used to reduce the amount of or to replace a higher HLB polymeric component of the oil phase (see also separate section) such as, for example, polyethoxylated castor oils (polyethylene glycol ethers) exemplified commercially as CREMOPHOR®. Diblock, tetrablock, multiblock, etc copolymers (poloxomers) are also included.

Another type of polymeric aqueous soluble surfactant which may be used in a similar way are anionic copolymers based on methacrylic acid and methyl methacrylate in which the ratio of the free carboxyl groups to ester groups is approx. 1:1 and with average molecular weight is approx. 135,000. Such a polymeric surfactant is available from Degussa under the trade name EUDRAGIT® L 100.

The surfactant included in the aqueous phase is preferably present within ranges noted above. In the mini-bead embodiment, avoidance of excess surfactant is desirable to avoid the "golf ball effect" whereby mini-beads when dried have a plurality of point-sized dimples in their surface (visible under the microscope). While not necessarily a major concern, such dimples can lead to variability in coating if it is desired to apply for example a polymer coat to the mini-beads. Although higher values within the preferred range generally increase the rate of egress/dissolution of mini-beads, the present inventors/applicants have surprisingly found that in certain circumstances higher levels of surfactant included in the composition of the invention can cause a counterintuitive drop in the in vitro dissolution profile including a drop in the total amount dissolved of the composition according to the invention. Based on the work leading up to this invention, it was established that the concentration of surfactant above which the dissolution profile dropped (or total amount of dissolved composition dropped) was approximately 5% by dry weight of the composition for example when SDS is selected as the surfactant. In certain embodiments, it is therefore preferred to have in the aqueous phase a surfactant, e.g. SDS, in an amount of less than 5% by dry weight of the total composition (for example, the composition may be in the form of beads or mini-beads, wherein the aqueous phase contains SDS or another surfactant in an amount of less than 5% by dry weight of the beads/mini-beads). In embodiments of the invention, the composition, e.g. in the form of beads or mini-beads, comprises in the aqueous phase surfactant in an amount of no more than 5%, no more than 4.5%, no more than 4% or no more than 3% by dry weight of the beads or mini-beads. In one class of embodiments, the surfactant is in an amount of at least 0.1% by dry weight of the beads or mini-beads. In another class of embodiments, the surfactant is in an amount of at least 1% by dry weight of the beads or mini-beads. In a further class of embodiments, the surfactant is in an amount of at least 2% by dry weight of the beads or mini-beads. Higher levels of surfactant in the aqueous phase (e.g. above 5% by weight of the total composition) restrict the processing parameters for manufacturing when certain manufacturing approaches are followed.

It is noteworthy that surfactants are used in dissolution testing media when complete dissolution of the composition being studied is otherwise not achievable. In respect of the amount of surfactant included in the aqueous phase of the composition of the present invention as described above, the inventors/applications have surprisingly found that such (small) quantities included in the composition have a much greater effect than larger quantities included in the dissolution medium.

In the case of the mini-bead embodiment, the present inventors hypothesise that the local concentration of surfactant in and around the mini-bead as it dissolves or disperses is more effective than an otherwise greater concentration in the medium as a whole. It is also believed, although the inventors/applicants do not necessarily intend to be bound by this or other hypotheses advanced in this text, that the surfactant in the beads assists API egress from within the polymer coat (if a coat is afterwards added to the mini-beads) and also possibly to shield the API from crystalisation and/or precipitation after release from the bead.

Thus it was a surprise for the present applicant/inventors to find that in certain embodiments complete or substantially complete dissolution of active principle (API) in USP/EP/JP etc dissolution apparatus using standard media can be achieved, using no or only minor amounts of surfactant in the dissolution medium, by incorporating in to the composition of the invention (eg dosage form) one or more surfactants even when the quantity of surfactant incorporated into the formulation is much smaller than would have been required in the medium to achieve a comparable degree of dissolution of a formulation containing no surfactant. The one or more surfactants may be comprised in the aqueous phase (the polymer matrix) or the oil phase, or both, and are in particular comprised in at least the aqueous phase and optionally also in the oil phase.

These observations are particularly relevant to the class of mini-bead embodiments of the invention, in particular where an oil-soluble API such as, for example, ciclosporin is incorporated in the oil phase and the mini-bead comprises a surfactant, e.g. in at least the aqueous phase (polymer matrix). On full dissolution of the composition of the invention in standard 900-1000 mL dissolution pots using compendial medium, the concentration of surfactant in an exemplary embodiment would be of the order of 0.001% ie. much lower than the amount (around 0.5%-1%) typically added to the dissolution medium. Putting it another way, very significantly greater amounts of surfactant would need to be included in this embodiment of the composition of the invention in order to achieve a fully diluted equivalent concentration of surfactant typically used in 900-1000 mL dissolution pots.

High surfactant concentrations in the dissolution medium can generate very good in vitro data but which is not necessarily predictive of in vivo performance (eg pharmacokinetic profile). In contrast, incorporation of (much lower overall quantities of) surfactant in one embodiment of the mini-beads of the invention produces unexpectedly superior in-vivo performance. The inventors/applicants hypothesise (without wishing to be bound by the hypothesis) that surfactant in the dissolution medium is more playing the role of a dispersing agent (bringing other components into the dissolution medium) rather than its classical role as an aid to dissolution and that it is the surfactant included in the aqueous phase of this embodiment of the composition of the invention which ensures or enables dissolution. In this setting, the small amount of surfactant included in the dissolution medium therefore makes the test more a dispersion test than a dissolution test and achieves dissolution/dispersion maintenance for the purposes of compendial methods.

Oil Phase

Any pharmaceutically suitable oil or oil acceptable for food use (or other chosen application) may be used to constitute the oil phase (oil drops) according to the invention. In terms of dry weight of the composition of the invention, the oil phase generally comprises a proportion from 10% to 85%, preferably 15% to 50%, more preferably 20% to 30% or from 35% to 45% e.g. for vaccine formulations. The term "oil" means any substance that is wholly or partially liquid at ambient temperature or close-to-ambient temperature e.g. between 10° C. and 40° C. or between 15° C. and 35° C., and which is hydrophobic but soluble in at least one organic solvent. Oils include vegetable oils (eg neem oil), petrochemical oils, and volatile essential oils.

Oils which may be included in the oil phase include polyunsaturated fatty acids such as, for example, omega-3 oils for example eicosapentanoic acid (EPA), docosohexaenoic acid (DHA), alpha-linoleic acid (ALA), conjugated linoleic acid (CLA). Preferably ultrapure EPA, DHA or ALA or CLA are used e.g. purity up to or above 98%. Omega oils may be sourced e.g. from any appropriate plant e.g. sacha inchi. Such oils may be used singly e.g. EPA or DHA or ALA or CLA or in any combination. Combinations of such components including binary, tertiary etc combinations in any ratio are also contemplated e.g. a binary mixture of EPA and DHA in a ratio of 1:5 available commercially under the trade name Epax 6000.

Oils which may be included in the oil phase are particularly natural triglyceride-based oils which include olive oil, sesame oil, coconut oil, palm kernel oil. Oils which are particularly preferred include saturated coconut and palm kernel oil-derived caprylic and capric fatty acids and glycerin e.g. as supplied under the trade name MIGLYOL® a range of which are available and from which one or more components of the oil phase of the invention may be selected including MIGLYOL® 810, 812 (caprylic/capric triglyceride); MIGLYOL® 818: (caprylic/capric/linoleic triglyceride); MIGLYOL® 829: (caprylic/capric/succinic triglyceride; MIGLYOL® 840: (propylene glycol dicaprylate/dicaprate). Note that MIGLYOL® 810/812 differ only in C8/C10-ratio and because of its low C10-content, the viscosity and cloud point of MIGLYOL® 810 are lower. The MIGLYOL® range is available commercially from Sasol Industries. As noted above, oils which may be included in the oil phase need not necessarily be liquid or fully liquid at room temperature. Waxy-type oils are also possible particularly when they have a surfactant activity. In this embodiment, suitable oils include polyglycol mono- and di-esters of 12-hydroxystearic acid (=lipophilic part) and of about 30% of free polyethylene glycol (=hydrophilic part). A small part of the 12-hydroxy group can be etherified with polyethylene glycol. Such waxy oils are available commercially e.g. from BASF under the trade name SOLUTOL®. An example is SOLUTOL® HS 15.

Alternative or additional oils which may be included in the oil phase according to the invention are medium chain tryglycerides such as for example Labrafac™ Lipophile manufactured by Gattefosse in particular product number WL1349.

Other possible (alternative or additional) oils include linoleoyl macrogolglycerides (polyoxylglycerides) such as, for example, LABRAFIL® (eg product number M2125CS by Gattefosse) and caprylocaproyl macrogolglycerides such as, for example, LABRASOL® by Gattefosse.

The oil phase may also include a solubilizer (which may also be referred to as anamphiphilic oil or a surfactant) and examples include polyethoxylated castor oils (polyethylene glycol ethers) which can be prepared by reacting ethylene oxide with castor oil. Commercial preparations may also be used as the solubilizer of the composition of the invention e.g. those commercial preparations which contain minor components such as, for example, polyethyelene glycol esters of ricinoleic acid, polyethyelene glycols and polyethyelene glycol ethers of glycerol. The preferred example is CREMOPHOR® by BASF Corp. also known as CREMOPHOR® EL. Alternative or additional solubilizers include phospholipids such as, for example, phosphatidylcholine. In embodiments of the composition of the invention which comprise a phospholipid solubilizer, the phospholipid solubilizer may be incorporated either in the aqueous phase or in the oil phase or both. If at least one phospholipid solubilizer is incorporated in each phase, it may be the same phospholipid solubilizer in both phases or different in each.

In one embodiment of the invention, the oil phase comprises more than one component. For example, as just mentioned, the oil phase may comprise a solubilizer.

Within this preferred embodiment, it is further preferred that the HLB of the oil be in the range 0-10 (preferably 1-5) and the HLB of the solubilizer be in the range 10-20 and optionally 11-20 (preferably 11-15).

Particularly preferred oils in the lower HLB category include medium chain tryglycerides, linoleoyl macrogolglycerides (polyoxyiglycerides), caprylocaproyl macrogolglycerides and caprylic/capric triglyceride. In terms of commercial products, particularly preferred oils in the lower HLB range are Labrafac™ Lipophile (eg 1349 WL), LABRAFIL®, LABRASOL®, CAPTEX® 355 and MIGLYOL® 810.

Particularly preferred solubilizers in the higher HLB category include polyethoxylated castor oils (polyethylene glycol ethers). The preferred commercial product for example is CREMOPHOR®.

While higher HLB solubilizers can be considered surfactants, the invention also contemplates, additionally or alternatively, inclusion of any other appropriate (non-ionic or other) surfactant in the oil phase.

For certain active principles, particularly hydrophobic/lipophilic agents such as cyclosporine A for example, the present inventors/applicants have observed to their surprise that incorporation into the oil phase of a solubilizer of high HLB and an oil of low HLB in a ratio of 1-4:1 by weight, e.g. 1.2-3.0:1 by weight, preferably 1.5-2.5:1 by weight and most preferably 1.8-2.2:1 by weight (high HLB: low HLB) advantageously stabilizes the emulsion before and after immobilization of the oil droplets in the aqueous phase. In this context "stabilize" means in particular that the embodiment improves dissolution and/or dispersion of the composition in vitro.

By "high" HLB is generally intended above 10, preferably from 10-14, more preferably between 12 and 13. By "low" HLB is generally intended below 10, preferably in the range 1 to 4, more preferably 1 to 2.

The oil phase preferably also comprises a co-solvent for the active principle (particularly in the case of poorly-soluble active principles such as for example cyclosporine or celecoxib). Examples of suitable co-solvents are 2-(2-ethoxyethoxy)ethanol available commercially under trade names Carbitol™, Carbitol cellosolve, TRANSCUTOL®, Dioxitol™, Poly-solv DE™, and Dowanal DE™; or the purer TRANSCUTOL® HP (99.9). TRANSCUTOL® P or HP, which are available commercially from Gattefosse, are preferred. Another possible co-solvent is poly-ethylene glycol. PEG of molecular weight 190-210 (eg. PEG 200) or 380-420 (eg. PEG 400) are preferred in this embodiment. Suitable PEG can be obtained commercially under the name "Carbowax" manufactured by Union Carbide Corporation although many alternative manufacturers or suppliers are possible.

A particularly preferred oil phase according to the invention is made up of an oil (low HLB), a solubilzer (high HLB) and a co-solvent. For example the following three commercial products: TRANSCUTOL® P (as co-solvent), Myglyol 810 (as oil) and CREMOPHOR® (as solubilizer) is particularly preferred. MIGLYOL® has a low HLB and CREMOPHOR® has a high HLB. This particularly preferred oil phase is preferably used to prepare (and is preferably a component of) a composition of the invention comprising cyclosporine. Another preferred oil phase comprises a waxy oil e.g. polyglycol mono- and di-esters of 12-hydroxystearic acid and free polyethylene glycol such as, for example, SOLUTOL® in which up to 1% of oil-soluble or hydrophobic antioxidant e.g. hydralazine or BHT is included. This second particularly preferred oil phase is preferably used to prepare (and is preferably a component of) a composition of the invention comprising tacrolimus. In specific embodiments, compositions according to the invention (and which comprise the aforementioned preferred oil phases) are free of other oily and/or hydrophobic components. In one embodiment, the composition comprises an oil-soluble or hydrophobic antioxidant e.g. hydralazine or BHT or carnosic acid or vitamin E.

The oil phase may also be a water-in-oil (w/o) emulsion so that the composition of the invention becomes a water-in-oil-in-water (w/o/w) emulsion.

The oil phase may include one or more active principles as discussed in more detail elsewhere herein particularly in the section entitled "Active Ingredients" et seq and may also include one or more volatile or non-volatile solvents, which may be the same or different from the co-solvent or solubilizer previously mentioned. Such solvents may for example remain in the composition of the invention following processing e.g. initial dissolution of the active principle, and have no particular function in the final composition. Alternatively, such solvents if present may function to maintain the active principle in a dissolved state (in solution) within the oil phase or to facilitate dispersion, egress etc. In other embodiments, the solvent may have partly or fully evaporated during processing and therefore be present in only minor quantities if at all. In a related embodiment, the solvent, particularly when a solvent which is both oil and water-soluble is used, may be partly or completely present in the aqeuous phase of the composition according to the invention. An example of such a solvent is ethanol. Another example is TRANSCUTOL® which is already mentioned as a co-solvent.

It will be appreciated, therefore, that the invention provides inter alia a bead or mini-bead comprising a water-soluble polymer matrix material in which are dispersed droplets of oil, the composition comprising an active principle and the oil comprising a combination of a high HLB compound, e.g. a solubilizer, and a low HLB compound, e.g. an oil, and optionally including a co-solvent.

Aqueous Phase

The principal component of the aqueous phase of the composition according to the invention (preferably between 20% and 70%, more preferably between 30% and 60%, still more preferably between 35% and 55%, by dry weight thereof) is a water-soluble polymer matrix material although other components may also be included as described below. The inventors/applicants have surprisingly found that inclusion of too little of the water-soluble polymer matrix material can for certain active principles lead to non-incorporation or leaching of the active out of the composition, particularly when in the form of mini-beads. For certain embodiments, for example vaccine compositions and compositions comprising SOLUTOL® or a retardant (see below), it is preferred that the aqueous phase comprise from 55% and 65% of the dry weight of the composition.

While mixtures of water-soluble polymer matrix materials are contemplated by the invention, preferably the composition of the present invention comprises a matrix material which is substantially a single material or type of material among those described herein and/or a matrix which can be solidified without inclusion of specific additional polymeric components in the aqueous phase. However, mixtures may be preferred to achieve certain performance characteristics. Thus it may be desired to incorporate certain constraining or retarding substances (retardants) into the water-soluble polymer matrix. In certain embodiments, such incorporation permits a coat (or coating) to be dispensed with. In other embodiments where a constraining or retarding agent is included into the water-soluble polymer matrix, a coat (or coating) may be present and desirable. For example, incorporation of a retarding agent which is insoluble in acid milieu (such as the stomach) is selected to prevent or retard release in the stomach and a coating may not be needed ie. the composition may be free of a coat/coating. Alternatively, incorporation of a retarding agent which is soluble in acid media may be selected to retard release in the intestine distal to the stomach. Again a coating may not be needed ie. the composition may be free of a coat/coating. However, a compositiion according to the invention which incorporates a retarding agent soluble in acid media may optionally be coated e.g. with an acid-resistant polymer to achieve particular advantage. Such a composition is protected from (complete) gastric release (or gastric release is retarded) owing to the effect of the acid-resistant polymer coat. Distal to the stomach, following loss of the coat, the acid-soluble agent retards release because the milieu of the small and large intestine is no longer acid. Retarding or constraining agents insoluble in acid mileu include polymers whose solubilitiy is pH-dependent ie soluble at higher pH. Such polymers are described in detail in the section below entitled "Coating" and such polymers may be used either as coats/coatings or as retarding agents incorporated into the water-soluble polymer matrix. An example of a suitable retarding agent mentioned in the section below entitled "Coating" is HPMCP (hydroxy-propyl-methyl-cellulose-phthalate also known as hypromellose phthalate) which is used to prevent release in the gastric environment since it is soluble above pH 5.5-see that section for other examples of polymers soluble in non-acid (basic) media. HPMCP may also be used as a pore-former. Retarding or constraining agents soluble in acid mileu include polymers whose solubility is pH-dependent ie. soluble at lower pH. Such polymers include cationic polymers such as for example copolymers based on dimethylaminoethyl methacrylate, butyl methacrylate, and methyl methacrylate. An example of such a cationic co-polymer which may be used according to the invention is EUDRAGIT® E PO commercially available from Evonik Industries.

In one embodiment, the water-soluble polymer matrix material may be of one or more of those selected from gelatine, agar, a polyethylene glycol, starch, casein, chitosan, soya bean protein, safflower protein, alginates, gellan gum, carrageenan, xanthan gum, phtalated gelatine, succinated gelatine, cellulosephtalate-acetate, oleoresin, polyvinylacetate, hydroxypropyl methyl cellulose, polymerisates of acrylic or methacrylic esters and polyvinylacetate-phtalate and any derivative of any of the foregoing. Mixtures of one or more water-soluble polymers comprising the matrix are also contemplated. In specific embodiments binary or tertiary etc combinations of any of the above substances are foreseen. An unexpected advantage of combining certain water-soluble polymers to form the matrix is that it allows for a reduction in the total amount of water-soluble polymer employed. This may have cost advantages or may allow greater loading of other materials such as, for example, one or more active principles. Inclusion of (addition of) a second water-soluble polymer to form the matrix may also give more strength to the composition of the invention e.g. beads.

In a preferred embodiment, the polymer matrix material is a hydrocolloid ie. a colloid system wherein the colloid particles are dispersed in water and depending on the quantity of water available can take on different states, e.g., gel or sol (liquid). It is preferred to use reversible hydrocolloids (eg agar, gelatin etc) as opposed to irreversible (single-state) hydrocolloids. Reversible hydrocolloids can exist in a gel and sol state, and alternate between states with the addition or elimination of heat. Gelatin is a thermo-reversible, rehydratable colloid and is particularly preferred. Gelatin derivatives such as, for example, succinated or phtalated gelatins are also contemplated. Hydrocolloids which may be used according to the invention include those derived from natural sources such as, for example, carrageenan (extracted from seaweed), gelatin (extracted from bovine, porcine, fish or vegetal sources), agar (from seaweed) and pectin (extracted from citrus peel, apple and other fruits). A non-animal based hydrocolloid may be preferred for certain applications e.g. administration to vegetarians or to individuals not wishing to ingest animal products for religious or health reasons. In relation to the use of carrageenan, reference is made to US patent application 2006/0029660 A1 (Fonkwe et al), the entirety of which is incorporated herein by reference.

The immobilized aqueous phase of the composition according to one embodiment of the invention is preferably a gel ie. a substantially dilute crosslinked system, which exhibits no flow when in the steady-state. The internal network structure of the solidified aqueous phase may result from physical or chemical bonds, as well as crystallites or other junctions that remain intact within an extending fluid e.g. water.

In an alternative preferred embodiment, the polymer matrix is a non-hydrocolloid gum. Examples are the cross-linked salts of alginic acid. For example, aqueous solutions of sodium alginate gums extracted from the walls of brown algae have the well known property of gelling when exposed to di- and trivalent cations. A typical divalent cation is calcium, often in the form of aqueous calcium chloride solution. It is preferred in this embodiment that the cross-linking or gelling have arisen through reaction with such a multivalent cation, particularly calcium.

In an alternative preferred embodiment, the polymer matrix is chitosan which can exist in the form of biogels with or without additives as described e.g. in U.S. Pat. No. 4,659,700 (Johnson & Johnson); by Kumar Majeti N. V. Ravi in Reactive and Functional Polymers, 46, 1, 2000; and by Paul et al. in ST.P. Pharma Science, 10, 5, 2000 the entirety of all 3 of which is incorporated herein by reference. Chitosan derivatives e.g. thiolyated entities are also contemplated.

In the embodiment in which gelatin is the polymer matrix of the invention, reference is hereby made to "bloom strength", a measure of the strength of a gel or gelatin developed in 1925 by O. T. Bloom. The test determines the weight (in grams) needed by a probe (normally with a diameter of 0.5 inch) to deflect the surface of the gel 4 mm without breaking it. The result is expressed in Bloom (grades) and usually ranges between 30 and 300 Bloom. To perform the Bloom test on gelatin, a 6.67% gelatin solution is kept for 17-18 hours at 10° C. prior to being tested.

According to the invention, in the embodiment in which gelatin is the polymer matrix, it is preferred to use gelatin with bloom strength between 200 and 300, preferably between 210 and 280.

According to the invention, in the embodiment in which gelatin is the water-soluble polymer matrix material, the gelatin may be sourced by a variety of means. For example, it can be obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Type A gelatin is somewhat preferred. Gelatin for use in the invention may also be derived from the skin of cold water fish. Blends of Type A and Type B gelatins can be used in the invention to obtain a gelatin with the requisite viscosity and bloom strength characteristics for mini-bead manufacture.

Commercially gelatin can be obtained from the Sigma Chemical Company, St. Louis, Mo. USA or from Nitta (http://www.nitta-gelatin.com).

Lower temperature gelatin (or gelatin derivatives or mixtures of gelatins with melting point reducers) or other polymer matrices able to be solidified at lower temperatures (eg sodium alginate described above) are preferred for example when the active principle to be incorporated in the composition of the invention is temperature-labile or whose activity may be affected by exposure to higher temperatures.

According to the invention, in the embodiment in which gelatin is the polymer, the starting gelatin material is preferably modified before manufacture to produce "soft gelatin" by the addition of a plasticizer or softener to the gelatin to adjust the hardness of the composition of the invention. The addition of plasticizer achieves enhanced softness and flexibility as may be desirable to optimise dissolution and/or further processing such as, for example, coating. Useful plasticizers of the present invention include glycerin (1,2,3-propanetriol), D-sorbitol (D-glucitol), sorbitol BP (a non-crystallizing sorbitol solution) or an aqueous solution of D-sorbitol and sorbitans (eg Andidriborb 85/70). Other or similar low molecular weight polyols are also contemplated. Polyethylene glycol may also be used although this is less preferred and indeed particularly preferred compositions of the invention are free or substantially free of PEG or derivatives thereof. Glycerin and D-sorbitol may be obtained from the Sigma Chemical Company, St. Louis, Mo. USA or Roquette, France.

As noted above, some constituents of the present invention may play more than one role. For example when one of the active principles (see below) is ibuprofen, it may also act as a plasticiser owing to its particular physico-chemical properties. Choice of ibuprofen has particular advantages in relation to higher loading as "conventional" plasticiser, for example dibutyl sebacate or DBS, may be reduced in quantity. Alternatively it is contemplated that the surfactants discussed above may be selected for their plasticiser characteristics to achieve particular advantage.

Softeners, if utilized, can be ideally incorporated in a proportion rising to 30%, preferably up to 20% and more preferably up to 10% by dry weight of the composition of the invention, even more preferably between 3 and 8%, and most preferably between 4% and 6%.

As noted in more detail above in the section on surfactants, it is preferred to include one or more surfactants in the aqueous phase. Certain surfactants may also act as plasticisers or softeners or vice versa.

Although not essential, the aqueous phase may also optionally contain a disintegrant where it is particularly desired to enhance the rate of disintegration of the composition of the invention.

Examples of disintegrants which may be included are alginic acid, croscarmellose sodium, crospovidone, low-substituted hydroxypropyl cellulose and sodium starch glycolate.

A crystalisation inhibitor (eg approximately 1% by dry weight of the composition) may also be included in the composition of the invention, preferably in the aqueous phase. An example is hydroxy propyl/methyl cellulose (HMC or HPMC, hypromellose etc) which may play other roles such as, for example, emulsifier (see above). In addition, the aqueous phase may include some or all of a solvent used during processing to dissolve, or facilitate dissolution of, an active principle e.g. an active principle comprised in the oil phase. An example is ethanol (see discussion above on use of solvents in oil phase).

The invention includes compositions comprising a solid phase comprising a water-soluble polymer matrix material and an oil phase dispersed in the solid phase.

Shape, Size and Geometry

The composition of the invention can be formed into a limitless number of shapes and sizes. In the section below describing the process for making the composition, various methods are given including pouring or introducing a fluid emulsion into a mould where it hardens or can be caused to harden. Thus the composition can be created in whichever form is desired by creating an appropriate mould (eg in the shape of a disc, pill or tablet). However, it is not essential to use a mould. For example, the composition may be in the form of a sheet e.g. resulting from pouring a fluid emulsion onto a flat surface where it hardens or can be caused to harden.

Alternatively, the composition may be in the form of spheres or spherical-like shapes made as described below. Preferably, the composition of the invention is in the form of substantially spherical, seamless beads, especially mini-beads. The absence of seams on the mini-bead surface is an advantage e.g. in further processing, for example coating, since it allows more consistent coating, flowability etc. The absence of seams on the mini-beads also enhances consistency of dissolution of the mini-beads.

The preferred size or diameter range of mini-beads according to the invention can be chosen to avoid retention in the stomach upon oral administration of the mini-beads. Larger dosage forms are retained for variable periods in the stomach and pass the pyloric sphincter only with food whereas smaller particles pass the pylorus independently of food. Selection of the appropriate size range (see below) thus makes the prediction of therapeutic effect post-dosing more accurate. Compared to a single large monolithic oral format such as, for example, a traditional compressed pill, a plurality of mini-beads released into the GI tract (as foreseen by the present invention) permits greater intestinal lumen dispersion so enhancing absorption via exposure to greater epithelial area, prevents irritation (e.g as otherwise seen with NSAIDs) and achieves greater topical coating (e.g. as may be desired for local drug effect in certain parts of the GI tract for example the colon). Reduction of residence time in the ileo-caecal junction is another advantage.

The composition of the invention is preferably monolithic meaning internally (ie. cross-sectionally) homogeneous. This is particularly preferred for the mini-bead embodiment.

In the embodiment of the present invention which is in the form of mini-beads, the mini-beads generally range in diameter from 0.5 mm to 10 mm with the upper limit preferably 5 mm. A particularly convenient upper limit is 2 mm with 1.7 mm being particularly preferred. The lower limit can be e.g. approximately 1 mm, preferably from 1.2 mm, more preferably from 1.3 mm, most preferably from 1.4 mm. While the invention may be practised in relation to the above size ranges, it is preferred to have a bead population which is substantially homogeneous as to bead size (diameter). In this respect, a given bead population may comprise beads of diameter substantially equal to the figures just given. More than one population of beads, differing as to bead size (diameter) may be combined within a single formulation. Thus the invention includes embodiments in which populations of beads have substantially homogeneous diameters of approximately 0.5 mm, 1.2 mm, 1.3 mm, 1.4 mm, 1.7 mm, 2 mm or 5 mm.

Another possible form of the composition of the invention is as hemispherical beads two of which may optionally be joined at the flat face to create a single mini-bead with two distinct halves, each having a distinct composition, if that is desired, e.g. each containing different active principles or the same active principles but different excipients e.g. to achieve differing permeability, solubilization or release profiles as between the two hemispheres.

The embodiment in which the composition of the invention takes the form of mini-beads can be further developed to create a larger mass of mini-beads e.g. via compression (with appropriate oil or powder-based binder and/or filler known to persons skilled in the art of pharmaceutical formulation and with the option of including additional quantities of the same API as in the composition of the invention or a different API a preferred example being where the composition of the invention takes the form of beads which comprise immediate or controlled release cyclosporine and the binder or filler comprises MMF, mycophenolate mofetil, an immunosuppressant) of a plurality of mini-beads which disintegrate at a different rate in different conditions than a unitary moulded form of the same shape. The larger (eg compressed) mass may itself take a variety of shapes including pill shapes, tablet shapes, capsule shapes etc. A particular problem which this version of the mini-bead embodiment solves is the "dead space" (above the settled particulate contents) and/or "void space" (between the particulate content elements) typically found in hardgel capsules filled with powders or pellets. In such pellet- or powder-filled capsules with dead/void space, a patient is required to swallow a larger capsule than would be necessary if the capsules contained no such dead space. The mini-beads of this embodiment of the invention may readily be compressed into a capsule to adopt the inner form of whichever capsule or shell may be desired leaving much reduced, e.g. essentially no, dead/void space. Alternatively the dead or void space can be used to advantage by suspending minibeads in a vehicle such as, for example, an oil which may be inert or may have functional properties such as, for example, permeability enhancement or enhanced dissolution or may comprise an active ingredient being the same or different from any active ingredients in the bead. For example, hard gelatin capsules may be filled with a liquid medium combined with uncoated and/or coated beads, The liquid medium may be one or more of the oil phase constituents described herein or it may be one or more surfactants, or one or more solubilizers. Particularly preferred but non-limiting examples are corn oil and the commercial products known as SPAN® 85, Labrafac™, TRANSCUTOL® P and ® 80. An example of a liquid medium which may be used in this embodiment and which contains an active principle is the commercially available cyclosporin pre-microemulstion NEORAL®. It is particularly preferred to formulate beads according to the invention in NEORAL® and to fill a hard gel capsule.

Another possible form of the composition of the invention is as a capsule in which the core of the composition is a solid (eg gastro-retentive float material such as, for example, biocarbonate salts) or a fluid (a gas or a liquid). If the core is a liquid, it may contain an active principle and/or excipients which may be the same or different from those described above. Like the hemispherical beads described above, such capsules may have two halves of different constitution and sealed hermetically to retain the internal fluid. An internal layer e.g. internal film layer of non-aqueous material on the inner face of the sphere, may be included if it is desired that the core be an aqueous liquid such that the internal layer prevents the aqueous core from coming into contact with the inner surface of the capsule. With or without an intermediate layer, the core may be a variant of the composition of the invention so that the composition of the invention, in the mini-bead embodiment, comprises a core made from a first composition according to the invention and a capsule made from a second composition according to the invention.

The mini-bead embodiment of the invention, while by itself offering a range of solutions to the issues identified above, may also be used as a starting point for creation of further eg. pharmaceutical or nutraceutical forms for example by using the mini-bead as a nonpareil seed on which additional layers of material can be applied as is well known to a person skilled in the art e.g. of pharmaceutical science. The material of the additional layers may comprise the same or different active principle and/or the same or different excipients as are described in this document. Such variants allow differential release of the same or different active principles and facilitate inclusion of multiple fixed-dose combination products as for example discussed in connection with the popularly termed "polypill" which denotes a single pill comprising more than one active principle in a fixed dose combination, an idea of particular relevance to cardiovascular medicine.

The composition of the invention may have a coat of additional material on its outer surface. This coat may be applied in a number of ways, including drug layering, as described more particularly in the section below entitled "coating". In one such embodiment, the composition of the invention comprises an acid within the bead e.g. included within the water soluble polymer matrix or as a liquid core in mini-capsular format and bicarbonate applied as a coat e.g. by drug layering. If the bead has a polymeric coat, e.g. to control release into the colon, the bicarbonate may optionally or additionally be included in or be absent from the coating polymer. This composition is intended to release carbon dioxide in the GI tract e.g. to reduce pain or to reduce inflammation. In a related embodiment, the core or the bead comprises an acid to enhance the solubility of active principles of various pKa (acid dissociation constant) in the small intestine or colon. Alternatively, the core or the bead comprises a base to enhance the solubility of active principles of various pKa in the stomach.

Other Characteristics

The composition of the invention, in certain embodiments, comprises one or more elements, components, excipients, structural features, functional features or other aspects of the prior art described above.

To summarise a limited number of embodiments of the invention, the composition as described above and elsewhere herein may additionally be one or more of the following: substantially water-free, in a gel state, in a solid state, undissolved, non-powdered, formed, shaped, and not in solution.

Unless geometrically designed to comprise inner aqueous compartments (eg w/o/w format or capsular format with liquid core), it is desirable that the composition of the invention is essentially or substantially dry, e.g. contains less than 5%, preferably less than 1% of free water by weight. The mini-beads are preferably homogeneous although processing conditions may be varied (see below) to achieve for example heterogeneity such as, for example, a harder skin and softer core with less than complete immobilization of oil droplets towards the core as opposed to the surface of the bead. Larger (eg non-beaded) forms or shapes of the composition according to the invention may particularly be engineered to embody such heterogeneity.

The low free-water content is a distinguishing feature of certain embodiments of the compositions of the present invention. The free-water content can be measured using thermogravimetic analysis (TGA), for example with commercially available instrumentation, e.g. using a TGA Q 500 of TA Q series instrument. TGA measures changes in weight in relation to a change in temperature. For example, a TGA method can comprise a temperature scan, e.g. from 20 to 400° C. at 20° C. per minute, where the moisture content is obtained from the sample weight loss at about 100 degrees Celsius.

In one embodiment, the oil droplets in the composition of the invention are homogeneously dispersed in the solidified aqueous phase (or in some embodiments the water-soluble polymer matrix material) with substantial absence of coalescence between adjacent oil droplets. Thus the emulsion is preferably maintained during solidification. Coalescence of neighbouring oil droplets, preferably only does so, if at all, on rehydration of the composition of the invention.

Depending on process parameters, droplet size can vary broadly e.g. from 10 nm to 10 µm (diameter). However, the inventors/applicants have found that it is beneficial to maintain droplet size in the range from 100 nm to 1 µm, e.g. from 300-700 nm. The term "emulsion" therefore includes microemulsions and nanoemulsions.

The composition of the invention generally comprises multiple oil drops or droplets within a moulded or shaped form e.g. a mini-bead which might typically contain many hundreds or thousands of droplets as distinct from a powder which generally derives from micron-sized particles incorporating a single or a small number of oil drops or droplets often following coalescence of smaller droplets during spray-drying. While powder embodiments are not excluded, the composition of the invention, if particulate, preferably comprises particles larger than powder particles such that the composition is in a non-powdered form.

In the embodiment in which the invention is in the form of minibeads, a plurality of minibeads may be presented in a single format e.g. contained in a single hardgel capsule which releases the mini-beads eg. in the stomach. Alternatively the minibeads may be presented in a sachet or other container which permits the minibeads to be sprinkled onto food or into a drink or to be administered via a feeding tube for example a naso-gastric tube or a duodenal feeding tube. Alternatively, the mini-beads may be administered as a tablet for example if a plurality of mini-beads are compressed into a single tablet as described elsewhere herein. Alternatively, the mini-beads may be filled e.g. compressed into a specialist bottle cap or otherwise fill a space in a specialised bottle cap or other element of a sealed container (or container to be sealed) such that e.g. on twisting the bottle cap, the mini-beads are released into a fluid or other contents of the bottle or vial such that the beads are dispersed (or dissolve) with or without agitation in such contents. An example is the Smart Delivery Cap manufactured by Humana Pharma International (HPI) S.p.A, Milan, Italy. A related or similar approach is also contemplated for e.g. timed release of mini-capsules into a reactor, feeding environment e.g. tank, incubator etc.

The mini-beads so-presented may be of a single type (or population) or may be of multiple types (or populations) differing between populations in relation to one or more features described herein e.g. different API or different excipients or different physical geometry, coated, multiply coated, uncoated etc.

In one embodiment, the invention allows for mini-beads having immediate release (IR) characteristics e.g. bearing no coat, enteric-only coat or coat designed to prevent release and/or dissolution of the bead only for a limited time or lacking a retardant in the aqueous phase. In another embodiment, the invention allows for mini-beads having delayed or sustained release (SR) characteristics e.g. bearing a coat (or more than one coat) as described in more detail elsewhere herein, particularly in the section entitled "coating". The invention also provides for an embodiment in which immediate release mini-beads are produced in combination with a Sustained Release or Controlled Release (CR) mini-beads in varying ratios of IR:SR/CR. The immediate release mini-beads can be combined with a Sustained or Controlled release mini-bead component in the following ratios (w/w by potency) e.g. 10% Immediate Release (IR)+90% Sustained (SR)/Controlled Release (CR) minicapsules; 20% IR+80% SR/CR; 30% IR+70% SR/CR; 40% IR+60% SR/CR and 50% IR+50% SR/CR.

Active Ingredients

The present invention provides a vehicle for delivery of active principles which can be of various types including cosmetic, food, food supplements, nutraceuticals, pharmaceuticals, aquaculture, etc. It can also include active principles used in sterilisation or purification of contaminated liquids e.g. water contaminated with pathogens for example bacteria. The composition of the invention can be used also to absorb active principles in order for example to remove pollutants from the environment including air or water or from the intestine or specific part thereof e.g. colon.

In addition, the composition of the invention may be used to deliver active principles which deactivate, inhibit, sequester or down-regulate enzymes e.g. in the intestinal lumen (for example lipases, proteinases etc) which may be desirable to abate the effects of a bacterial infection and or to facilitate the absorption of other active principles whose absorption may otherwise be affected by such enzymes.

The composition of the invention may also be used to remove fats from the intestine for example by inclusion of a fat absorber or fat sequestrant (or other agent susceptible of binding, reversibly or otherwise to fats present in the intestinal lumen).

Separately or in conjunction with one of the preceding functions, the composition of the invention may also include an active principle able to interact with bacteria in the gut for example by delivery of antibiotics (including lantibiotics or bacteriocins) to a specific portion of the gut so as to reduce side effects or, in the case of a peptide as active principle, its survival from degradation as it passes through the upper GI tract.

Other active principles contained in the same or a separate composition may sequester antibiotics e.g. in the lower small intestine, ileum or colon. Thus in one embodiment, the composition of the invention delivers antibiotics relatively proximally and reabsorbs them relatively distally to reduce the amount of excess antibiotic remaining in the colon and/or excreted. In a related embodiment, the composition of the invention comprises enzymes to break down or neutralise or deactivate antibiotics e.g. beta-lactams and delivers and/or releases these to target locations in the GI tract e.g. in the colon.

Active ingredients may also be included in the composition of the invention to enhance absorption of nutrients e.g. in the small intestine or to provide nutrition or nutritional supplementation. In a related embodiment, the composition of the invention comprises functional oils in combination with a natural plant or marine extract. An example of a natural plant extract is berberine which is a quaternary ammonium salt from the group of isoquinoline alkaloids. An example of functional oils (the term also includes "designer" oils) are medium chain triglycerides (MCTs) derived from tropical oils which have had longer chain and "bad" palmitic acid removed to leave medium chain "good" fatty acids behind. "Good" oils, such as, for example, omega-3-rich flaxseed oil may then be added to achieve variant functional oils.

The compositions of the present invention may be administered to an animal e.g. fish or mammal by any appropriate route including oral, anal, rectal, vaginal, urethral, intravenous, subcutaneous, transcutaneous, intraperitoneal etc or may be added to the environment e.g. food, drink, water etc for absorption by the animal. The invention also relates to a method of treating one or more animals just described by administering such a composition via the oral, anal, rectal, vaginal, urethral, intravenous, subcutaneous, transcutaneous or intraperitoneal route or by adding the composition to the environment e.g. food, drink, water etc for absorption by the animal.

A particular focus of the present invention is the delivery of pharmaceuticals. This applies particularly to the embodiment in which the composition takes the forms of mini-beads e.g. for oral administration. The composition may comprise one or more active principles (also referred to as active pharmaceutical ingredients or APIs) and it is preferred to incorporate lipophilic APIs (if any) in the oil phase and hydrophilic APIs (if any) in the aqueous phase. More than one active principle may be incorporated in a single mini-bead and/or in distinct populations of mini-beads within a single dosage form, e.g. hardgel capsule, and specific binary fixed dose combinations are discussed in a separate section below (although this section is not to be taken as a limitation on the full extent of possible binary combinations). Ternary, quaternary etc combinations are also contemplated.

In relation to its pharmaceutical applications, the invention applies to a wide range of drug types e.g. as classified according to the Biopharmaceutics Classification System (BCS) which comprises 4 classes:
Class I—High Permeability, High Solubility
Class II—High Permeability, Low Solubility
Class III—Low Permeability, High Solubility
Class IV—Low Permeability, Low Solubility In relation to the APIs incorporated in the oil phase of the invention, Classes II and IV are of particular relevance.

For the purposes of this description and claims, a drug substance is considered highly soluble when the highest dose strength is soluble in ≤250 ml water over a pH range of 1 to 7.5 (and of low solubility if not meeting these criteria) and highly permeable when the extent of absorption in humans is determined to be ≥90% of an administered dose, based on mass-balance or in comparison to an intravenous reference dose (and of low permeability if not meeting these criteria).

Again, for the purposes of this description and claims, a drug product is considered to be rapidly dissolving when ≥85% of the labeled amount of drug substance dissolves within 30 minutes using USP apparatus I or II in a volume of ≤900 ml buffer solutions. Usually the buffer is phosphate buffer (PBS) of pH 7.4.

Regarding solubility determination, further details are provided below and in relation to specific examples. However, in general terms, solubility determination is carried out by one of four methods:
Visual disappearance of drug
pH-solubility profile of test drug in aqueous media with a pH range of 1 to 7.5.
Shake-flask or titration method.
Analysis by a validated stability-indicating assay.

Permeability determination can be carried out by assessing the extent of absorption in humans or other in vivo permeability methods. Approaches include:
Mass-balance pharmacokinetic studies.
Absolute bioavailability studies.
In vivo intestinal perfusion studies in humans.
In vivo or in situ intestinal perfusion studies in animals
In vitro permeation experiments with excised human or animal intestinal tissue
In vitro permeation experiments across epithelial cell monolayers Permeability determination methodology is not standardised and results can therefore depend on experimental conditions. For example, some APIs e.g. cyclosporine A (CyA) can be classed as either Class II (high permeability, low solubility) or Class IV (low permeability, low solubility). Chiu et al in Pharmaceutical Research Volume 20, 5 2003 assign CyA to Class II, while Sharma et al in Farmaco. 2005 60 (11-12): 884-93 assign it to Class IV. Although there is agreement on low solubility, there is apparent disagreement on permeability and this is believed to be because permeability changes with the formulation and/or tissue site under study with Chiu et al. for example apparently discussing jejunal permeability.

For pharmaceutical applications, the composition of the invention may be applied to a very wide range of active principles with a particular focus being on hydrophobic/lipophilic active principles for incorporation in to the oil phase bearing in mind that hydrophilic active principles may also be included in the aqueous phase (including in the inner aqueous phase if the oil phase is a w/o emulsion).

For example the composition of the invention can be used in the case of insoluble active ingredients such as, for example, nifedipine, lipid soluble active ingredients such as, for example, gemfibrizol, and pH sensitive active ingredients such as, for example, captopril.

The composition of the invention in the mini-bead embodiment is also suitable for the administration of active ingredients which are sensitive to the pH environment in the stomach, such as, for example, omeprazole and other proton pump inhibitors used in anti-ulcer treatment. Active ingredients for the treatment or prevention of *H. pylori* infection are particularly contemplated.

The formulation according to the invention can also be used to improve the bioavailability of active ingredients such as, for example, terfenadine which have a low oral bioavailability. Moreover, the composition according to the invention can also be used to dramatically increase the absorption of active ingredients which are poorly absorbed from or are destroyed in the gastrointestinal tract such as, for example, captopril, cyclosporin, calcitonin, heparins and heparinoids. Certain antibiotics, including some lantibiotics e.g. lacticin are destroyed in the gastrointestinal tract by the action e.g. of enzymes such as, for example, α-chymotrypsin and pepsin or by acid. One embodiment of the invention relates to compositions which prevent or reduce such destruction and release such an active principle at a target site e.g. distal to the stomach or small intestine. Thus, in distinct embodiments, the invention provides compositions comprising captopril or cyclosporin or calcitonin or heparin or low molecular weight heparin or pentasccharide heparin derivative or heparinoids or lacticin. Nucleic acids such as, for example, siRNAs, may also be formulated in this way and the invention includes embodiments in which the composition comprises one or more nucleic acid.

Suitable classes of therapeutic agents which can be delivered using this invention include but are not limited to poorly water soluble drugs such as, for example, cardiovascular agents, lipid lowering agents, anti-diabetic agents e.g. PPAR-gamma activators, anti-epileptics, anti-infectives (including antibiotics such as, for example, lantibiotics and bacteriocins), anti-fungal agents, anti-viral agents, antipsychotic agents, immunosuppressants, protease inhibitors and cyclic peptides. In a related embodiment, the composition of the invention comprises an active principle capable of activating PPAR-gamma e.g. rosiglitazone or pioglitazone. The invention relates also to a method of treating inflammatory bowel disease by administering such a formulation to a mammal, e.g. a human patient, in need thereof.

Suitable classes of therapeutic agents which can be delivered using this invention include but are not limited to peptides, proteins, vaccines, and oligonucleotides, including non-covalent or covalent modified versions thereof including —NO, —HS and —$CO_2$ derivatives.

It is to be further appreciated that the present invention may be used to deliver a number of drugs, singly or in various combinations, as well as nutritional supplements or various nutritional or pharmaceutical adjuvants. The term "drug" used herein includes but is not limited to peptides or proteins (and mimetics as well as covalent, non-covalent or chemical analogues thereof), antigens, vaccines, hormones, analgesics, anti-migraine agents, anti-coagulant agents, medications directed to the treatment of diseases and conditions of the central nervous system, narcotic antagonists, immunosuppressants, immunostimulators, agents used in the treatment of AIDS, chelating agents, anti-anginal agents, chemotherapy agents, sedatives, anti-neoplastics, prostaglandins, antidiuretic agents, DNA or DNA/RNA molecules to support gene or other nucleic acid-based therapeutics and entities leading to various immunotherapies, including antigenic and nucleic acid-based vaccines or immunotherapies, primers and adjuvants of such as well as organisms that synthesize and secrete therapeutic or health modulating entities. The present invention may also be used to deliver NSAIDs and in one embodiment relates to a composition of an NSAID in particular for preventing and/or treating bowel cancer and/or polyps and/or to block PGP to enhance the effect of anti-cancer agents. The present invention may also be used to deliver bile salts or other active principles or primary bile acids e.g. chenodeoxycholic acid (CDCA), or derivatives e.g. salts thereof which are capable of binding to and activating the nuclear farnesoid X receptor (FXR). The invention also relates to a composition comprising such active principles and also to a method of treating or preventing hypercholesterolemia or diaorrhoea or chemotherapy-induced diaorrhoea or constipation-predominant irritable bowel syndrome (IBS-C) by administering such a formulation to a mammal, e.g. a human patient, in need thereof.

Moreover, the active pharmaceutical agent(s) included in the composition of the invention may be in a solubility-modified form so that when released in the colon or other target part of the GI tract, it (they) is (are) more or less readily absorbed (depending on the extent to which absorption is or is not desired).

As noted above, the active pharmaceutical agent(s) may be a small molecule, a macromolecule or biopharmaceutical and includes any variant, derivative or conjugate designed to enhance permeability, increase lipophilicity, and/or increase hydrophilicity or the like (or reduce immunogenicity and increase stability in the case of a biopharmaceutical such as a peptide, protein, nucleic acid or carbohydrate). The active pharmaceutical agent may alternatively be an amino acid such as, for example, glycine. Glycine is of particular interest given its ability to protect human intestinal Caco-2 and HCT-8 cells against oxidative agents and its ability to reduce the intracellular concentration of reactive oxygen species and its ability to preserve intracellular glutathione concentration. The invention therefore includes a composition of the disclosure comprising glycine. In a related embodiment, the invention provides a composition for use in protecting human intestinal cells against oxidative agents or to reduce the intracellular concentration of reactive oxygen species of such cells or to preserve intracellular glutathione concentration or to prevent/treat inflammatory bowel disease or ischemia-reperfusion (IR) injury. The invention also provides an embodiment comprising a method of maintaining intracellular glutathione content or treatment of inflammatory bowel disease or protection of mammalian intestine against oxidative damage caused by IR injury wherein a composition of the invention is administered to a mammal in need thereof.

The pharmaceutical active may be an immunosuppressive, for example cyclosporine A or tacrolimus or sirolimus or derivatives thereof. The pharmaceutical active may be a hydroxylase inhibitor, for example a propyl hydroxylase inhibitor or an asparaginyl hydroxylase inhibitor. Particular examples are: DMOG, hydralazine, FG-4497 and FG4095.

The pharmaceutical active may modulate oral tolerance. For example, the active entity may be gluten or a gluten derivative. The pharmaceutical active may be an ion channel blocker such as, for example, nimodipine. The pharmaceutical active may be an opioid. For example the pharmaceutical active may be morphine or morphine sulphate or may be an opioid-induced constipation modulator for example a peripheral opioid receptor antagonist such as for example methylnaltrexone, naltrexone or naloxone. The active principle may be an antibody e.g. a polyclonal antibody. Thus the present invention may be used to deliver one or more antibodies to the GI tract, e.g. the colon, to inactivate viruses or bacteria such as, for example, enterotoxigenic *Escherichia coli* (ETEC). The invention relates to a composition comprising such active principles and also to a method of treating viral or bacterial infections of the GI tract by administering such a formulation to a mammal, e.g. a human patient, in need thereof. The present invention may also be used to deliver one or more antibodies e.g. infliximab or natalizumab or bevacizumab to the GI tract, e.g. the colon, for therapeutic or prophylactic benefit e.g. to treat inflammatory bowel disease or prevention or treatment of colo-rectal cancer (CRC). The invention also relates to a composition comprising such active principles and also to a method of preventing or treating inflammatory bowel disease or of preventing or treating CRC by administering such a formulation to a mammal, e.g. a human patient, in need thereof. The present invention may also be used to deliver other types of active principles, especially anti-cancer active principles, such as, for example, tyrosine kinase inhibitors e.g. erlotinib or targeted receptor tyrosine kinase (RTK) inhibitors such as, for example, sunitinib malate, or pyrimidine analogues such as, for example, fluorouracil (5-FU or f5U). The invention relates to a composition comprising such active principles and also to a method of preventing or treating inflammatory bowel disease or CRC by administering such a formulation to a mammal, e.g. a human patient, in need thereof.

Where the active principles are for vaccination, the vaccine may for example be to prevent or treat gastro-intestinal infections including those caused by *Helicobacter pylori, Vibrio cholerae*, enterotoxigenic *Escherichia coli* (ETEC), *Shigella* spp., *Clostridium difficile*, rotaviruses and calici viruses; or respiratory infections including those caused by *Mycoplasma pneumoniae*, influenza virus, and respiratory syncytial virus; and sexually transmitted genital infections including those caused by HIV, *Chlamydia trachomatis, Neisseria gonorrhoeae* and herpes simplex virus. Adjuvants (one or more in admixture) may be chosen for example from the group consisting of α-galactosylceramide (also known as alphaGalCer), chitosan, cholera toxin e.g. rCTB (recombinant B subunit of cholera toxin), *E. coli* heat labile enterotoxin e.g. mLT, oligodeoxynucleotides such as, for example, CpG, monophospholipid (MPL) e.g. MPLA, BCG, saponins including those derived from the soap bark tree (*Quillaja saponaria*) such as, for example, QS21 and QuilA, Poly I:C (polyinosinic:polycytidylic acid or polyinosinic-polycytidylic acid sodium salt), various oils such as, for example, cholesterol-related or cholesterol-derived oils such as, for example, squalene (IUPAC name: (6E,10E,14E,18E)-2,6,10,15,19,23-hexamethyltetracosa-2,6,10,14,18,22-hexaeneoils. Such a vaccine or immuno-modulating composition may optionally also contain one or more emulsifiers e.g. mannide monooleate. If it is desired to utilise both squalene and mannide monooleate as components of the composition, it is possible to introduce both components into the composition of the invention during manufacturing by using a commercially available water-in-oil emulsion which includes squalene and mannide monooleate (Montanide ISA 720 by Seppic Inc, France).

The composition of the invention may also or instead comprise one or more active principle(s) selected from any of the combinations described in the next section (single APIs from this list are contemplated as are any combinations of such single APIs such that for example, the combination described below of an antibiotic susceptible to enzymatic or acidic degradation and a degradative enzyme, is also intended to include a composition according to the invention which comprises an antibiotic susceptible to enzymic or acidic degradation not combined with a degradative enzyme and also a composition according to the invention which comprises a degradative enzyme not combined with an antibiotic susceptible to enzymic or acidic degradation).

The present invention also provides methods of treatment of an animal e.g. fish or mammal e.g. a human, and/or of one or more of the above diseases comprising administering to the animal the composition described herein.

Nourishment, medication or vaccines for non-mammalian animals including fish or other aquatic life forms is also contemplated.

The composition of the invention may be formulated in capsules, suppositories, pessaries or may be used in extracorporeal devices or other health-related e.g. medical or other devices.

Combinations of Active Ingredients

As noted above, more than one active principle may be incorporated in a single mini-bead and/or in distinct populations of mini-beads within a single dosage form, e.g. hardgel capsule. The composition of the invention lends itself to fixed dose combinations of particular drugs.

In one such embodiment the formulation of the invention comprises a methylxanthine and a corticosteroid. The methylxanthine may be selected from theophylline, pentoxifylline, and A802715 and the corticosteroid may be selected from dexamethasone, prednisolone, prednisone and budesonide.

Other preferred fixed dose combinations include:—
- a combination comprising a methylxanthine and an anticancer agent (such as, for example, cisplatin, paclitaxel, daubomycin or vincristine);
- a combination comprising a methylxanthine and a Vitamin A analogue (such as, for example, valproaic acid, valproate or isotretinoin);
- a combination comprising a methylxanthine and a nitric oxide donor such as, for example, nitroprusside, 02-acyl diazenium diolole or NO-NSAIDs such as, for example, NO-aspirin;
- a combination comprising a methylxanthine and a reactive oxygen species scavenger such as, for example, stephenhenanthrine or uvariopsine;
- a combination comprising an immunostimatory agent such as, for example, inosine or other adjuvants and an anticancer agent such as, for example, cisplatin, paclitaxel, daubomycin or vincristine;
- a combination comprising various antiretroviral agents for the treatment of HIV/AIDS, selected from sequinivir, stavudine, ritonivir, lipinavir, amprenevir;
- a combination comprising various antiretroviral agents for the treatment of HIV/AIDS together with immunostimulatory agents;
- a combination for the treatment of malaria comprising Artemisinin-based actives, including artesunate plus sulfadoxine/pyrimethamine or artesunate and amodiaquine;
- a combination for the treatment of tuberculosis comprising isoniazid, rifampin and pyrazinamide;
- a combination for the co-treatment of HIV/AIDS, Malaria and TB, comprised of, from one of the following: HIV: Sequinivir, Stavudine, Ritonivir, Lipinavir, or Amprenevir; Malaria: Sulfadoxine/Primethamine/Artesunate; and Tuberculosis: Isoniazid/Rifampin/Pyrazinamide;
- a combination comprising various cardiovascular agents, selected from one or more of ACE inhibitors, antidiuretics, statins, anticholesterol agents, anti-coagulants, betablockers and anti-oxidants;
- a combination comprising immunomodulators including vaccines, antigens and immunotherapeutic agents with immunostimulatory agents and/or adjuvants;
- a combination comprising a proton pump inhibitor (PPI) [which may be selected from omeprazole, lansoprazole, rabeprazole, esomeprazole, pantoprazole], an anti-H-Pylori antibiotic [which may be selected from metronidazole, tetracycline, clarithromycin, amoxicillin], H-blockers [which may be selected from cimetidine, ranitidine, famotidine, nizatidine] and stomach lining protectants [such as, for example, bismuth subsalicylate], the PPI and H-blockers being released following transit through the stomach, the antibiotic release in the stomach and the stomach lining protectant being released in the stomach;
- a combination comprising agents susceptible to efflux pump activity or metabolism via cytochrome P450 subtypes, including 3A, together with inhibitors of such;
- a combination comprising an antibiotic susceptible to enzymatic degradation and a degradative enzyme, the antibiotic have a controlled release profile in the stomach and small intestine and the enzyme being released in the distal small intestine and colon;
- a combination comprising a narcotic, anti-psychotic or other potentially addictive agent with an antidote or irritant, the former drug classes being released in the stomach and small intestine with the antidote, an innocuous or non-systemically absorbed agent, being released in the colon, the irritant may be irritating when injected but innocuous when taken orally;
- a combination for the treatment of Alzheimer's Disease comprising a cholinesterase inhibitor (such as, for example, donepezil, rivastigmine, galantamine) and a N-Methyl-D-Aspartame (NMDA) antagonist such as, for example, memantine;
- a combination for the treatment of Alzheimer's Disease comprising a cholinesterase inhibitor (such as, for example, donepezil, rivastigmine, galantamine) and one or more from the following classes: vitamins, statins, estrogen, nootrophic agents, *ginkgo biloba*, anti-inflammatory agents, anti-depressants, anti-psychotics, vasodilators, mood stabilizers and calcium channel blockers, including Nimodipine;
- a cholesterol lowering combination comprised of a HMG-CoA inhibitor and a intestinal cholesterol uptake inhibitor;
- a combination for the treatment of diabetes comprising insulin and an insulin sensitizer;
- a combination for the treatment of diabetes comprising insulin and an oral antihyperglycemic agent;
- a combination for the treatment of diabetes comprising insulin and a sulfonylurea agent or metformin;
- a combination for the treatment of diabetes comprising insulin and an oral PTP-1B inhibitor;

- a combination for the treatment of diabetes comprise an oral memetic agent with an appetite suppressant or fat uptake inhibitor such as, for example, orlistat;
- a combination comprising an anti-cancer agents and a potency enhancers, including isoflavanoids, polyphenols and anti-cancer agent derivatives;
- a combination containing a potency enhancer such as, for example, an isoflavanoid and either a heart disease therapy, osteoporosis therapy, autoimmune disease treatment or inflammatory bowel disease treatment;
- a combination containing an opioid (such as, for example, morphine or morphine sulphate) combined with an opioid-induced constipation modulator (for example a peripheral opioid receptor antagonist such as, for example, methylnaltrexone, naltrexone or naloxone;
- a ternary combination containing an opioid and peripheral opioid receptor (as exemplified above) combined with an ion-channel blocker for example a calcium channel blocker (eg nimodipine).
- PUFA (polyunsaturated fatty acid) with other natural extracts, including antioxidants and/or pharmaceutical actives
- diuretics and aldosterone inhibitors with differential release profiles
- an anti-inflammatory agents with a steroid
- an immunosuppressant with acetylsalicylic acid (ASA)
- a methylxanthine with a corticosteroid; e.g. for use in the treatment of chronic obstructive pulmonary disease (COPD) and/or asthma or inflammatory bowel disease (IBD)
- a COX-2 inhibitor with vitamin D.

The present invention also provides methods of treatment of one or more of the above diseases using the composition described herein.

Other Active Excipients

The heading of this section is for convenience only and does not imply strict categorisation. For example, a category, substance or active principle described within this "other active excipients" may also be considered to fall within another section or category in this patent application. One (non-limiting) example is the group of substances known as phospholipids which, according to the invention may be excipients, permeability enhancers or active principles (eg phosphatidylcholine which is useful for instance in the treatment of inflammatory bowel disease).

However, in general terms, the invention foresees incorporation into the composition of one or more of the following substances or categories of substances in addition to the primary active principle. For example, the composition may contain a protectant such as, for example, a proteolytic enzyme inhibitor or a protector against acid degradation or both (eg an alkali for example sodium hydroxide); an adhesive entity such as, for example, a muco- or bio-adhesive; excipients to maximize solubility of active pharmaceutical compound(s); excipients to maximize permeability of the active pharmaceutical compound(s) in the small intestine; an antigen(s) and/or an adjuvant(s) to induce an intestinal mucosal or a systemic immune response.

Regarding permeability enhancement, the typical excipients include but are not limited to sodium caprate, sodium dodecanoate, sodium palmitate, SNAC, chitosan and derivatives thereof, fatty acids, fatty acid esters, polyethers, bile salts, phospholipids, alkyl polyglucosides, hydroxylase inhibitors, antioxidants (eg ascorbic acid) and/or nitric oxide donors, including nitric oxide donor groups covalently attached to various active pharmaceutical ingredients. The preceding list is of particular interest to enhance permeability in the ileum.

To enhance permeability in the colon, typical excipients including, but not limited to sodium caprate, sodium dodecanoate, sodium palmitate, SNAC, chitosan and derivatives thereof, fatty acids, fatty acid esters, polyethers, bile salts, phospholipids, alkyl polyglucosides, hydroxylase inhibitors, antioxidants and/or nitric oxide donors, including nitric oxide donor groups covalently attached to various active pharmaceutical ingredients.

The composition may further comprise excipients to enhance the therapeutic potential of active pharmaceutical agents in the ileum and colon including, but not limited to absorption limiters, essential oils such as, for example, omega 3 oils, natural plant extracts such as, for example, neem, ion-exchange resins, bacteria degradable conjugation linkers such as, for example, azo bonds, polysaccharides such as, for example, amylose, guar gum, pectin, chitosan, inulin, cyclodextrins, chondroitin sulphate, dextrans, guar gum and locust bean gum, nuclear factor kappa B inhibitors, acids such as, for example, fumeric acid, citric acid and others, as well as modifications thereof.

The composition may further comprise excipients or other active pharmaceutical or other ingredients to enhance systemic bioavailability following absorption in the small intestine including efflux pump inhibitors, including, but not limited to PgP pump inhibitors, and metabolism inhibitors, including, but not limited to, cytochrome P450 3A inhibitors.

The composition may further comprise excipients to reduce systemic side effects associated with absorption in the small intestine including, but not limited to, antioxidants, such as, for example, curcuminoids, flavanoids or more specifically including curcumin, beta-carotene, α-tocopherol, ascorbate or lazaroid.

The composition may further or separately comprise antioxidants (such as, for example, ascorbic acid or BHT—butyl hydroxy toluene) taste-masking or photosensitive components or photoprotective components. Antioxidants may be incorporated in the aqueous phase (eg hydrophilic antioxidants) or in the oil phase (eg hydrophobic antioxidants such as, for example, vitamin E) for example up to 1% by weight, preferably between 0.01 and 0.50% by weight, more preferably between 0.10 to 0.20% by weight.

The composition may further or separately include an adhesive to ensure that if desired eg. for the mini-bead embodiment, that the mini-beads remain, or remain for longer, in the gastric environment. Mini-beads according to the invention may also comprise materials facilitating or enabling floating or density reduction e.g. as a means of localising mini-beads in desired GI sites. The invention may also, in the mini-bead embodiment, have the means to swell and/or aggregate in the stomach or other GI site.

Cyclosporine

The composition of the present invention is applicable to a wide range of active principles with a range of industrial applications as described above. Within its pharmaceutical applications, the present invention is particularly suitable for the formulation for oral delivery of low solubility drugs as described above. The following section describes by way of extended example, how the present invention can be applied to one such drug, cyclosporine (also known by its International Non-Proprietary Name of ciclosporin).

Cyclosporines form a class of polypeptides commonly possessing immunosuppressive and anti-inflammatory activity. The most commonly known cyclosporin is cyclosporin-A. Other forms of cyclosporines include cyclosporin-B, -C, -D, and -G and their derivatives. It should be understood that herein the terms "cyclosporin" or "cyclosporins" refers to any of the several cyclosporins, derivatives or prodrugs thereof, or to any mixture of any of the above.

Cyclosporin A, available in soft gelatin capsule or oral suspension form, is indicated for the prevention of organ rejection in kidney, liver and heart transplants, for the treatment of severe active rheumatoid arthritis (RA) and severe recalcitrant plaque psoriasis. Other potential indications include Bechet's disease, anemia, nephrotic syndrome and Graft Versus Host Disease (GVHD), including Gastro-Intestinal Graft Versus Host Disease (GI-GVHD), myasthenia gravis, psoriases etc. Furthermore, a range or other diseases may benefit from treatment with cyclosporin A (Landford et al. (1998) Ann Intern Med; 128: 1021-1028) the entirety of which is incorporated herein by reference.

The present invention also provides methods of treatment of one or more of the above diseases using the composition described herein.

Among other things, the composition of the invention enables successful colonic delivery of active principles. This is of particular interest in the case of cyclosporin formulated in the composition of the invention as mini-beads, particularly when the beads bear a polymeric coat of the sort described elsewhere herein. The coat prevents or limits absorption of cyclosporin in the environment of the upper gastrointestinal tract (GIT) but allows abrupt and/or sustained release into the proximal colon, which is the optimum site for colon-targeted delivery of cyclosporin for certain diseases. Such colon targeting is particularly of value for the treatment of diseases of the colon such as, for example, Crohn's disease, ulcerative colitis, and GVHD, including GI-GVHD. It is particularly preferred to have a composition of the invention adapted to release drug, especially cyclosporin, for absorption from the small intestine (for systemic bioavailability) and in the colon (for local effect) in a single format.

Loading of cyclosporine in the mini-beads of the invention is preferably such that a sufficient quantity of mini-beads can be loaded into a hardgel capsule (size 0 or size 1) to achieve 25 mg of CyA in each size zero capsule.

Process for Making the Composition of the Invention

The reader is notified that it is important to refer to this section in relation to the Examples.

The basic method for making the composition of the invention is to mix a fluid form (preferably a solution) of the polymer (or mixture of polymers) chosen to be the water-soluble polymer matrix material (eg gelatin, gum, alginate etc as described more generally elsewhere herein and in any event optionally in admixture with other components described above) with an oil phase to form an homogeneous fluid emulsion. Taking account of the final composition required (as described elsewhere herein), the oil phase and the aqueous phase may be mixed in a proportion in the range 1:6-10, preferably approximately 1:7 or 1:8. In general, only gentle stirring of the components is required using a magnetic or mechanical system e.g. overhead stirrer as would be familiar to a person skilled in the art to achieve emulsification. Continuous stirring is preferred. Any appropriate laboratory stirring apparatus or industrial scale mixer may be utilized for this purpose for example the Magnetic Stirrer (manufactured by Stuart) or Overhead Stirrer (by KNF or Fisher). It is preferred to set up the equipment in such a way as to minimise evaporation of contents such as, for example, water. In one embodiment of the process of the invention, it is preferred to utilise a closed system for stirring in order to achieve this aim.

In the embodiment where the polymer matrix substantially comprises gelatin with the addition of sorbitol, the aqueous phase of polymer matrix is prepared by adding the appropriate quantities of sorbitol (and surfactant if desired) to water, heating to approximately 60-75° C. until in solution and then adding gelatin although the precise order and timing of addition is not critical. A typical "gelatin solution" comprises 15-25% (preferably 17-18%) gelatin; 75%-85% (preferably 77-82%) of water plus from 1-5% (preferably 1.5 to 3%) sorbitol.

The choice of temperature at which the emulsion is formed depends however on various factors include the temperature lability of the active pharmaceutical ingredient and the amount of plasticiser included in the gelatin, the type of gelatin, as well as other factors. Generally however, the gelatin solution (especially in the case of standard or normal gelatin) is maintained at 60° C.-70° C. to maintain it in a fluid state.

The processing temperature can however be reduced to a desirable target temperature e.g. 37° C. by use of lower melting-point gelatin (or gelatin derivatives or mixtures of gelatins with melting point reducers) or other polymer matrix material such as, for example, sodium alginate for example when the active principle to be incorporated in the composition of the invention is temperature-labile. Alternatively, temperature-labile active principles may be processed at higher temperatures by using appropriate apparatus or machinery which limits the time during which the temperature-labile active principle is in contact with the higher temperature medium. For example, if gelatin droplets are being formed by machine extrusion and immediately cooled e.g. in a cooling bath, additional appropriate inlet tubing can be used to introduce temperature-sensitive active principle into the fluid gelatin solution (and the mixture can be immediately homogenized) very shortly before ejection from a beading nozzle or other droppletting process such that the duration of exposure of the active principle to the higher temperature gelatin is limited so reducing the degree of any heat-dependent degradation of the active principle. This process may use any appropriate device such as, for example, a homogenizer, e.g. a screw homogenizer, in conjunction with an extrusion-type apparatus as described for example in WO 2008/132707 (Sigmoid Pharma) the entirety of which is incorporated herein by reference.

Surfactant, if included, is added to the aqueous phase conveniently at the same time the other components are added e.g. polymer matrix material and plasticiser if included e.g. at the beginning of the processing session. The physical form of the surfactant at the point of introduction into the aqueous phase during preparation may play a role in the ease of manufacture of the composition according to the invention. As such, although liquid surfactants can be employed, it is preferred to utilize a surfactant which is in solid form (eg crystalline or powder) at room temperature, particularly when the aqueous phase comprises gelatin. Surfactant is added in the appropriate amount required to achieve the proportion desired and as described above. In general this leads to presence of surfactant in an amount between 0.8% and 1% (by weight) of the aqueous phase.

Generally, the oil phase need not be heated and active principle and in this case other oil phase components are added at room temperature with stirring until clear. These other components may include a volatile (or non-volatile) solvent in addition to the co-solvent and/or solubilizer if selected. The appropriate amount of oil phase active principle (if any) is added to achieve the target proportion as described elsewhere herein and in the examples. In the case of cyclosporine for example, incorporation of too much CyA (35-40%) in the oil phase can lead to precipitation on mixing with the gelatin solution and 25-27% is a reasonable target if for example a dry weight CyA target of 10% is the objective. Stirring can continue for a few minutes to a few hours, even overnight, depending on the active principle (for example, cyclosporine takes several hours to be fully solubilized). Where it is desired to use or include an oil e.g. a wax oil which is not liquid or fully liquid at room temperature (eg SOLUTOL® or CREMOPHOR® RH40) as the oil phase slight warming e.g. to 40-50° C. is appropriate.

The emulsion is formed by addition of the oil phase to the heated aqueous phase with stirring as described above. The resultant emulsion then has the composition of the solidified mini-beads described above but with water still present.

The emulsion is then poured or introduced into a mould or other vessel or poured onto sheets or between sheets or delivered dropwise (or extruded) into another fluid such that the polymer matrix-containing aqueous phase, on solidification, takes the form of the mould, vessel, sheet or droplet/bead intended. It is preferred to progress to mould-forming e.g. beading without delay.

Alternatively to moulding, specialised machinery can be employed for example to create the hemispherical beads described above (see section above entitled "Shape, Size and Geometry") in which the invention takes the form of hemispherical beads. It is possible to manufacture a single bead made from joining two such hemispheres (ie. a single bead having two distinct halves) by using specialist apparatus in which two tubes through which two different emulsions are flowing, normally of circular cross section, are joined shortly before an extrusion point or nozzle (which may be vibrating) into a single dual lumen tube with a flat wall separating the two emulsion flows and which prevents the two emulsions from coming into contact until the point of extrusion. The cross-section of the joined dual-lumen tube up to the point of extrusion therefore appears as two semicircles. In operation, the two hemispherical emulsion flows combine to form a single, substantially spherical, bead on extrusion such that normal droplets are ejected/extruded for solidification.

Solidification can occur in a variety of ways depending on the polymer of the matrix, for example by changing the temperature around the mould, vessel, sheet, droplet/bead etc or by applying a solidification fluid or hardening solution so that the moulded shape is gelled or solidified. In certain embodiments both temperature change and application of a solidifying fluid or hardening solution are employed together or simultaneously.

In the preferred embodiment in which the composition of the invention takes the form of mini-beads, the mini-beads may be formed for example by dropping the fluid emulsion dropwise into a fluid which effects solidification. Where the viscosity of the emulsion to be beaded reaches a certain point, drop formation becomes more difficult and specialised apparatus is then preferred.

In the case where solidification can be achieved by raising or reducing temperature, the temperature of the solidification fluid can be adapted to achieve solidification at the desired rate. For example, when gelatin is used as the polymer matrix, the solidification fluid is at a lower temperature than the temperature of the emulsion thus causing solidification of the polymer matrix. In this case, the solidification fluid is termed a cooling fluid.

In the case where solidification can be achieved chemically, e.g. by induction of cross-linking on exposure to a component of the solidification fluid, the concentration of such component in the solidification fluid and/or its temperature (or other characteristic or content) can be adjusted to achieve the desired rate and degree of solidification. For example, if alginate is chosen as the polymer matrix, one component of the solidification fluid may be a calcium-containing entity (such as, for example, calcium chloride) able to induce cross-linking of the alginate and consequent solidification. Alternatively, the same or similar calcium-containing entity may be included (eg dispersed) in the aqueous phase of the fluid emulsion prior to beading and triggered to induce cross-linking e.g. by applying a higher or lower pH to a solidification fluid into which droplets of emulsion fall dropwise or are introduced. Such electrostatic cross-linking can be varied as to the resulting characteristics of the mini-bead by control of calcium ion availability (concentration) and other physical conditions (notably temperature). The solidification fluid may be a gas (for example air) or a liquid or both. For example, when gelatin is used as the polymer matrix, the solidification fluid can be initially gaseous (eg droplets passing through cooling air) and then subsequently liquid (eg droplets passing into a cooling liquid). The reverse sequence may also be applied while gaseous or liquid cooling fluids alone may also be used. Alternatively, the fluid may be spray-cooled in which the emulsion is sprayed into a cooling gas to effect solidification.

In the case of gelatin or other water-soluble polymer destined to form the immobilization matrix, it is preferred that the solidification fluid be a non-aqueous liquid (such as, for example, medium chain triglycerides, mineral oil or similar preferably with low HLB to ensure minimal wetting) which can conveniently be placed in a bath (cooling bath) to receive the droplets of emulsion as they solidify to form beads. Use of a non-aqueous liquid allows greater flexibility in choice of the temperature at which cooling is conducted.

Where a liquid cooling bath is employed, it is generally maintained at less than 20° C., preferably maintained in the range 5-15° C., more preferably 8-12° C. when standard gelatin is used as the polymer matrix. If a triglyceride is chosen as the cooling fluid in the cooling bath, a preferred example is MIGLYOL® 810 from Sasol.

If gelatin is selected as the polymer matrix, respect for appropriate temperature ranges ensures solidification of the gelatin at an appropriate rate to avoid destruction e.g. of tertiary protein structure in the case where the active principle is a protein.

If alginate is selected as the polymer matrix, a typical method of making mini-beads involves dropwise addition of a 3% sodium alginate solution in which oil droplets are dispersed as described above into a 4° C. crosslinking bath containing 0.1M calcium chloride to produce calcium alginate (this method can be referred to as "diffusion setting" because the calcium is believed to diffuse into the mini-beads to effect cross-linking or setting). Using a syringe pump, or Inotech machine, droplets can be generated or extruded (eg at 5 mL/h if a pump is used) through a sterile needle or other nozzle (described elsewhere herein) which can be vibrating as discussed elsewhere herein. Airflow of between 15 and 20 L/min through 4.5 mm tubing can be applied downwards over the needle to reduce droplet size if desired. Newly formed mini-beads can then be stirred in the calcium chloride bath for up to an hour. If carrageenan is used as the polymer matrix both salt and reduction in temperature e.g. by dropping into cooling oil may be used to obtain solidification.

An alternative approach when using alginate is internal gelation in which the calcium ions are dispersed in the aqueous phase prior to their activation in order to cause gelation of hydrocolloid particles. For example, this can be achieved by the addition of an inactive form of the ion that will cause crosslinking of the alginate, which is then activated by a change in e.g. pH after sufficient dispersion of the ion is complete (see Glicksman, 1983a; Hoefler, 2004 which are both incorporated herein by reference). This approach is particularly useful where rapid gelation is desired and/or where the diffusion approach may lead to loss of API by diffusion thereof into the crosslinking bath.

Following shape-forming, moulding or beading, the resultant shapes or forms may be washed then dried if appropriate. In the case of mini-beads solidified in a solidification fluid, an optional final step in the method of production described above therefore comprises removal of the solidified mini-beads from the solidification fluid. This may be achieved e.g. by collection in a mesh basket through which the solidification fluid (eg MCT) is drained and the beads retained and is preferably conducted without delay e.g. as soon as the beads have formed or within 5, 10, 15, 20, 25 or 30 minutes of their formation. Excess solidification fluid may then be removed using a centrifuge (or other apparatus or machine adapted to remove excess fluid) followed by drying of the beads to remove water or free water and/or removal of some or all of any additional solvent e.g. ethanol or isopropyl alcohol used to dissolve or facilitate dissolution of the active principle in preceding steps optionally followed by washing (eg using ethyl acetate) and a subsequent "drying" step to remove excess solvent (eg ethyl acetate). Isopropyl alcohol is an example of a solvent which is preferably removed later in processing to reduce residues in the oil or aqueous phase. Drying can be achieved by any suitable process known in the art such as use of a drum drier (eg Freund Drum dryer which may be part of the Spherex equipment train if used) with warm air at between 15° C. and 25° C., preferably around 20° C. leading to evaporation or entrainment of the water by the air. Use of gelatin as the polymer matrix (eg as principal constituent of the aqueous immobilisation phase) in most cases requires a drying step and for mini-beads this is preferably achieved by drying in air as above described. The resultant composition (the composition of the invention) is essentially dry as described in more detail above.

In terms of the way in which emulsion droplets may be formed in the first step of the beading process described above, variations of the above described method are possible including introducing droplets into a variety of solidification fluids.

In general, the mini-beads may be generated by the application of surface tension between the fluid o/w emulsion and an appropriate solidification fluid such as, for example, gas or liquid in order to create the spherical or substantially spherical shape of the ultimate beads.

Alternatively, the mini-beads may be produced through ejection or extrusion of the fluid o/w emulsion through an orifice or nozzle with a certain diameter and optionally subject to selected vibrational frequencies and/or gravitational flow. Examples of machines which may be used are the Freund Spherex, ITAS/Lambo, Globex or Inotech processing equipment. Operation of the Spherex machine manufactured by Freund as may be desired to manufacture mini-beads according to the present invention is described in U.S. Pat. No. 5,882,680 (Freund), the entire contents of which are incorporated herein by reference. It is preferred to select a vibrational frequency in the region of 10-15 RPM although the ultimate choice (and separately the amplitude of vibration selected) depends on the viscosity of the emulsion to be beaded. If the polymer matrix is chosen to solidify at lower temperature, it may be appropriate to maintain the lines to the orifice/nozzle at a certain temperature to maintain the fluidity of the solution.

The Spherex machine (and others) may be adapted to make use of a dual concentric lumen nozzle to ensure simultaneous extrusion of two fluids, the fluid in the inner lumen forming a core and the fluid of the outer lumen forming a capsule. The fluid forming the capsule is solidified according to one of the methods described. It may or may not be desirable for the fluid forming the core to be susceptible of solidification to yield a particular embodiment of the composition of the invention.

The above machinery adapted in this way can be used to manufacture the composition of the invention in the form of a capsule in which the core of the composition is filled with a fluid (a gas or a liquid) as described in the section above entitled "Shape, Size and Geometry" (noting that the core, like the capsular material, may be a composition, albeit optionally a distinct composition, according to the invention ie. susceptible of solidification according to one of the methods described above). A three-lumen nozzle and appropriate tubing may be employed if it is desired to include an intermediate internal layer e.g. internal film layer of non-aqueous material on the inner face of the sphere with the intermediate layer conveniently being solid at room temperature. Thus, in terms of the softness/hardness of successive layers, the composition may for example be described as solid:solid in the case of two layers or solid:solid:solid in the case of 3 layers or liquid/semi-liquid:solid:solid in the case of 3 layers.

The preceding paragraphs describe the formation of uncoated beads. It is a preferred embodiment of the present invention to have coated beads which are described in more detail elsewhere herein. Such coatings may be single or multiple and may be applied in a number of ways (see separate section).

With regard to one of the methods described above (ejection of emulsion through an optionally vibrating nozzle) with two concentric orifices (centre and outer), the outer fluid may form a coat (outside the mini-bead) of e.g. polymeric material (polymeric coating) which may contain an active principle or may impart controlled release characteristics to the mini-bead and the inner layer (core) may be a composition according to the invention. The Spherex machine manufactured by Freund (see U.S. Pat. No. 5,882,680 to Freund) is preferably used (the entire contents of this patent is incorporated herein by reference).

Use of the Spherex machine achieves very high monodispersity. For example, in a typical 100 g, batch 97 g of mini-beads were between 1.4 to 2 mm diameter or between 1 and 2 mm. Desired size ranges can be achieved by methods known in the art for rejecting/screening different sized particles. For example, it is possible to reject/screen out the larger/smaller beads by passing a batch first through e.g. a 2 mm mesh and subsequently through a 1.4 mm mesh.

The 1.4 to 2 mm diameter range is a good size if it is desired to coat the mini-beads (if smaller, the spray of the coating machine may bypass the mini-bead; if too large hard, the beads may be harder to fluidise which is necessary to achieve consistent coating).

The mini-beads are preferably internally (ie. cross-sectionally) homogeneous ie. monolithic although processing conditions may be varied for example by altering the temperature of the fluid emulsion, the solidification fluid and the concentration of components in these fluids and the time allowed for certain processing steps to occur including drying. Although not currently preferred, such variations may be applied in the case of mini-bead manufacture to achieve heterogeneity such as, for example, a harder skin and softer core with less than complete immobilization of oil droplets towards the core as opposed to the surface of the bead. Larger (eg non-beaded) forms or shapes of the composition according to the invention may particularly be engineered to embody such heterogeneity. However, it is currently preferred to have internally homogenous compositions according to the invention and within the mini-bead embodiment, this can be favoured by conducting the beading/dropletting using a homogeneous medium eg. a well dispersed emulsion. Such homogeneity in the emulsion to be beaded can help avoid the drying conditions affecting symmetry.

Coating

The composition of the invention may be used for a number of applications as discussed elsewhere herein. When used for oral delivery of active principles, the principles may be advantageous released immediately (immediate release profile) or be released after some delay and/or over an extended period (delayed and/or extended release profile). For immediate release, the mini-beads may be uncoated or coated enterically to protect against stomach acid for immediate release in the small intestine.

Alternatively, if controlled release is desired (ie. delayed, extended or site-targeted release etc), or if media-independent release is desired, it is possible, according to the invention to apply a coat to the mini-beads. Application of the appropriate coat may, for example if colonic release is required, allow for say less than 10% of the active principle to be dissolved (in dissolution medium) at 4 hours and then a burst (sudden release) towards a maximum dissolution (approaching 100%) in the subsequent 24 hours. Many alternative target profiles are possible and this example is purely for illustration.

Thus according to one embodiment of the present invention, the composition is in the form of mini-spheres at least some of which bear a coat (ie. are coated) in order to control release of active principle from the mini-bead. In one embodiment, the coat is a film and in another embodiment, it is a membrane. The coat, film or membrane comprises one or more substances preferably of a polymeric nature (eg methacrylates etc; polysaccharides etc as described in more detail below) or combination of more than one such substance, optionally including other excipients or active principles, such as, for example, plasticizers, described e.g. in the sections above on active principles. Preferred plasticizers, if they are used, include hydrophilic plasticizers for example triethyl citrate (TEC) which is particularly preferred when using the EUDRAGIT® family of polymers as coatings as described below. Another preferred plasticiser, described in more detail below in relation to coating with ethyl cellulose, is DBS. Alternative or additional optionally included excipients are glidants. A glidant is a substance that is added to a powder or other medium to improve its flowability. A typical glidant is talc which is preferred when using the EUDRAGIT® family of polymers as coatings.

In the case of combinations of polymers, combinations may be selected in order to achieve the desired delay (or other change) in the release of the drug and/or poration of the coating and/or exposure of the mini-bead within the coating to allow egress of drug and/or dissolution of the immobilization matrix. In one embodiment, two types of polymers are combined into the same polymeric material, or provided as separate coats that are applied to the mini-beads.

It has previously been stated that the composition of the invention may comprise more than one population of mini-beads. Within the coating embodiment, the differences between populations may lie in the coat ie. two (or more) populations of mini-beads may differ in a number of respects one of which is the coating.

The coat may be applied as described below and may vary as to thickness and density. The amount of coat is defined by the additional weight added to (gained by) the dried composition (eg mini-bead) of the invention. Weight gain is preferably in the range 0.1% to 50%, preferably from 1% to 15% of the dry weight of the bead, more preferably in the range 3% to 10% or in the range 5-12% or in the range 8-12%.

The polymeric coating material may comprise methacrylic acid co-polymers, ammonio methacrylate co-polymers, or mixtures thereof Methacrylic acid co-polymers such as, for example, EUDRAGIT® S and EUDRAGIT® L (Evonik) are particularly suitable. These polymers are gastroresistant and enterosoluble polymers. Their polymer films are insoluble in pure water and diluted acids. They may dissolve at higher pHs, depending on their content of carboxylic acid. EUDRAGIT® S and EUDRAGIT® L can be used as single components in the polymer coating or in combination in any ratio. By using a combination of the polymers, the polymeric material can exhibit solubility at a variety of pH levels, e.g. between the pHs at which EUDRAGIT® L and EUDRAGIT® S are separately soluble.

The trademark "EUDRAGIT" is used hereinafter to refer to methacrylic acid copolymers, in particular those sold under the EUDRAGIT® by Evonik.

The coating can comprise a polymeric material comprising a major proportion (e.g., greater than 50% of the total polymeric coating content) of at least one pharmaceutically acceptable water-soluble polymer, and optionally a minor proportion (e.g., less than 50% of the total polymeric content) of at least one pharmaceutically acceptable water insoluble polymer. Alternatively, the membrane coating can comprise a polymeric material comprising a major proportion (e.g., greater than 50% of the total polymeric content) of at least one pharmaceutically acceptable water insoluble polymer, and optionally a minor proportion (e.g., less than 50% of the total polymeric content) of at least one pharmaceutically acceptable water-soluble polymer.

Ammonio methacrylate co-polymers such as, for example, EUDRAGIT® RS and EUDRAGIT® RL (Evonik) are suitable for use in the present invention. These polymers are insoluble in pure water, dilute acids, buffer solutions, and/or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCl) groups in the polymer. For example, those polymers having EA:MMA:TAMC1 ratios of 1:2:0.2 (EUDRAGIT® RL) are more permeable than those with ratios of 1:2:0.1 (EUDRAGIT® RS). Polymers of EUDRAGIT® RL are insoluble polymers of high permeability. Polymers of EUDRAGIT® RS are insoluble films of low permeability. A particularly preferred diffusion-controlled pH-independent polymer in this family is RS 30 D which is a copolymer of ethyl acrylate, methyl methacrylate and a low content of methacrylic acid ester with quaternary ammonium groups present as salts to make the polymer permeable. RS 30 D is available as an aqueous dispersion.

The amino methacrylate co-polymers can be combined in any desired ratio, and the ratio can be modified to modify the rate of drug release. For example, a ratio of EUDRAGIT® RS: EUDRAGIT® RL of 90:10 can be used. Alternatively, the ratio of EUDRAGIT® RS: EUDRAGIT® RL can be about 100:0 to about 80:20, or about 100:0 to about 90:10, or any ratio in between. In such formulations, the less permeable polymer EUDRAGIT® RS generally comprises the majority of the polymeric material with the more soluble RL, when it dissolves, permitting gaps to be formed through which solutes can come into contact with the mini-bead allowing pre-dissolved pharmaceutical actives to escape in a controlled manner.

The amino methacrylate co-polymers can be combined with the methacrylic acid co-polymers within the polymeric material in order to achieve the desired delay in the release of the drug and/or poration of the coating and/or exposure of the mini-bead within the coating to allow egress of drug and/or dissolution of the immobilization or water-soluble polymer matrix. Ratios of ammonio methacrylate co-polymer (e.g., EUDRAGIT® RS) to methacrylic acid co-polymer in the range of about 99:1 to about 20:80 can be used. The two types of polymers can also be combined into the same polymeric material, or provided as separate coats that are applied to the mini-beads.

EUDRAGIT®FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. A further example is EUDRAGIT® L 30D-55 which is an aqueous dispersion of anionic polymers with methacrylic acid as a functional group. It is available as a 30% aqueous dispersion.

In addition to the EUDRAGIT® polymers described above, a number of other such copolymers can be used to control drug release. These include methacrylate ester co-polymers such as, for example, the EUDRAGIT® NE and EUDRAGIT® NM ranges. Further information on the EUDRAGIT® polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114 the entirety of which is incorporated herein by reference.

Several derivatives of hydroxypropyl methylcellulose (HPMC) also exhibit pH dependent solubility and may be used in the invention for coating. These include hydroxypropyl methylcellulose phthalate (HPMCP), which rapidly dissolves in the upper intestinal tract and hydroxypropyl methylcellulose acetate succinate (HPMCAS) in which the presence of ionizable carboxyl groups causes the polymer to solubilize at high pH (>5.5 for the LF grade and >6.8 for the HF grade). These polymers are commercially available from Shin-Etsu Chemical Co. Ltd. As with other polymers described herein as useful for coatings, HPMC and derivatives may be combined with other polymers e.g. EUDRAGIT® RL-30 D.

It is particularly preferred according to the invention to use a polymeric coating substance which is pH-independent in its dissolution profile and/or in its ability to release active principles incorporated in the mini-beads of the invention. Examples have already been given (e.g., EUDRAGIT® RS and RL). Another example of a pH-independent polymeric coating substance is ethylcellulose, in particular a dispersion of ethylcellulose in a sub-micron to micron particle size range, e.g. from about 0.1 to 10 microns in size, homogeneously suspended in water with the aid of an emulsification agent, e.g. ammonium oleate. The ethylcellulose dispersion may optionally and preferably contain a plasticizer, for example dibutyl sebacate (DBS) or medium chain triglycerides. Such ethylcellulose dispersions may, for example, be manufactured according to U.S. Pat. No. 4,502,888, which is incorporated herein by reference. One such ethylcellulose dispersion suitable for use in the present invention and available commercially is marketed under the trademark SURELEASE®, by COLORCON® of West Point, Pa. USA. In this marketed product, the ethylcellulose particles are, e.g., blended with oleic acid and a plasticizer, then optionally extruded and melted. The molten plasticized ethylcellulose is then directly emulsified, for example in ammoniated water optionally in a high shear mixing device, e.g. under pressure. Ammonium oleate can be formed in situ, for instance to stabilize and form the dispersion of plasticized ethylcellulose particles. Additional purified water can then be added to achieve the final solids content. See also U.S. Pat. No. 4,123,403, which is incorporated herein by reference.

The trademark "SURELEASE®" is used hereinafter to refer to ethylcellulose coating materials, for example a dispersion of ethylcellulose in a sub-micron to micron particle size range, e.g. from about 0.1 to 10 microns in size, homogeneously suspended in water with the aid of an emulsification agent, e.g. ammonium oleate. In particular, the trademark "SURELEASE®" is used herein to refer to the product marketed by COLORCON® under the SURELEASE® trademark.

SURELEASE® dispersion is an example of a combination of film-forming polymer, plasticizer and stabilizers which may be used as a coating to adjust rates of active principle release with reproducible profiles that are relatively insensitive to pH. The principal means of drug release is by diffusion through the SURELEASE® dispersion membrane and is directly controlled by film thickness. Use of SURELEASE® is particularly preferred and it is possible to increase or decrease the quantity of SURELEASE® applied as coating in order to modify the dissolution of the coated mini-bead. Unless otherwise stipulated, use of the term "SURELEASE®" may apply to SURELEASE® E-7-19020, E-7-19030, E-7-19040 or E-7-19050. E-7-19020 comprises ethylcellulose blended with oleic acid and dibutyl sebacate, then extruded and melted. The molten plasticized ethylcellulose is then directly emulsified in ammoniated water in a high shear mixing device under pressure. Ammonium oleate is formed in situ to stabilize and form the dispersion of plasticized ethylcellulose particles. Additional purified water is then added to achieve the final solids content. E-7-19030 additionally comprises colloidal anhydrous silica dispersed into the material. E-7-19040 is like E-7-19020 except that it comprises medium chain triglycerides instead of dibutyl sebacate. E-7-19050 derives from blending ethylcellulose with oleic acid before melting and extrusion. The molten plasticized ethylcellulose is then directly emulsified in ammoniated water in a high shear mixing device under pressure. Ammonium oleate is formed in situ to stabilize and form the dispersion of plasticized ethylcellulose particles. However, E-7-19040 is preferred.

The invention also contemplates using combinations of SURELEASE® with other coating components, for example sodium alginate, e.g. sodium alginate available under the trade name Nutrateric®.

In addition to the EUDRAGIT® and SURELEASE® polymers discussed above, other enteric, or pH-dependent, polymers can be used. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as, for example, sodium lauryl sulfate and polysorbates, organic acids such as, for example, acetic acid, adipic acid, citric acid, fumaric acid, glutaric acid, malic acid, succinic acid, and tartaric acid, sugars such as, for example, dextrose, fructose, glucose, lactose, and sucrose, sugar alcohols such as, for example, lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566 all of which are incorporated herein by reference in their entirety.

As noted above, SURELEASE® is a particularly preferred polymer coating owing to its pH-independent dissolution character. However, the inventors/applicants have found that it is difficult to select the appropriate amount (weight gain) of SURELEASE® to achieve optimal dissolution. It has been found that too much SURELEASE® leads to incomplete (or over slow) dissolution while too little leads to over fast dissolution.

The inventors/applicants have now surprisingly found in a particular embodiment that by addition to SURELEASE® of a second polymer (eg a polysaccharide, especially a heteropolysaccharide) which is normally degraded by bacterial enzymes (and optionally or alternatively by pancreatic or other relevant enzymes) unexpectedly resolves this problem and provides flexibility in modulating the amount of polymer added to the mini-beads of the invention in order to achieve optimal dissolution profiles.

The invention therefore also provides a novel coating for compositions (whether of the invention or not) intended to release their active payload in the colon which is a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon. Such polysaccharides include chondroitin sulphate, pectin, dextran, guar gum and amylase, chitosan etc and derivatives of any of the foregoing. Chitosan is particularly preferred in connection with obtaining a colon-specific release profile. The invention also includes a composition comprising a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon; the composition may include a liquid vehicle, e.g. water.

The use of polysaccharides by themselves for coating purposes has been tried with limited success. Most of the non-starch polysaccharides suffer from the drawback of lacking good film forming properties. Also, they tend to swell in the GI tract and become porous, resulting in the early release of the drug. Even amorphous amylose, which is resistant to degradation by pancreatic alpha amylase but capable of degradation by colonic bacterial enzymes has the disadvantage of swelling in aqueous media although this can be controlled by incorporating insoluble polymers like, ethyl cellulose and acrylates into the amylose film. Amylose however is not water-soluble and although water-soluble polysaccharides are not excluded, the present inventors have found that use of a water-soluble polysaccharide (WSP) susceptible of bacterial enzymic degradation brings particularly advantageous results when used as a coating in accordance with this embodiment of the present invention. A particularly preferred polysaccharide in this embodiment of the present invention is pectin. Various kinds of pectin may be used including pectin of different grades available ie with differing degrees of methylation (DM), i.e. percentage of carbonyl groups esterified with methanol, for example pectins with a DM of more than 50%, known as High Methoxy (HM) Pectins or Low Methoxy (LM) pectins, or a pectin combination comprising an HM pectin and an LM pectin. It is also possible in this embodiment to use pectins having various degrees of acetylation (DAc). Taken together, the DM and DAc or the degree of substitution is known as Degree of Esterification (DE). Pectins of various DE's may be used according to the invention. As an alternative to pectin, sodium alginate may be used as a polysaccharide according to an embodiment of the invention. However, other embodiments may conveniently include amylose and/or starch which contains amylose. Various grades of starch, containing different percentages of amylose may be used including for example HYLON® V (National Starch Food Innovation) which has an amylose percentage of 56% or HYLON® VII which has an amylose percentage of 70%. The remaining percentage is amylopectin. The polysaccharides pectin, amylose and sodium alginate are particularly preferred for achieving colon delivery ie for compositions intended to release active principles in the colon.

It has been found that pectin can act as a former of pores in the coating otherwise provided by ethylcellulose (preferably SURELEASE®). By "pores" is not meant shaft-like holes from the surface to the core of the mini-bead, rather areas of weakness or absence of coating occuring stochastically on and within the coating of the invention.

Pore formers have been described before in connection with SURELEASE® (see e.g. US 2005/0220878) but in relation to "gastro-insoluble" substances such as, for example, alginate.

According to a particular embodiment of the invention, where the water-soluble polysaccharide (WSP) is pectin, the proportion of SURELEASE® to pectin is ideally in the range 90:10 to 99:1, preferably, 95:5 to 99:1, more preferably 98:2 to 99:1.

In this particularly preferred combination (SURELEASE®+WSP e.g. pectin) the weight gain and ratio between SURELEASE® and WSP can be varied to refine the behaviour of the coating and the composition of the invention when it bears such a coat. Thus to the inventors/applicant's surprise, the advantages of this preferred combination of coating polymers were further pronounced by selecting a weight gain in the range 0 to 30% (preferably 5 to 10%) and a SURELEASE® to pectin ratio in the range 95:5 to 99.5:0.5 preferably 97:3 to 99:1 inclusive. Particularly favoured weight gains using SURELEASE® are those in the range 5-12% or in the range 8-12%.

Although the focus above has been on extending and/or sustaining release of active principles from mini-beads according to the invention, also contemplated are uncoated or simple enteric coated mini-beads providing early, small intestinal API release with sufficient enteric coating merely to protect the minibeads from dissolution in the stomach.

It is preferred to dry the mini-beads before they are coated with a suitable polymeric coat (as described in more detail above/below). It is also preferred, in certain embodiments to apply a first coat before applying a second. In general the first coat and the second coat may be of the same or different materials and be chosen from any of the classes of coating material described herein. In specific embodiments, the first coat optionally protects the core (bead) from interaction with the second coat and/or prevents leaching of bead contents into the second coat. For example, the first coat may be made of a mixture of hypromellose, titanium dioxide and polyethylene glycol and the second (outer) coat made of the SURELEASE®-pectin mixture described above. If it is desired for the first coat to use a mixture of hypromellose, titanium dioxide and polyethylene glycol, commercial products corresponding to such mixtures are available including Opadry White, a product commercialised by COLORCON®. More generally, various products commercialised under the trade name Opadry and Opadry II. Further nonlimiting examples include Opadry YS-1-7706-G white, Opadry Yellow 03B92357, Opadry Blue 03B90842). These compositions are available as dry film coating compositions that can be diluted in water shortly before use. Opadry and Opadry II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Suitable OPADRY or OPADRY II formulations may comprise a plasticizer and one or more of maltodextrin, and polydextrose (including but not limited to a) triacetin and polydextrose or maltodextrin or lactose, or b) polyethylene glycol and polydextrose or maltodextrin). Particularly preferred commercial products are Opadry White (HPMC/HPC-based) and Opadry II White (PVA/PEG-based). Alternative (non-Opadry) products for initial protective coats include polyvinyl alcohol-polyethylene glycol graft copolymers such as is available commercially under the name Kollicoat IR and methyl metacrylate ammonium-based copolymers such as are available commercially under the name EUDRAGIT® E. Another preferred example is low molecular weight HPMC. The optional inner coat is applied in the same manner as is the outer (or sole) coat (or coating layer).

The coating process can be carried out by any suitable means such as, for example, by use of a coating machine which applies a solution of a polymer coat (as described above in particular) to the mini-beads. Polymers for coating are either provided by the manufacturer in ready-made solutions for direct use or can be made up before use following manufacturers' instructions.

Appropriate coating machines are known to persons skilled in the art and include, for example, a perforated pan or fluidized-based system for example the GLATT, Vector (eg CF 360 EX), ACCELACOTA, Diosna, O'Hara and/or HICOATER processing equipment. Most preferred is the MFL/01 Fluid Bed Coater (Freund) used in the "Bottom Spray" configuration.

Typical coating conditions are as follows:

| Process Prameter | Values |
| --- | --- |
| Fluidising airflow (m3/h) | 20-60 (preferably 30-60) |
| Inlet air temperature (° C.) | 20-65 |
| Exhaust air temperature (° C.) | 38-42 |
| Product temperature (° C.) | 38-42 |
| Atomizing air pressure (bar) | Up to 1.4 e.g. 0.8-1.2 |
| Spray rate (g/min) | 2-10 and 3-25 RPM |

Whether as part of the polymeric coat or independently thereof, the mini-beads of the invention may be coated with additional drug layers using methods conventional in the art of pharmaceutical science (such as for example using coating machines as just described) to produce a composition having one or more layer(s), each layer containing one or more active pharmaceutical or other ingredient/excipient as described elsewhere herein. Drug layering means the deposition of at least one or successive layers of drug entities from solution, suspension or dry powder on nuclei e.g. minibeads as described herein. Drug layering includes solution/suspension layering, powder layering and powder drug layering. In solution/suspension layering, drug particles are dissolved or suspended in a binding liquid. In powder layering, complete dissolution does not occur, due to low liquid saturation, irrespective of the solubility of the active agent in the binding liquid. In powder drug layering, a binder solution is first sprayed onto previously prepared inert seeds e.g. minibeads as described herein, followed by the addition of powder. Conventional pan coaters may be used as described above for polymer coating although modified forms of pan coaters are preferred including fluidised-bed and centrifugal rotary granulators. Examples of suitable granulators include the Rotor granulator. (Glatt), the Rotor-processor (Aeromatic), the Spir-a-Flow (Freund) and the CF-granulator (Freund). The use of mini-beads as seeds for drug layering according to the present invention is superior to using traditional non-pareils as initial substrates in the preparation of pellets by a drug layering process. One reason is the optimal size of the mini-beads of the current invention. Another reason is that sucrose, the main component of traditional non-pareils, has well-known drawbacks including harmful effects on diabetics and potential cariogenicity. According to the prior art, microcrystalline cellulose (MCC) has also been tested as a substrate for drug layering although the inventors/applicants are not aware of successful use of MCC for the preparation of initial cores/beads in a centrifugal granulating process as may be used in embodiments of the present invention. Thus in one embodiment, the invention provides a process for the manufacture of drug-coated pellets comprising using the mini-beads described herein as seeds or as non-pareils (i.e. instead of non-pareils) on which the drug is coated. In a related embodiment, a composition of the invention comprises a mini-bead of the disclosure coated with one or more drug layers. Another embodiment is a process of enhancing the solubility of poorly water-soluble active principles by using one or more of the above described methods of drug layering, including spray-drying-based processes. The polymeric coat, described in detail above, may or may not be applied to a drug-layered mini-bead. However, if desired, it may be applied after such drug layering. In applying a drug layer, the drug to be layered onto the mini-bead may optionally first be admixed with appropriate excipients such as, for example, binders as described elsewhere herein. A particularly preferred binder in this context is polyvinyl pyrrolidone (also spelt polyvinylpyrrolidone and also known as PVP or povidone). PVPs of various K-values may be used. The K-value of PVP is a function of its average molecular weight, the degree of polymerization, and the intrinsic viscosity. It is particularly preferred to use PVP K-32, Up to 5% of the dry weight of the composition of the invention in this embodiment may be made up of such binders. Approximately 1% or less is preferred. Other suitable binders which may be used in drug-layering include gelatin, carboxymethyl cellulose, hydroxypropyl methylcellulose and hydrolysed starches e.g. maltodextrins. Compositions embodying drug layering may also optionally be coated with a polymer coating, or include a polymer layer, to control release as described more generally above including the option to include the same or a different active principle in this polymer coat.

The invention therefore includes a layered bead or minibead comprising
- a core comprising, or consisting of, a water-soluble polymer matrix material in which are dispersed droplets of oil, the core comprising an active principle; and
- a layer surrounding the core and comprising an active principle, which may be the same as or different from the active principle comprised in the core.

The layered bead or minibead may have a plurality of layers, e.g. 2, 3, 4 or 5 layers, comprising an active principle, wherein the active principle of each layer is selected independently from the active principle of each other layer. In one embodiment, each layer comprises the same active principle as each other layer; in another embodiment, no two layers comprise the same active principle. The term "active principle" in this paragraph embraces both a single active entity and a combination of active entities. The layered bead or minibead may comprise one or more polymer layers, to control release as described more generally above. Such a polymer layer may contain an active principle and therefore constitute a drug layer as well as a release control layer. Alternatively, a polymer layer may be free of active principle. A polymer layer, whether or not it contains an active principle, may be located between the core and a drug layer outside the polymer layer, or between two drug layers, or may form an outer layer.

The invention therefore includes a layered bead or minibead comprising
- a core comprising, or consisting of, a water-soluble polymer matrix material in which are dispersed droplets of oil, the core comprising an active principle;
- an active principle layer surrounding the core and comprising an active principle, which may be the same as or different from the active principle comprised in the core; and
- a polymer layer free of active principle.

The polymer layer may be located between the core and the active principle layer. The polymer layer may be located externally of the active principle layer. The layered bead or minibead may comprise a plurality of active principle layers and, additionally or alternatively, it may comprise a plurality of polymer layers. In some embodiments, there is at least one active principle layer which comprises a release-controlling polymer. In some embodiments, the outermost layer comprises a release-controlling polymer, which may contain an active principle or, in another implementation, be free of active principle.

The optionally coated mini-beads of the invention may be formulated directly following their manufacture in the ways described above. In an alternative embodiment, it may be desired to impart different properties to the mini-beads and/or to a final solid dosage product. One way of achieving this according to the invention is through granulation eg. to improve the flow of powder mixtures of mini-beads with other components as e.g. described above in relation to binders. Granules of intact or broken mini-beads may be obtained by adding liquids (eg binder or solvent solutions) and effecting a granulating step as described in the prior art. Larger quantities of granulating liquid produce a narrower particle size range and coarser and harder granules, i.e. the proportion of fine granulate particles decreases. The optimal quantity of liquid needed to get a given particle size may be chosen in order to minimise batch-to-batch variations. According to this embodiment, wet granulation is used to improve flow, compressibility, bio-availability, homogeneity, electrostatic properties, and stability of the composition of the invention presented as a solid dosage form. The particle size of the granulate is determined by the quantity and feeding rate of granulating liquid. Wet granulation may be used to improve flow, compressibility, bio-availability, and homogeneity of low dose blends, electrostatic properties of powders, and stability of dosage forms. A wet granulation process according to this embodiment may employ low or high shear mixing devices in which a low viscosity liquid (preferably water) is added to a powder blend containing binder previously dry mixed with the rest of the formulation including mini-beads. Alternative granulation approaches which may be utilized include high-shear, extrusion and conventional wet granulation.

Examples

As noted in the introduction, it is desirable to have a solid composition which presents fluid active ingredients in a way which can be easily and directly manufactured and shaped while retaining the benefits of fluids. Individual examples below show, in one or more embodiments of the invention, a solid composition comprising a fluid which meets this object.

For successful oral administration e.g. in the fields of active pharmaceuticals, the active principle must be in solution for local effect or systemic absorption, it must be usually be stabilized before release and it must be permeable, it must ideally demonstrate ease and cost of manufacture including scaleability, reproducibility and shelf-life and e.g. deliverable and/or releasable in the colon. As noted in the introduction above, "stabilized before release" includes protection from degrading stomach acids, proteolytic enzymes etc. Individual examples below show, in one or more embodiments of the invention, that it is possible to resolve multiple such problems simultaneously in a single oral dosage form.

The above described formulation issues are often greater for water-insoluble or poorly water-soluble active entities. Individual examples below show, in one or more embodiments of the invention, that it is possible to provide a dosage form which resolves some or all of these issues for such difficult-to-solubilize molecules or active agents or principles.

As discussed, it can be desirable for an active principle to be in solution ie. a dissolved state and maintaining that dissolved state until release thus avoiding the need for dissolution in vivo (a "pre-dissolved" active principle) and to maintain the solubilized state and prevent release until the target release zone (eg colon) is reached. Individual examples below show, in one or more embodiments of the invention, e.g. on the basis of in vitro dissolution that it is possible to solve this problem.

A further specific need within the general requirement for the active principle to be in solution is the maintenance of the formulated active principle in a dissolved state as well as immediately after dispersion/egress from its carrier or matrix. Individual examples below show, in one or more embodiments of the invention, that it is possible to address this requirement.

Individual examples below show, in one or more embodiments of the invention, that it is also possible to obtain a dosage form from which substantially all of the active principle is solubilized and dispersed (without necessarily maintaining dissolution) in vitro in a compendial medium (without adding surfactant to the medium) following a standard USP/EP/JP etc method.

In relation to the problem of how to formulate active principles in a dissolved state when it is also desired to coat such dosage forms with polymers intended to modify drug release characteristics without the coating preventing full, sufficient or predictable release of active principle in the gastro-intestinal tract (GIT) and without excess variability in release, the individual examples below show, in one or more embodiments of the invention, that it is possible (eg on the basis of in vitro experiments) to obtain an oral dosage form which achieves full, substantial or sufficient release of active principle in the GIT and/or with appropriate inter- and intra-patient variability in a clinical setting or in vitro surrogate thereof.

For hydrophobic active principles, it is particularly desirable to increase water solubility or miscibility as well as to increase stability and reduce volatility and to control the availability of the active principle, particularly the bioavailability. At the same time it is desirable to avoid or reduce manufacturing and quality control complexity. Individual examples below show, in one or more embodiments of the invention, that it is possible in a simple way to obtain an oral drug formulation which addresses one or more of these goals especially an increase in water solubility/miscibility; increase in stability; reduction in volatility; control of bioavailability.

As mentioned in the introduction, in drug delivery systems having distinct compartments within a single administrative form, it can be difficult to achieve controlled e.g. simultaneous release of multiple drugs contained in a single form. Individual examples below show, in one or more embodiments of the invention, that it is possible to obtain oral delivery formulations which address these challenges.

As noted previously, it can be desirable but difficult to formulate liquid, emulsified or pre-solubilized active principles with surfactants. Individual examples below show, in one or more embodiments of the invention, that it is possible to obtain oral delivery formulations which allow the incorporation of surfactants (or sufficient quantities of surfactants) therein.

As discussed, peptide drugs such as, for example, for example, cyclosporin, calcitonin, niacin or lacticin, are difficult to administer orally or formulate for oral administration because of the unique physicochemical properties of peptides including molecular size, poor solubility, short plasma half-life, requirement for specialised mechanisms for membrane transport and susceptibility to enzymatic breakdown (intestinal, pre-systemic and systemic). Individual examples below show, in one or more embodiments of the invention, that it is possible to provide a solution to these problems. For example, the invention provides, in one embodiment, a composition comprising a peptide drug susceptible of enzymic, acidic or hydrolytic breakdown wherein the composition prevents or reduces such breakdown from occurring. This may be physicochemical e.g. barrier means inherent to the composition of the invention or chemical e.g. base/alkali (eg NaOH) or acid (eg citric acid) to create a protective milieu around the peptide drug.

Moreover, individual examples below show, in one or more embodiments of the invention, that it is possible to address the challenges and problems of formulating ciclosporin A for delivery to the colon and/or to sections of the GIT from where absorption of cyclosporin is limited.

Individual examples below also show, in one or more embodiments of the invention, that it is possible to provide, e.g. on the basis of in vitro experiments, a composition comprising an active principle for release in the colon with release prevented in the more proximal GI tract; to avoid or reduce the variability of release profile resulting from pure pH-based and time-based systems; to avoid or reduce variability between healthy and diseased bowel; and with a particle size which prevents or reduces delay in passing the pylorus and/or reduces residence time in the ileo-caecal junction.

Individual examples below also show, in one or more embodiments of the invention, that it is possible to obtain an oral dosage form which can be manufactured relatively easily.

EXAMPLES

In the following examples 1 to 13 inclusive, mini-beads are produced as generally described. Unless otherwise specified, the units used to describe the compositions are provided in weight 0/00 (per thousand).

One important test conducted on the resultant mini-beads is the content assay. This test relates to the active principle and establishes the proportion of active principle which has successfully been incorporated in the mini-bead following its manufacture. A representative sample of the batch is used to carry out this analysis. Typically a given amount of the sample is weighed out and extracted in a suitable diluent. Standard techniques and methodologies are utilized as would be known to persons skilled in the art e.g. in relation to established Pharmacopoeia. For example, in the case of CyA, the diluent used is acetonitrile/purified water/methanol/ortho-phosphoric acid in the following ratio 64%/32%/3.5%/0.5%. The extraction is carried out by sample sonication for 2 hours, at ambient temperature, followed by filtration and dilution to a predetermined concentration, equal to that of the reference standard against which the sample is quantified. Once the sample has been prepared, it is analysed via HPLC, whereby the sample is passed through a steel column packed with silica and then detected via UV absorbance at a preset wavelength. This generates a chromatogram, which delivers a peak and a peak area. The peak areas are then used to calculate the % active ingredient present in the sample.

It is ideal to achieve 100% incorporation in the content assay although in practice lower levels of incorporation are acceptable (note that occasional measurement error can lead to figures slightly above 100%). The content assay (sometimes referred to as CA) is also therefore one measure of the "quality" of the formulation in the sense that a formulation which fails to incorporate sufficient active principle is of lower quality than one able to incorporate a higher proportion. The present inventors/applicants have used this measure along with others to define the parameters of the composition of the invention for example the type of components the composition may comprise and in which quantities.

Another test conducted on the examples below is the dissolution test which garners a dissolution profile for the composition of the invention. Typically this test is conducted using a U.S.P. Type II apparatus (paddles) at 37 degree C. and 50 rpm, in pH 6.8 buffer. Various time points are recorded e.g. proportion dissolved in the period from start (0 hours) up to 4 hours, then up to 6 hours, then up to 8 hours etc. In general (but this depends on specific objectives), the longer the time the experiment is continued, the more active principle is dissolved with each successive proportion being a cumulative assessment of dissolution at that time point. It is useful if 100% dissolution is achieved but the time in which that is achieved is also important and depends on the therapeutic objectives for the formulation. Diminishing (or a sudden drop in) dissolution over time signifies precipitation. Full dissolution is usually more important for quality control than for prediction of in-vivo performance.

Example 1

Cyclosporine A (CyA) beads were made as described above (please also refer to Example 48 for additional experimental detail). The resulting CyA bead formulation had the following composition (mg/g, on a dry basis):

| | |
|---|---|
| Cyclosporin A | 92.87 |
| Gelatin | 551.93 |
| D-Sorbitol | 74.61 |
| TRANSCUTOL® | 144.95 |
| CREMOPHOR® EL | 75.43 |
| LABRAFAC® Lipophile 1349 WL | 60.21 |

CyA at 25% (w/w); was dissolved in the oil phase which was made from 4 parts oil (LABRAFAC® Lipophile 1349 WL), 5 parts CREMOPHOR® EL and 10 parts TRANSCUTOL®. The resulting oil phase was afterwards added to the gelatin solution in a 1/8 weight ratio. After drying, beads were robust and not sticky. The content assay gave nearly 95% of CyA incorporation. The dissolution profile in water was:

| | |
|---|---|
| 0.5 h | 62.16 |
| 1 h | 61.49 |
| 3 h | 61.05 |
| 4 h | 46.65 |
| 6 h | 34.26 |

Example 2

The following composition was prepared as before:

| | |
|---|---|
| Cyclosporin A | 182.07 |
| Gelatin | 544.39 |
| TRANSCUTOL® | 158.98 |
| CREMOPHOR® EL | 54.63 |
| LABRAFAC® Lipophile 1349 WL | 59.93 |

No D-Sorbitol was added in the gelatin solution, since TRANSCUTOL® and CREMOPHOR® EL also act as plasticizers. In the oil phase, the weight ratio between TRANSCUTOL® and CREMOPHOR® EL was increased from 2:1 (Example 1) to 3:1 it was possible to obtain an oil phase containing 40% of CyA. Some CyA precipitation was observed when the oil phase and gelatin solution were mixed;. The content assay was 91%. The release profile was:

| | |
|---|---|
| 0.5 h | 12.03 |
| 1 h | 21.52 |
| 3 h | 29.71 |
| 4 h | 31.22 |
| 6 h | 32.83 |

Example 3

The beads of this example were prepared by dissolving CyA in EtOH (ethanol), then adding CREMOPHOR® EL and MCT oil, and finally letting EtOH evaporate overnight. The resulting CyA solution was very viscous, and so it remained also after mixing with the gelatin solution. Example 3 had the following composition:

| | |
|---|---|
| CyA | 139.83 |
| CREMOPHOR® EL | 111.30 |
| LABRAFAC® Lipophile 1394 WL | 89.22 |
| Gelatin | 560.12 |
| D-Sorbitol | 75.82 |
| SDS | 23.71 |

Content assay was 48% with the following release profile:

| | |
|---|---|
| 0 | 0 |
| 1 h | 48.31 |
| 2 h | 50.26 |
| 3 h | 50.59 |
| 6 h | 51.13 |

Example 4

In this example, CyA was dissolved in EtOH, then a mixture of TWEEN® 80 and LABRAFIL® M 1944 CS was added; EtOH was evaporated overnight. The composition was as follows:

| | |
|---|---|
| CyA | 145.30 |
| Gelatin | 539.39 |
| D-Sorbitol | 74.11 |
| SDS | 23.04 |
| LABRAFIL® M 1944 CS | 126.70 |
| TWEEN® 80 | 91.46 |

The content assay was 75% and dissolution profile was:

| | |
|---|---|
| 0 | 0 |
| 0.5 h | 15.79 |
| 1 h | 22.13 |
| 2 h | 23.58 |
| 3 h | 23.52 |

Example 5

In this example, CyA was again dissolved in EtOH (evaporated overnight), while the other components of the oily phase were LABRAFIL® M 1944 CS and Epax 6000 TG (omega-3 oil). No problem was encountered during preparation.

| | |
|---|---|
| CyA | 83.56 |
| Gelatin | 538.46 |
| D-Sorbitol | 72.66 |
| SDS | 22.96 |

| | |
|---|---|
| LABRAFIL® M 1944 CS | 141.39 |
| Epax 6000 TG | 140.97 |

CyA incorporation was 92.5% and the release profile was:

| | |
|---|---|
| 0 | 0 |
| 0.5 h | 90.17 |
| 1 h | 104.55 |
| 2 h | 103.48 |
| 3 h | 108.24 |

The CyA loading was 8% w/w.

Example 6

Compared to Example 1, CyA loading was increased by decreasing the weight ratio between the oily phase and gelatin solution from 1:8 to 1:7.

| | |
|---|---|
| CyA | 103.23 |
| Gelatin | 504.16 |
| D-Sorbitol | 58.21 |
| SDS | 23.00 |
| TRANSCUTOL® HP | 160.91 |
| CREMOPHOR® EL | 84.98 |
| LABRAFAC® Lipophile 1349 WL | 65.51 |

This example 6 contained 91% of theoretical CyA, and showed the following release profile:

| | |
|---|---|
| 0 | 0 |
| 0.5 h | 79.60 |
| 1 h | 88.04 |
| 2 h | 90.22 |
| 3 h | 89.76 |
| 6 h | 86.28 |

Example 7

Similar to example 5, the following composition was manufactured. The content assay result was 87%:

| | |
|---|---|
| CyA | 82.85 |
| Gelatin | 538.67 |
| D-Sorbitol | 72.86 |
| SDS | 23.08 |
| Epax 6000 TG | 140.85 |
| LABRAFIL® M 1944 CS | 141.69 |

Example 8

Similar to example 7, the following composition was manufactured. The content assay result was 75%:

| | |
|---|---|
| CyA | 86.80 |
| Gelatin | 610.08 |
| SDS | 25.41 |
| Epax 6000 TG | 138.33 |
| LABRAFIL® M 1944 CS | 139.36 |

Example 9

Similar to example 8, the following composition was manufactured. The content assay result was 79%:

| | |
|---|---|
| CyA | 74.80 |
| Gelatin | 600.63 |
| SDS | 25.28 |
| Epax 6000 TG | 149.91 |
| LABRAFIL® M 1944 CS | 149.93 |

Example 10

Similar to example 9, the following composition was manufactured. It was possible to increase the CyA concentration and incorporation in the beads. Issues during manufacturing included viscosity of solution and shape of beads, which were long-tailed. The content assay result was 97%:

| | |
|---|---|
| CyA | 106.59 |
| Gelatin | 605.06 |
| SDS | 24.36 |
| Epax 6000 TG | 128.58 |
| Labrafil M1944 CS | 135.39 |

| Dissolution | |
|---|---|
| 0 | 0 |
| 0.5 h | 93.93 |
| 1 h | 94.55 |
| 2 h | 96.13 |
| 3 h | 95.7 |
| 4 h | 94.15 |

Example 11

The beads of this example are similar to the beads of Example 6. The CyA content was increased to 11% by excluding D-Sorbitol from the formulation. The content assay data was 98% and dissolution profile was:

| | |
|---|---|
| CyA | 109.40 |
| Gelatin | 537.20 |
| SDS | 24.51 |
| TRANSCUTOL® HP | 169.85 |
| CREMOPHOR® EL | 89.82 |
| LABRAFAC® Lipophile 1349 WL | 69.22 |

| dissolution | |
|---|---|
| 0 | 0 |
| 0.5 h | 77.32 |
| 1 h | 77.21 |
| 2 h | 79.91 |
| 3 h | 83.07 |
| 4 h | 81.05 |

Example 12

Similar to Example 11, this Example contained approximately 12.5% CyA, a lower content of gelatin and a higher content of SDS. Content assay was 99.5% and dissolution profile:

| | |
|---|---|
| CyA | 124.30 |
| Gelatin | 507.76 |
| SDS | 50.26 |
| TRANSCUTOL® HP | 172.02 |
| LABRAFAC® Lipophile 1349 WL | 59.26 |
| CREMOPHOR® EL | 86.33 |

| Dissolution | |
|---|---|
| 0 | 0.00 |
| 0.5 h | 39.80 |
| 1 h | 46.96 |
| 2 h | 56.89 |
| 3 h | 56.75 |
| 4 h | 56.08 |

Spherex CyA Examples

The following examples (Examples 14 to 17) were made using the Spherex machine described above equipped with a single lumen nozzle with a diameter of 3 mm. Unless otherwise specified, the mini-beads were produced through ejection of the fluid o/w emulsion through the single orifice (nozzle) subject to vibration at a frequency of 15-40 Hz. The temperature of the emulsion was in the range 60° C. to 80° C. and dropped into a cooling bath of medium chain triglyceride oil kept at around 10° C. See also Example 49 for additional experimental detail relevant to these examples.

Example 14

This example had a content assay of 98% with the following composition and dissolution profile:

| | |
|---|---|
| CYA | 116.26 |
| LABRAFAC® Lipophile 1349 WL | 61.90 |
| CREMOPHOR® EL | 88.42 |
| SDS | 30.84 |
| Gelatin | 525.48 |
| TRANSCUTOL® HP | 177.10 |

| Dissolution | |
|---|---|
| 0 | 0.00 |
| 0.5 h | 37.43 |
| 1 h | 41.74 |
| 2 h | 41.57 |
| 3 h | 41.77 |
| 4 h | 41.92 |

It was observed that it was difficult to obtain good beads (spherical shape, size uniformity).

Example 15

This example was similar to Example 14 but with the addition of D-sorbitol. The beads had improved morphology and dissolution profile compared to those of Example 14 and achieved a content assay of 100%:

| | |
|---|---|
| CYA | 109.91 |
| Migyol 810 | 46.78 |
| CREMOPHOR® EL | 93.98 |
| SDS | 25.21 |
| Gelatin | 499.16 |
| TRANSCUTOL® HP | 167.37 |
| D-Sorbitol | 57.59 |

| Dissolution | |
|---|---|
| 0 | 0.00 |
| 0.5 h | 72.89 |
| 1 h | 79.63 |
| 2 h | 78.78 |
| 3 h | 78.30 |

Example 16

This example is similar to Example 15 but with a different oil phase resulting in a different weight ratio between MCT oil and CREMOPHOR® EL. The content assay was 95% and the composition and dissolution profile were as follows:

| | |
|---|---|
| CYA | 110.39 |
| LABRAFAC® Lipophile 1349 WL | 58.83 |
| CREMOPHOR® EL | 83.77 |
| SDS | 23.53 |
| Gelatin | 498.13 |
| D-Sorbitol | 57.46 |
| TRANSCUTOL® HP | 167.88 |

| Dissolution | |
|---|---|
| 0 | 0.00 |
| 0.5 h | 53.32 |
| 1 h | 51.91 |
| 2 h | 53.64 |
| 3 h | 53.26 |
| 4 h | 54.98 |

Example 17

This example is similar to that of Example 15 the only difference being the increased SDS content. In this run, more than 90% of beads were in the range 1.4-2.0 mm. The composition and release profile were as follows:

| | |
|---|---|
| Cyclosporin A | 107.91 |
| MIGLYOL® 810 | 46.06 |
| CREMOPHOR® EL | 92.40 |
| SDS | 40.21 |
| Gelatin | 492.38 |
| TRANSCUTOL® HP | 164.36 |
| D-Sorbitol | 56.69 |

| Dissolution | |
|---|---|
| 0 | 0.00 |
| 0.5 h | 64.80 |
| 1 h | 71.48 |
| 3 h | 73.79 |
| 4 h | 78.04 |

Tacrolimus Examples

Beads exemplified in Examples 18 to 23 were made in the manner of Examples 1 to 13.

Example 18a

In this example, the oil phase was made from LABRAFIL® M 1944CS (40% w/w), TWEEN® 80 (30% w/w) and TRANSCUTOL® P (30% w/w). The oil phase weight ratio was 1:8 and this yielded good quality beads (beads prepared with the same oil phase to gelatin solution ratio of 1:6 weight ratio were sticky). Drug incorporation was 93.5% and the composition and release profile were as follows:

| Composition | mg/g |
|---|---|
| Tacrolimus | 11.10 |
| Gelatin | 506.80 |
| D-Sorbitol | 70.64 |
| Ascorbic Acid* | 48.40 |
| TRANSCUTOL® | 108.77 |
| TWEEN® 80 | 106.19 |
| LABRAFIL® M 1944 CS | 148.09 |

*Ascorbic Acid is used as antioxidant.

| Dissolution (two media) | | |
|---|---|---|
| Time (hrs) | Water | 0.15% SDS(aq.) |
| 0 | 0 | 0 |
| 1 | 47.22 | 73.26 |
| 3 | 49.00 | 76.76 |
| 4 | 44.39 | 68.86 |
| 6 | 50.91 | 70.20 |
| 8 | 53.52 | 71.02 |
| 12 | 66.75 | 70.15 |
| 16 | 52.67 | 79.90 |

Example 18b

In this Example, TRANSCUTOL® was not used and the API was dissolved in EtOH, then LABRAFIL® M 1944 CS and TWEEN® 80 were added, finally EtOH was evaporated overnight. Gelatin solution was added keeping the 1:8 weight ratio. The content assay was 81.55% while the composition and dissolution profile were as follows:

| Composition | mg/g |
|---|---|
| Tacrolimus | 15.78 |
| Gelatin | 496.88 |
| D-Sorbitol | 67.33 |
| Ascorbic Acid | 47.35 |
| TWEEN® 80 | 146.26 |
| LABRAFIL® M 1944 CS | 202.66 |

| Dissolution in three media: | | | |
|---|---|---|---|
| Time (h) | Water | 0.15% SDS | 0.3% SDS |
| 1 | 40.72 | 66.4 | 78.73 |
| 3 | 42.24 | 61.01 | 72.46 |
| 4 | 44.23 | 59.95 | 79.39 |
| 6 | 45.59 | 64.24 | 77.96 |

Example 19

In this Example it was decided to use TRANSCUTOL® HP as solubilizer and SDS as surfactant in the gelatin solution. The content assay was 98% while the composition and dissolution profile were:

| Composition | mg/g |
|---|---|
| Tacrolimus | 14.57 |
| Gelatin | 496.03 |
| D-Sorbitol | 67.60 |
| SDS | 23.70 |
| Ascorbic Acid | 47.33 |
| TRANSCUTOL® | 104.87 |
| TWEEN® 80 | 105.45 |
| LABRAFIL® M 1944 CS | 140.45 |

| Time (hrs) | Water | 0.15% SDS | 0.3% SDS |
|---|---|---|---|
| 1 | 67.68 | no sampling | 91.09 |
| 2 | 67.71 | 67.35 | 90.98 |
| 3 | 66.10 | 69.63 | 90.71 |
| 6 | 63.50 | 63.86 | 90.15 |

Example 20

In this example, HPMC E 100 (100 is the viscosity in mPa/s of a 1% HPMC solution) was introduced as crystallization inhibitor. More vigorous stirring was required as HPMC is not fully soluble in gelatin solution. Content assay was 102% and composition and dissolution profiles as follows:

| Tacrolimus | 14.95 |
|---|---|
| Gelatin | 506.10 |
| TRANSCUTOL® HP | 107.06 |
| LABRAFIL® M 1944 CS | 142.77 |
| TWEEN® 80 | 106.60 |
| SDS | 23.95 |
| HPMC | 29.76 |
| D-Sorbitol | 68.82 |

| Dissolution profile: | | | |
|---|---|---|---|
| | DIH20 | 0.15% SDS | 0.3% SDS |
| 0 h | 0 | 0 | 0 |
| 1 h | 66.06 | 84.03 | 98.35 |
| 3 h | 68.55 | 84.70 | 98.54 |
| 6 h | 68.55 | 82.60 | 94.85 |
| 12 h | 56.68 | 81.16 | 94.49 |
| 18 h | 56.65 | 83.25 | 98.19 |
| 24 h | 55.67 | 84.09 | 97.86 |

Example 21

This example is of a formulation very similar to that of Example 20 except that the gelatin solution/oil phase ratio was decreased to 6.5:1. The CA was 96.5% with the composition and dissolution profiles as follows:

| Tacrolimus | 16.76 |
|---|---|
| Gelatin | 469.90 |

-continued

| | |
|---|---|
| TRANSCUTOL® HP | 120.02 |
| LABRAFIL® M 1944 CS | 160.05 |
| TWEEN® 80 | 119.51 |
| SDS | 22.23 |
| HPMC | 27.63 |
| D-Sorbitol | 63.89 | dissolution profile:

| | DIH20 | 0.15% SDS | 0.3% SDS |
|---|---|---|---|
| 0 h | 0 | 0 | 0 |
| 1 h | 50.20 | 73.23 | 96.32 |
| 3 h | 44.24 | 72.17 | 96.59 |
| 6 h | 53.54 | 71.52 | 97.23 |
| 12 h | 55.10 | 79.45 | 98.39 |
| 18 h | 55.70 | 80.16 | 98.80 |
| 24 h | 56.45 | 79.90 | 96.28 |

Example 22

In this Example, the SDS content was increased to 4% (on dry basis) and dissolutions were conducted in media containing increasing amount of HPMC. C.A.=110%.

| | |
|---|---|
| Tacrolimus | 14.81 |
| Gelatin | 497.67 |
| Transcutol HP | 105.72 |
| Labrafil M 1944 CS | 141.18 |
| Tween 80 | 105.64 |
| SDS | 40.00 |
| HPMC | 27.39 |
| D-Sorbitol | 67.59 |

| | DIH20 | 0.25% HPMC | 0.50% HPMC | 0.75% HPMC |
|---|---|---|---|---|
| 0 h | 0 | 0 | 0 | 0 |
| 1 h | 31.27 | 42.13 | 53.72 | 24.17 |
| 4 h | 58.03 | 43.99 | 47.28 | 49.38 |
| 8 h | 57.50 | 31.38 | 43.97 | 61.08 |
| 12 h | 61.00 | 32.39 | 39.19 | 54.10 |
| 18 h | 56.29 | 47.28 | 35.41 | 48.69 |
| 24 h | 58.65 | 49.14 | 44.72 | 46.83 |

Example 23

In this Example, as in Example 22, the SDS content was increased to 4% (on dry basis) and dissolutions were conducted in media containing increasing amount of HPMC. C.A.=107%.

| | |
|---|---|
| Tacrolimus | 15.27 |
| Gelatin | 510.82 |
| TRANSCUTOL® HP | 108.97 |
| LABRAFIL® M 1944 CS | 145.51 |
| TWEEN® 80 | 108.89 |
| SDS | 41.75 |
| D-Sorbitol | 68.78 |

| | DIH20 | 0.25% HPMC | 0.50% HPMC | 0.75% HPMC |
|---|---|---|---|---|
| 0 h | 0 | 0 | 0 | 0 |
| 1 h | 32.19 | 63.76 | 18.23 | 35.06 |
| 4 h | 59.57 | 50.91 | 39.45 | 49.99 |
| 8 h | 45.73 | 39.68 | 40.26 | 48.91 |
| 12 h | 57.68 | 48.78 | 50.03 | 48.83 |
| 18 h | 62.30 | 52.13 | 60.10 | 47.12 |
| 24 h | 67.49 | 53.46 | 57.52 | 54.55 |

Coated CyA Beads

The following Examples illustrate the embodiment of the invention in which the mini-beads bear a coat (are coated). In all this group of examples, coating is conducted following the manufacturer's instructions using the MFL/01 Fluid Bed Coater (Freund) used in the "Bottom Spray" configuration. Typical coating conditions are as described in the table above of process parameters. Where SURELEASE® is used, this refers to SURELEASE® E-7-19040.

Example 24

The mini-beads of Example 1 were coated with 5.82% SURELEASE® and dissolution were carried out in 3 media (water, 0.15% SDS in water, 0.30% SDS in water) and gave the following results:

| | H2O | 0.15% SDS | 0.3% SDS |
|---|---|---|---|
| 0.5 h | 0.00 | 2.50 | 1.62 |
| 1 h | 0.00 | 1.60 | 1.38 |
| 3 h | 0.00 | 1.81 | 29.15 |
| 4 h | 0.00 | 1.84 | 44.12 |
| 6 h | 1.27 | 2.46 | 65.49 |
| 12 h | 9.73 | 4.18 | 88.59 |
| 18 h | 16.82 | 6.11 | 98.11 |
| 24 h | 22.69 | 7.77 | 101.35 |

Example 25

The mini-beads of Example 1 were coated to get a 10% w/g but as expected release profile was slower (data not shown).

Example 26

The mini-beads of Example 6 were coated with 2.43% SURELEASE® and gave the following dissolution profile:

| | H2O | 0.15% SDS | 0.3% SDS |
|---|---|---|---|
| 0 h | 0.00 | 0.00 | 0.00 |
| 1 h | 7.77 | 25.73 | 45.03 |
| 3 h | 34.85 | 58.39 | 85.75 |
| 4 h | 43.61 | 67.23 | 89.75 |
| 6 h | 55.24 | 78.30 | 90.02 |
| 12 h | 67.09 | 89.55 | 91.76 |
| 18 h | 20.92 | 90.40 | 92.47 |
| 24 h | 11.22 | 91.80 | 93.32 |

In water, the decrease of CyA release between 12 and 24 hours was due to API precipitation over time. In order to estimate the actual amount of drug dissolved, the drug content in the coating shell after the dissolution (ghosts) was analyzed and found to be 11.5% ie. nearly 90% of CyA was released in water after 24 hours.

Example 27

Coated beads of Example 26 were further coated to get 4.89% SURELEASE® weight gain overall coating to give the following dissolution profiles:

|  | H2O | 0.15% SDS | 0.3% SDS |
|---|---|---|---|
| 0 h | 0.00 | 0.00 | 0.00 |
| 1 h | 6.23 | 2.10 | 3.92 |
| 3 h | 14.51 | 12.70 | 38.10 |
| 4 h | 23.97 | 23.07 | 48.87 |
| 6 h | 38.23 | 36.53 | 63.30 |
| 12 h | 57.33 | 61.17 | 85.69 |
| 18 h | 30.18 | 76.78 | 91.33 |
| 24 h | 13.65 | 84.35 | 93.08 |
| GHOST SAMPLE | 12.55% | | |

Example 28

The beads of Example 11 were coated with 3.5% weight gain SURELEASE®) and gave the following release profile:

|  | H2O | 0.15% SDS | 0.3% SDS |
|---|---|---|---|
| 0 h | 0.00 | 0.00 | 0.00 |
| 1 h | 0.00 | 4.01 | 8.93 |
| 3 h | 36.69 | 45.10 | 83.04 |
| 4 h | 52.61 | 62.44 | 91.12 |
| 6 h | 69.33 | 80.54 | 92.77 |
| 12 h | 82.19 | 92.74 | 93.66 |
| 18 h | 70.12 | 93.50 | 94.17 |
| 24 h | 26.50 | 94.00 | 95.33 |
| GHOST SAMPLE | 4.46% | | |

Example 29

The beads of Example 11 were coated with 5.45% weight gain SURELEASE® and gave the following release profile:

|  | H2O | 0.15% SDS | 0.3% SDS |
|---|---|---|---|
| 0 h | 0 | 0 | 0 |
| 1 h | 0 | 0 | 1.09 |
| 3 h | 11.22 | 8.48 | 54.35 |
| 4 h | 24.48 | 17.06 | 75.38 |
| 6 h | 43.24 | 30.22 | 89.88 |
| 12 h | 68.85 | 52.79 | 92.93 |
| 18 h | 71.23 | 60.34 | 93.66 |
| 24 h | 73.37 | 65.61 | 94.25 |
| GHOST SAMPLE | 5.68% | 26.08% | |

Example 30

The mini-beads of Example 14 were coated with 2.44% weight gain SURELEASE® and gave the following dissolution profile:

|  | H2O | 0.15% SDS | 0.3% SDS |
|---|---|---|---|
| 0 h | 0.00 | 0.00 | 0.00 |
| 1 h | 14.02 | 51.46 | 86.14 |
| 3 h | 27.42 | 69.39 | 96.26 |
| 4 h | 30.18 | 70.37 | 96.32 |
| 6 h | 32.08 | 70.34 | 96.54 |
| 12 h | 30.01 | 71.27 | 97.90 |
| 18 h | 22.48 | 71.65 | 98.84 |
| 24 h | 15.22 | 72.71 | 99.12 |
| ghost anal. | 12.68% | 30.87% | |

Example 31

The beads of Example 16 were coated with 4.5% weight gain SURELEASE® and gave the following dissolution profiles:

|  | H2O | 0.15% SDS | 0.3% SDS |
|---|---|---|---|
| 0 | 0.00 | 0.00 | 0.00 |
| 1 | 2.64 | 3.78 | 4.92 |
| 3 | 8.93 | 13.48 | 36.21 |
| 4 | 13.17 | 17.43 | 45.15 |
| 6 | 21.51 | 23.32 | 58.87 |
| 12 | 33.60 | 34.75 | 83.07 |
| 18 | 15.59 | 40.72 | 90.16 |
| 24 | 7.08 | 44.32 | 93.21 |
| ghost | 38.60% | 48.01% | |

Example 32

Beads similar to those of Example 16 were coated with 6.55% weight gain SURELEASE® to give the following dissolution profile:

| 37.5 mg | H2O | 0.15% SDS | 0.3% SDS |
|---|---|---|---|
| 0 | 0.00 | 0.00 | 0.00 |
| 1 | 1.02 | 1.36 | 2.83 |
| 3 | 3.43 | 9.11 | 30.13 |
| 4 | 5.94 | 13.01 | 37.39 |
| 6 | 10.91 | 19.24 | 48.18 |
| 12 | 12.14 | 33.00 | 70.88 |
| 18 | 8.72 | 41.77 | 81.42 |
| 24 | 7.50 | 47.11 | 84.88 |
| ghost | 48.41 | 43.62 | |

Example 33

The beads of Example 17 were coated with 3.6% weight gain SURELEASE® to give the following dissolution profile:

|  | H2O | 0.15% SDS |
|---|---|---|
| 0 h | 0.00 | 0.00 |
| 1 h | 36.50 | 67.11 |
| 3 h | 65.64 | 92.00 |
| 4 h | 70.23 | 93.70 |
| 6 h | 62.61 | 94.64 |
| 12 h | 28.65 | 95.04 |
| 16 h | 11.94 | 94.56 |

|  | H2O | 0.15% SDS |
|---|---|---|
| 18 h | 9.66 | 94.50 |
| 20 h | 7.50 | 94.76 |
| 24 h | 6.86 | 95.08 |
| GHOST | 12.86% |  |

Example 34

The beads of Example 17 were coated with 5.4% weight gain SURELEASE® to give the following dissolution profile:

| (5.4% SURELEASE®) | | |
|---|---|---|
| 37.5 mg | H2O | 0.15% SDS |
| 0 h | 0.00 | 0.00 |
| 1 h | 3.40 | 13.37 |
| 3 h | 21.98 | 45.52 |
| 4 h | 26.07 | 53.54 |
| 6 h | 24.15 | 64.08 |
| 12 h | 13.11 | 80.17 |
| 16 h | 8.69 | 82.81 |
| 18 h | 7.47 | 82.27 |
| 20 h | 6.64 | 81.04 |
| 24 h | 8.74 | 78.47 |
| Ghost | 32.82% | 13.76% |

Example 35

The beads of Example 17 were coated with 8.7% weight gain SURELEASE® to give the following dissolution profile:

| (8.7% SURELEASE®) | | |
|---|---|---|
| 37.5 mg | H2O | 0.15% SDS |
| 0 h | 0.00 | 0.00 |
| 1 h | 1.86 | 4.28 |
| 3 h | 6.01 | 24.54 |
| 4 h | 9.82 | 29.86 |
| 6 h | 14.23 | 40.15 |
| 12 h | 10.84 | 48.73 |
| 16 h | 7.69 | 49.98 |
| 18 h | 6.27 | 49.74 |
| 20 h | 5.19 | 49.64 |
| 24 h | 5.22 | 49.70 |
| Ghost | 48.27 | 42.80 |

Example 36

The beads of Example 17 were coated with NUTRATERIC®, that is an association of SURELEASE® and Na Alginate, at 4.6% weight gain using SURELEASE®/Alginate in a ratio of 85/15. This gave the following dissolution profiles: (4.6% NUTRATERIC® 85/15)

|  | H2O | 0.15% SDS |
|---|---|---|
| 0 h | 0 | 0 |
| 1 h | 36.33 | 91.88 |
| 3 h | 40.6 | 96.27 |
| 4 h | 39.95 | 96.3 |
| 6 h | 37.15 | 96.68 |
| 12 h | 23.42 | 96.83 |
| 16 h | 14.39 | 96.17 |
| 18 h | 11.23 | 95.46 |
| 20 h | 9.03 | 95.29 |
| 24 h | 6.82 | 94.77 |
| GHOST | 22.40 | 1.86 |

Example 37

The beads of Example 17 were coated with NUTRATERIC®, that is an association of SURELEASE® and Na Alginate, at 11.3% weight gain using SURELEASE®/Alginate in a ratio of 85/15. This gave the following dissolution profiles:

| (11.3% NUTRATERIC® 85/15) | | |
|---|---|---|
|  | H2O | 0.15% SDS |
| 0 h | 0 | 0 |
| 1 h | 30.95 | 90.13 |
| 3 h | 38.79 | 95.04 |
| 4 h | 38.81 | 95.35 |
| 6 h | 37.61 | 95.51 |
| 12 h | 22.81 | 96.21 |
| 16 h | 14.18 | 96.47 |
| 18 h | 10.86 | 96.1 |
| 20 h | 8.64 | 96.11 |
| 24 h | 6.39 | 96.14 |
| GHOST | 23.33 | 2.23 |

Example 38

The beads of Example 17 were coated with NUTRATERIC®, that is an association of SURELEASE® and Na Alginate, at 6.2% weight gain using SURELEASE®/Alginate in a ratio of 95/5. This gave the following dissolution profiles:

| (6.2% NUTRATERIC® 95/5) | | |
|---|---|---|
|  | H2O | 0.15% SDS |
| 0 h | 0 | 0 |
| 1 h | 22.76 | 52.23 |
| 3 h | 38.71 | 77.13 |
| 4 h | 40.09 | 84.44 |
| 6 h | 37.64 | 92.43 |
| 12 h | 12.3 | 93.94 |
| 16 h | 8.23 | 92.98 |
| 18 h | 7.72 | 92.36 |
| 20 h | 7.47 | 92.36 |
| 24 h | 7.47 | 92.36 |
| GHOST | 36.33 | — |

Example 39

The beads of Example 17 were coated with NUTRATERIC® (SURELEASE® and Na Alginate) at 11.2% weight gain using SURELEASE®/Alginate in a ratio of 95/5. This gave the following dissolution profiles:

| (11.2% NUTRATERIC® 95/5) | | |
|---|---|---|
| 37.5 mg | H2O | 0.15% SDS |
| 0 h | 0 | 0 |
| 1 h | 5.93 | 31.39 |
| 3 h | 24.42 | 61 |
| 4 h | 25.44 | 66.75 |
| 6 h | 21.94 | 74.28 |
| 12 h | 11.13 | 83.24 |
| 16 h | 7.5 | 83.24 |
| 18 h | 6.51 | 83.5 |
| 20 h | 5.64 | 82.8 |
| 24 h | 5.65 | 82.8 |
| GHOST | 43.66 | — |

Example 40

The mini-beads of Example 17 were coated with FS 30 D (EUDRAGIT® polymer based on methyl acrylate) for a 22% weight gain to give the following dissolution profiles:

| (22% FS 30 D) | | | |
|---|---|---|---|
| 0 | 0.00 | 0.00 | 0.00 |
| 1 | 10.46 | 10.92 | 11.44 |
| 2 | 33.87 | 32.39 | 32.89 |
| 3 | 46.34 | 55.81 | 54.16 |
| 4 | 52.86 | 66.98 | 66.07 |
| 6 | 55.35 | 73.72 | 78.28 |
| 12 | 46.71 | 80.17 | 85.35 |
| 16 | 42.48 | 81.31 | 86.72 |
| 18 | 41.62 | 81.64 | 87.19 |
| 20 | 40.86 | 81.79 | 87.68 |
| 24 | 39.89 | 81.76 | 89.04 |
| ghost | 14.37% | 5.91% | 1.18% |

*First 2 hours were carried in PBS (pH = 7.4), then samples were transferred in water, 0.15% SDS and 0.3% SDS.

Example 41

The mini-beads of Example 17 were coated with RS 30 D (EUDRAGIT® polymer based on methyl acrylate) for a 5% weight gain to give the following dissolution profiles:

| (5% RS 30 D) | | |
|---|---|---|
| | H2O | 0.15% SDS |
| 0 h | 0 | 0 |
| 1 h | 0.91 | 2.23 |
| 3 h | 13.1 | 7.66 |
| 4 h | 22.53 | 10.97 |
| 6 h | 34.21 | 16.47 |
| 12 h | 35.04 | 28.32 |
| 16 h | 17.13 | 35.37 |
| 18 h | 15.26 | 38.06 |
| 20 h | 12.31 | 40.17 |
| 24 h | 13.42 | 43.52 |
| GHOST | 31.42 | 63.14 |

Example 42

The mini-beads of Example 17 were coated with a combination of SURELEASE® and Pectin in a ratio of 98/2 for a total weight gain of 16.57% to give the following dissolution profile in three media: deionised water with pectinase, phosphate-buffered saline and Hanks buffer solution with SDS and pectinase:

| (16.57% SURELEASE®/Pectin 98/2) | | | |
|---|---|---|---|
| | DiH2O c. 0.5% Pectinase | PBS pH 7.4 | 50/50 Hanks/H2O; 0.1% SDS; 0.5% Pectinase |
| 0 h | 0.00 | 0.00 | 0.00 |
| 1 h | 4.81 | 7.88 | 8.75 |
| 3 h | 17.07 | 37.55 | 40.00 |
| 4 h | 19.52 | 46.15 | 48.90 |
| 6 h | 19.26 | 56.90 | 62.15 |
| 12 h | 12.35 | 71.13 | 79.03 |
| 16 h | 10.45 | 73.61 | 84.29 |
| 18 h | 11.06 | 72.40 | 86.03 |
| 20 h | 14.80 | 65.29 | 88.32 |
| 24 h | 35.37 | 54.74 | 83.66 |
| GHOST | 28.11% | 14.36% | 11.23% |

Dissolution was carried out with the addition of pectinase

Example 43

The mini-beads of Example 17 were coated with a combination of SURELEASE® and Pectin in a ratio of 98/2 for a total weight gain of 22.5% to give the following dissolution profile in a medium varied over the course of the dissolution experiment (middle column is time in hours) starting with hydrochloric acid and switching to phosphate-acetate (PA) buffer initially with SDS:

| (22.5% SURELEASE®/Pectin 98:2) | | |
|---|---|---|
| 0.1N HCl | 0 | 0.00 |
| 0.1N HCl | 1 | 3.50 |
| 0.1N HCl | 2 | 10.11 |
| P-A Buffer 0.1% SDS pH = 7 | 3 | 15.97 |
| P-A Buffer 0.1% SDS pH = 7 | 4 | 24.28 |
| P-A Buffer pH = 7 | 6 | 42.54 |
| P-A Buffer pH = 7 | 12 | 66.43 |
| P-A Buffer pH = 7 | 16 | 70.74 |
| P-A Buffer pH = 7 | 18 | 70.94 |
| P-A Buffer pH = 7 | 20 | 70.57 |
| P-A Buffer pH = 7 | 24 | 67.05 |
| | GHOST | 15.41 |

Example 44

The mini-beads of Example 17 were coated with a combination of SURELEASE® and Pectin in a ratio of 99/1 (pectin content decreased over Example 43 from 2 to 1% in terms of solid weight ratio to SURELEASE®) for a total weight gain of 10% to give the following dissolution profile:

| (10% SURELEASE®/Pectin 99:1) | | |
|---|---|---|
| 0 h | 0.1N HCl | 0.00 |
| 1 h | 0.1N HCl | 8.31 |
| 2 h | 0.1N HCl | 9.59 |
| 3 h | P-A Buffer 0.1% SDS pH = 7 | 13.61 |
| 4 h | P-A Buffer 0.1% SDS pH = 7 | 30.04 |
| 6 h | P-A Buffer pH = 7 | 47.22 |
| 12 h | P-A Buffer pH = 7 | 65.31 |
| 16 h | P-A Buffer pH = 7 | 72.67 |
| 18 h | P-A Buffer pH = 7 | 70.50 |
| 20 h | P-A Buffer pH = 7 | 72.51 |
| 24 h | P-A Buffer pH = 7 | 76.71 |
| | Ghost | 2.79 |

Example 45

This Example is similar to Example 44 except that the weight gain was increased to 15%. This gave the following dissolution profile: (15% SURELEASE®/Pectin 99:1)

| (15% SURELEASE®/Pectin 99:1) | | |
|---|---|---|
| 0 h | 0.1N HCl | 0.00 |
| 1 h | 0.1N HCl | 0.00 |
| 2 h | 0.1N HCl | 0.00 |
| 3 h | P-A Buffer 0.1% SDS pH = 7 | 1.05 |
| 4 h | P-A Buffer 0.1% SDS pH = 7 | 4.72 |
| 6 h | P-A Buffer pH = 7 | 16.81 |
| 12 h | P-A Buffer pH = 7 | 17.71 |
| 16 h | P-A Buffer pH = 7 | 21.94 |
| 18 h | P-A Buffer pH = 7 | 25.25 |
| 20 h | P-A Buffer pH = 7 | 25.94 |
| 24 h | P-A Buffer pH = 7 | 55.11 |
| GHOST | | 10.31 |

The low amount of ghost sample suggested that the actual dissolution after 24 hours was higher than the 55% recorded, so the 0.1% SDS was maintained from $3^{rd}$ to $24^{th}$ hour to achieve the following profile:

| 0 h | 0.1N HCl | 0.00 |
|---|---|---|
| 1 h | 0.1N HCl | 0.00 |
| 2 h | 0.1N HCl | 0.00 |
| 3 h | P-A Buffer 0.1% SDS pH = 7 | 1.28 |
| 4 h | P-A Buffer 0.1% SDS pH = 7 | 5.91 |
| 6 h | P-A Buffer 0.1% SDS pH = 7 | 32.17 |
| 12 h | P-A Buffer 0.1% SDS pH = 7 | 64.87 |
| 16 h | P-A Buffer 0.1% SDS pH = 7 | 70.83 |
| 18 h | P-A Buffer 0.1% SDS pH = 7 | 77.71 |
| 20 h | P-A Buffer 0.1% SDS pH = 7 | 79.90 |
| 24 h | P-A Buffer 0.1% SDS pH = 7 | 89.18 |

Thus, in this Example, 89% of API was released after 24 hours, which is in accordance to the ghost results obtained.

Example 46

The beads of Example 18 were coated with 4.9% SURELEASE® to give the following dissolution profile:

| Time (hrs) | AV water | AV 0.15% SDS | AV 0.3% SDS |
|---|---|---|---|
| 1 | 0 | 0 | 10.195 |
| 3 | 3.765 | 1.74 | 29.425 |
| 4 | 4.535 | 4.675 | 41.12 |
| 6 | 7.99 | 10.745 | 55.875 |
| 8 | 10.98 | 6.895 | 69.2 |
| 12 | 16.69 | 17.095 | 82.535 |
| 16 | 22.715 | 18.235 | 85.97 |
| 20 | 26.54 | 9.7 | 87.87 |
| 24 | 29.395 | 21.325 | 87.69 |

Example 47 (a) and (b)

The beads of Example 19 were coated with Surelease at 2 different weight gains: 2.47% (Example 47a) and 4.89% (Example 47b); dissolution profiles are shown below:

| Dissolution (Example 47a) | | | |
|---|---|---|---|
| Time (hrs) | Water | 0.15% SDS | 0.3% SDS |
| 1 | 19.25 | 29.00 | 55.64 |
| 3 | 56.66 | 51.95 | 95.38 |
| 4 | 65.42 | 64.82 | 98.16 |
| 6 | 69.99 | 77.03 | 104.18 |
| 8 | 71.34 | 80.08 | 103.12 |
| 12 | 67.02 | 76.28 | 101.38 |
| 16 | 66.18 | 78.42 | 101.50 |
| 20 | 63.16 | 80.31 | 106.47 |
| 24 | 63.77 | 82.99 | 99.46 |

| Dissolution (Example 47b) | | | |
|---|---|---|---|
| Time (hrs) | Water | 0.15% SDS | 0.3% SDS |
| 1 | 0 | 0 | 0 |
| 3 | 0 | 0 | 31.14 |
| 4 | 4.33 | 12.78 | 46.06 |
| 6 | 18.43 | 21.08 | 56.89 |
| 8 | 27.61 | 31.89 | 65.52 |
| 12 | 39.49 | 43.13 | 75.88 |
| 16 | 46.38 | 51.44 | 82.56 |
| 20 | 51.91 | 57.23 | 87.39 |
| 24 | 55.86 | 59.78 | 91.45 |
| Ghost | 19.28% | 38.25% | |

Example 48

In the following example the oil phase and the aqueous phase are mixed in a proportion in the range 1:6-10, preferably approximately 1:7 or 1:8 with gentle continuous stirring of the components using a Magnetic Stirrer (manufactured by Stuart). The aqueous phase (gelatin with sorbitol) was prepared by adding the appropriate quantities of sorbitol (and SDS as surfactant) to water, heating to approximately 60-75° C. until in solution and then adding gelatin. The "gelatin solution" comprised 15-25% (preferably 17-18%) of gelatin; 75%-85% (preferably 77-82%) of water plus from 1-5% (preferably 1.5 to 3%) sorbitol. The gelatin solution was maintained at 60° C.-70° C. to maintain it in a fluid state. In a slightly variant method, the SDS was added to the aqueous phase at the same time the other components are added ie. gelatin and sorbitol at the beginning of the processing session. SDS (surfactant) was present in an amount between 0.8% and 1% (by weight) of the aqueous phase. The oil phase was made at room temperature with stirring until clear. The appropriate amount of CyA (see table below) was added to achieve the target proportion. Stirring was continued overnight. The emulsion was formed by addition of the oil phase to the heated aqueous phase with stirring as described above. The resultant emulsion then had the composition of the solidified mini-beads but with water still present. Once the emulsion was formed, the beading step was begun without delay by dropping the fluid emulsion into MCT (cooling fluid) maintained in the range 8-12° C. which effected solidification of the droplets. Beads were then collected in a mesh basket through which the oil was drained and the beads retained, excess oil removed by centrifugation then dried and washed with ethyl acetate then dried again. Drying was with the Freund Drum dryer with warm air at between 15° C. and 25° C. Uncoated mini-beads having the following composition were generated:

| | Mg/g |
|---|---|
| CYA | 80-120 |
| TRANSCUTOL® HP | 150-190 |
| CREMOPHOR® EL | 80-120 |
| Migyol 810 | 20-60 |
| SDS | 15-50 |
| D-Sorbitol | 30-80 |
| Gelatin | 450-550 |

Example 49

The beads of this Example were produced initially as for Example 48 then through ejection of the fluid o/w emulsion through a vibrating 3 mm diameter single lumen nozzle applied to the Freund Spherex machine. Operation of the Spherex machine manufactured by Freund was in accordance with the manufacturer's instructions. The lines to the orifice/nozzle were maintained at 65-85° C. to maintain the fluidity of the solution. Use of the Spherex machine achieved high monodispersity—out of a 100 g batch, 97 g of mini-spheres were between 1.4 to 2 mm diameter. Larger and smaller beads were rejected by passing the batch first through a 2 mm mesh and subsequently through a 1.4 mm mesh. The resulting beads had the following composition:

| Components | Lower limit (mg/g) | Upper limit (mg/g) |
|---|---|---|
| CyA | 80 | 140 |
| Gelatin | 490 | 610 |
| D-Sorbitol | 55 | 75 |
| SDS | 20 | 40 |
| TRANSCUTOL® P | 100 | 180 |
| Cremophor EL | 50 | 110 |
| MCT oil* | 45 | 180 |
| LABRAFIL® M 1944 CS | 40 | 150 |
| Epax 6000** | 80 | 150 |

*MCT brands used include: Mygliol 810, LABRAFAC® Lipophile 1349 WL, Captex 355, etc . . .
**Omega-3 oil having a EPA (eicosapentanoic acid)/DHA (docosohexaenoic acid) ratio ~1.5

Example 50

Uncoated beads in this Example were made in accordance with Example 48 except that the active ingredient was tacrolimus instead of CyA and the other components were as stated in the table below.

| Components | Lower limit (mg/g) | Upper limit (mg/g) |
|---|---|---|
| Tacrolimus | 11 | 17 |
| Gelatin | 470 | 510 |
| D-Sorbitol | 63 | 70 |
| SDS | 22 | 42 |
| TRANSCUTOL® P | 104 | 119 |
| TWEEN® 80 | 106 | 146 |
| HPMC E 100 | 27 | 30 |
| LABRAFIL® M 1944 CS | 140 | 203 |
| Ascorbic Acid | 47 | 48 |

Vaccine Examples

The following three examples illustrate formulations according to the invention which are made by following the process described in Example 48 but using the ingredients (eg using ovalbumin instead of CyA as main active principle) and quantities mentioned in the tables below.

Example 51

| Composition | mg/g |
|---|---|
| Ovalbumin | 6-10 |
| alphaGalCer | 0.1-0.5 |
| Montanide ISA 720 | 70-120 |
| LABRAFIL® M 1944 CS | 280-320 |
| SPAN® 85 | 1-5 |
| TWEEN® 80 | 1-5 |
| Gelatin | 450-550 |
| D-Sorbitol | 50-80 |
| NaOH | 1-10 |
| HPMCP | 30-80 |

The aqueous phase was composed of gelatin, D-sorbitol, ovalbumin, alphaGalCer, HPMCP and NaOH. The other components, MONTANIDE® ISA 720, LABRAFIL®® M 1944 CS, TWEEN® 80 and S [am SPAN® 85) constituted the oil phase.

HPMCP (hydroxy-propyl-methyl-cellulose-phtalate or hypromellose phthalate) was used to prevent release in the gastric environment, since it is a polymer soluble above pH 5.5 The ratio used between oil phase and aqueous phase was 1:7.

Example 52

| Composition | mg/g |
|---|---|
| rCTB | 1-5 |
| alphaGalCer | 1-5 |
| Montanide ISA 720 | 80-120 |
| LABRAFIL® M 1944 CS | 250-300 |
| SPAN® 85 | 10-20 |
| TWEEN® 80 | 25-35 |
| Gelatin | 450-550 |
| D-Sorbitol | 30-60 |
| NaOH | 5-10 |
| HPMCP | 30-60 | rCTB is the recombinant subunit B of Cholera Toxin (it replaces Ovalbumin of Example 51). Composition of aqueous and oil phase are the same of Example 1, the only difference being the addition of part of TWEEN® 80 to the aqueous phase.

Example 53

| Composition | mg/g |
|---|---|
| rCTB | 1-5 |
| alphaGalCer | 1-5 |
| Montanide ISA 720 | 60-100 |
| LABRAFIL® M 1944 CS | 200-260 |
| SPAN® 85 | 5-20 |
| TWEEN® 80 | 20-50 |

-continued

| Composition | mg/g |
|---|---|
| Gelatin | 500-600 |
| D-Sorbitol | 50-70 |

In this Example, neither HPMCP nor NaOH was used in the aqueous phase. The beads prepared were then coated with 5.5% of L 30-D 55, an Evonik polymer soluble above pH 5.5. Also in this example (as per Ex. 52) Tween 80 was dissolved partially in the aqueous phase. The ratio employed between the 2 phases was increased to 1:9.
Further Tacrolimus Formulations.

Example 54

The following three examples illustrate formulations according to the invention which are made by following the process described in Example 48 but using the quantities of ingredients mentioned in the tables below and using tacrolimus instead of CyA. However, the oil phase (SOLUTOL®) was warmed to 40-50° C. before adding and dissolving the tacrolimus and the BHT therein.

| Composition | mg/g |
|---|---|
| Tacrolimus | 21.21 |
| SOLUTOL® HS 15 | 402.62 |
| BHT | 0.15 |
| Gelatin | 517.08 |
| D-Sorbitol | 58.95 |

SOLUTOL® HS 15 is Polyethylene glycol 660 12-hydroxystearate in which the polyglycol ester of 12-hydroxystearic acid makes up 70% of the SOLUTOL® and is the hydrophobic component and in which the polyethylene glycol makes up 30% of the SOLUTOL® and is the hydrophilic component. BHT is butyl hydroxy toluene, a hydrophobic antioxidant.
Mean dissolution of 3 runs was as follows:

| | Time/h | | | | | |
|---|---|---|---|---|---|---|
| | 1 | 2 | 3 | 4 | 5 | 6 |
| Mean | 115.93 | 118.27 | 121.38 | 122.25 | 123.23 | 119.96 |

| Dissolution Method: | |
|---|---|
| Apparatus | USP Type II (Paddles) |
| Media | Na3PO4 pH 6.8 |
| RPM | 75 |
| Temperature | 37' C. |

Example 55

This example was made by following the process of Example 55 but using the proportions of materials indicated in the table below.

| Composition | mg/g |
|---|---|
| Tacrolimus | 20.54 |
| SOLUTOL® HS 15 | 390.02 |
| BHT | 0.14 |
| Gelatin | 493.05 |
| D-Sorbitol | 56.26 |
| SDS | 39.98 |

With the addition of SDS in the gelatin phase, the emulsion resulting by mixing the oil phase and gelatin phase was transparent (microemulsion -) as were the beads subsequently produced (solidified microemulsion).

Example 56

This example was made by following the process described in Example 48 but using the quantities of ingredients mentioned in the table below and using tacrolimus instead of CyA.

| Composition | mg/g |
|---|---|
| Tacrolimus | 21.68 |
| TRANSCUTOL® | 188.66 |
| BHT | 0.12 |
| Gelatin | 452.86 |
| D-Sorbitol | 51.57 |
| EUDRAGIT® EPO | 128.66 |
| CREMOPHOR® EL | 104.96 |
| MIGLYOL® 810 N | 51.5 |

EUDRAGIT® EPO is a polymer soluble in acidic media. It was added to the aqueous phase (gelatin and sorbitol) during preparation as a solution in acetate buffer (approximately pH3.5).

| | Time/h | | | | | |
|---|---|---|---|---|---|---|
| | 1 | 2 | 3 | 4 | 5 | 6 |
| Mean | 90.68209 | 102.841 | 104.3954 | 101.6017 | 100.8962 | 103.3445 |

| Dissolution Method: | |
| --- | --- |
| Apparatus | USP Type II (Paddles) |
| Media | 0.2M Na3PO4 pH 6.8 |
| RPM | 75 |
| Temperature | 37' C. |

Lacticin Formulations.

Example 57

The method of preparation was as for Example 54 except for the change in active ingredient and that SDS was substituted for BHT. The amounts used were as shown in the following table:

| Composition | mg/g |
| --- | --- |
| Lacticin | 35.93 |
| SOLUTOL® HS 15 | 332.17 |
| SDS | 42.91 |
| Gelatin | 529.42 |
| D-Sorbitol | 59.57 |

Example 58

This is the same as example 57 except that the beads were coated with a SURELEASE®/pectin mixture (98:2 ratio by weight) as described in Example 17. The weight gain was 11.8%.

Example 59

This example is similar to that of Example 15 the only difference being the increased SDS content. In this run, more than 90% of beads were in the range 1.4-2.0 mm. The composition and release profile were as follows:

| | |
| --- | --- |
| Lacticin | 40.01 |
| MIGLYOL®810 | 55.69 |
| CREMOPHOR® EL | 109.01 |
| SDS | 40.41 |
| Gelatin | 498.62 |
| TRANSCUTOL® HP | 200.15 |
| D-Sorbitol | 56.10 |

Example 60

This is the same as example 59 except that the beads were coated with a SURELEASE®/pectin mixture (98:2 ratio by weight) as described in Example 17. The weight gain was 7%.
Two Water-Soluble Polymers Form the Matrix.

Example 61

| Composition | mg/g |
| --- | --- |
| Cyclosporin A | 179 |
| TRANSCUTOL® P | 272 |
| CREMOPHOR® EL | 152 |
| MIGLYOL® 810 | 76.5 |
| Agar | 178 |
| Gelatin | 142 |

This formulation was made in the same way as were Examples 1 to 13. The agar was first dissolved in water heated to about 90 deg C. Once the solution becomes clear the temperature was reduced to around 70 deg C. and gelatin is added. In the meanwhile the oil phase was made by mixing all the components together (CyA, TRANSCUTOL®, CREMOPHOR® and mygliol). The two phases were mixed together in a ratio of 1:10 (oil:aqueous phases). The gelatin/agar mixture of this Example yielded a stronger bead than agar alone. Also the mixture allowed for a reduction of the total amount of gelling polymers present from around 500 mg/g to 320 mg/g (=178+142). This also allowed higher incorporation of Cyclosporin A (from around 100 mg/g to 179 mg/g).

Void/Dead Space Filled with Fluids

Example 62

| Uncoated bead formulation (A): | |
| --- | --- |
| Composition | mg/g |
| Cyclosporin A | 109 |
| TRANSCUTOL® P | 165 |
| CREMOPHOR® EL | 93 |
| MIGLYOL® 810 | 46 |
| Sorbitol | 56 |
| SDS | 40 |
| Gelatin | 490 |

The above beads (formulation A—uncoated) were made by the process used for Examples 14-17. Using the Diosna machine, these beads were then coated with 4.6% (B), 7.4% (C) and 15.0% (D) weight gain of SURELEASE® and Pectin at the ratio of 98:2 in the manner described in Examples 14-17. Hard gelatin capsules then filled with a liquid media combined with each of the above uncoated and coated beads, as per the table below.

| Liquid Media | Beads | | | |
| --- | --- | --- | --- | --- |
| NEORAL® | A | B | C | D |
| SPAN 85® | A | B | C | D |
| Corn oil | A | B | C | D |
| LABRAFAC® | A | B | C | D |
| TRANSCUTOL® P | A | B | C | D |
| TWEEN® 80 | A | B | C | D |

| Dissolution Experiments | | | |
| --- | --- | --- | --- |
| SPAN® 85 Time(H) | Replicate1 (%) | Replicate2(%) | Mean |
| 1 | 0 | 0 | 0 |
| 2 | 0 | 0 | 0 |
| 3 | 4.1 | 0 | 2.05 |
| 4 | 18.3 | 27.6 | 22.95 |
| 6 | 47.8 | 67 | 57.4 |
| 12 | 69.1 | 85.4 | 77.25 |
| 16 | 74.3 | 88.4 | 81.35 |
| 18 | 76.5 | 91.9 | 84.2 |
| 20 | 77.7 | 87.3 | 82.5 |
| 24 | 79.9 | 92.7 | 86.3 |

-continued

Dissolution Experiments

| Corn Oil Time(H) | Replicate1 (%) | Replicate2(%) | Mean |
|---|---|---|---|
| 1 | 1 | 7.8 | 4.4 |
| 2 | 0 | 16.5 | 8.25 |
| 3 | 16.8 | 49.4 | 33.1 |
| 4 | 29.2 | 61.7 | 45.45 |
| 6 | 63 | 73.3 | 68.15 |
| 12 | 69.6 | 83.6 | 76.6 |
| 16 | 73.5 | 85.8 | 79.65 |
| 18 | 75.3 | 86.6 | 80.95 |
| 20 | 77.2 | 70 | 73.6 |
| 24 | 79.4 | 88.4 | 83.9 |

| LABRAFAC® Time(H) | Replicate1 (%) | Replicate2(%) | Mean |
|---|---|---|---|
| 1 | 0 | 0 | 0 |
| 2 | 0 | 6.7 | 3.35 |
| 3 | 13.9 | 34.4 | 24.15 |
| 4 | 32.4 | 58.1 | 45.25 |
| 6 | 56.7 | 72.1 | 64.4 |
| 12 | 69.2 | 83.1 | 76.15 |
| 16 | 72.4 | 85.6 | 79 |
| 18 | 74.9 | 86.9 | 80.9 |
| 20 | 75.8 | 82.6 | 79.2 |
| 24 | 79.1 | 89.7 | 84.4 |

| TRANSCUTOL® Time(H) | Replicate1 (%) | Replicate2(%) | Mean |
|---|---|---|---|
| 1 | 0 | 12 | 6 |
| 2 | 13.1 | 15.7 | 14.4 |
| 3 | 12.7 | 26.7 | 19.7 |
| 4 | 17.7 | 28.2 | 22.95 |
| 6 | 24.7 | 30 | 27.35 |
| 12 | 24.3 | 35.7 | 30 |
| 16 | 27.8 | 40.9 | 34.35 |
| 18 | 32.9 | 43.9 | 38.4 |
| 20 | 32 | 45.6 | 38.8 |
| 24 | 37.5 | 51.2 | 44.35 |

| TWEEN® Time(H) | Replicate1 (%) | Replicate2 | Mean |
|---|---|---|---|
| 1 | 1.5 | 23.21 | 12.355 |
| 2 | 3.6 | 34.01 | 18.805 |
| 3 | 26.3 | 62.7 | 44.5 |
| 4 | 55.7 | 69.3 | 62.5 |
| 6 | 62.8 | 77.9 | 70.35 |
| 12 | 77.1 | 90.6 | 83.85 |
| 16 | 80.7 | 91.3 | 86 |
| 18 | 81.2 | 92 | 86.6 |
| 20 | 83.3 | 92.7 | 88 |
| 24 | 83.4 | 93.51 | 88.455 |

Formulations Comprising Salmon Calcitonin (sCT)

Example 63 sCT was added to the gelatin solution and it was mixed at 60° C. over night by following the process used previously.

| Components | mg | mg/g | % |
|---|---|---|---|
| Salmon Calcitonin | 18.70 | 4.05 | 0.41 |
| TRANSCUTOL® HP | 1068.78 | 231.64 | 23.16 |
| CREMOPHOR® EL | 462.56 | 100.25 | 10.03 |
| MIGLYOL® 810 | 342.36 | 74.20 | 7.42 |
| SDS | 182.90 | 39.64 | 3.96 |
| D-Sorbitol | 272.80 | 59.13 | 5.91 |
| Gelatin | 2265.80 | 491.08 | 49.11 |
| Total | 4613.90 | 1000.00 | 100.00 |

Example 64

A solution of sCT in water was added to the emulsion and it was mixed at 60° C. for ~5 min otherwise following the process of Example 54.

| Components | mg | mg/g | % |
|---|---|---|---|
| Salmon Calcitonin | 9.40 | 4.08 | 0.41 |
| TRANSCUTOL® HP | 533.96 | 231.79 | 23.18 |
| CREMOPHOR® EL | 229.32 | 99.55 | 9.95 |
| MIGLYOL® 810 | 172.22 | 74.76 | 7.48 |
| SDS | 65.70 | 28.52 | 2.85 |
| D-Sorbitol | 125.60 | 54.52 | 5.45 |
| Gelatin | 1167.40 | 506.77 | 50.68 |
| Total | 2303.60 | 1000.00 | 100.00 |

Example 65

A solution of sCT in water was added to the emulsion and it was mixed at 60° C. for ~5 min. otherwise following the process of Example 54. This Example is like Example 65 except that citric acid was used.

| Components | mg | mg/g | % |
|---|---|---|---|
| Salmon Calcitonin | 9.40 | 3.92 | 0.39 |
| TRANSCUTOL® HP | 535.69 | 223.23 | 22.32 |
| CREMOPHOR® EL | 234.71 | 97.81 | 9.78 |
| MIGLYOL® 810 | 173.89 | 72.47 | 7.25 |
| SDS | 69.90 | 29.13 | 2.91 |
| D-Sorbitol | 119.00 | 49.59 | 4.96 |
| Citric Acid | 120.00 | 50.01 | 5.00 |
| Gelatin | 1137.10 | 473.85 | 47.39 |
| Total | 2399.70 | 1000.00 | 100.00 |

Example 66 sCT was added to the oil phase and it was mixed with the gelatin solution at 60° C. for ~5 min. otherwise following the process of Example 54.

| Components | mg | mg/g | % |
|---|---|---|---|
| sCT | 13.00 | 4.17 | 0.42 |
| TRANSCUTOL® HP | 632.60 | 202.88 | 20.29 |
| CREMOPHOR® EL | 320.90 | 102.92 | 10.29 |
| MIGLYOL® 810 | 221.50 | 71.04 | 7.10 |
| SDS | 86.25 | 27.66 | 2.77 |
| D-Sorbitol | 130.25 | 41.77 | 4.18 |
| Citric Acid | 156.70 | 50.26 | 5.03 |
| Gelatin | 1556.83 | 499.30 | 49.93 |
| Total | 3118.03 | 1000.00 | 100.00 |

Example 67

This formulation was prepared as for previous sCT formulations.

| Dried Beads | mg | mg/g | % |
|---|---|---|---|
| Salmon Calcitonin | 9.63 | 4.18 | 0.42 |
| TRANSCUTOL® HP | 542.18 | 235.28 | 23.53 |
| CREMOPHOR® EL | 238.64 | 103.56 | 10.36 |
| MIGLYOL® 810 | 175.68 | 76.24 | 7.62 |
| SDS | 64.70 | 28.08 | 2.81 |
| D-Sorbitol | 114.70 | 49.77 | 4.98 |
| Gelatin | 1158.90 | 502.90 | 50.29 |
| Total | 2304.43 | 1000.00 | 100.00 |

Example 68

This formulation was prepared as for previous sCT formulations.

| Dried Beads | mg | mg/g | % |
|---|---|---|---|
| Salmon Calcitonin | 9.55 | 3.71 | 0.37 |
| TRANSCUTOL® HP | 555.29 | 215.60 | 21.56 |
| CREMOPHOR® EL | 237.85 | 92.35 | 9.23 |
| MIGLYOL® 810 | 180.96 | 70.26 | 7.03 |
| SDS | 71.00 | 27.57 | 2.76 |
| D-Sorbitol | 115.60 | 44.88 | 4.49 |
| Citric Acid | 120.00 | 46.59 | 4.66 |
| Gelatin | 1285.30 | 499.04 | 49.90 |
| Total | 2575.55 | 1000.00 | 100.00 |

Example 69

This formulation was prepared as for previous sCT formulations.

| Dried Beads | mg | mg/g | % |
|---|---|---|---|
| Salmon Calcitonin | 9.55 | 3.76 | 0.38 |
| TRANSCUTOL® HP | 556.72 | 219.42 | 21.94 |
| CREMOPHOR® EL | 238.46 | 93.98 | 9.40 |
| MIGLYOL® 810 | 181.42 | 71.50 | 7.15 |
| SDS | 76.90 | 30.31 | 3.03 |
| D-Sorbitol | 130.70 | 51.51 | 5.15 |
| NaTDC | 120.00 | 47.30 | 4.73 |
| Gelatin | 1223.50 | 482.21 | 48.22 |
| Total | 2537.25 | 1000.00 | 100.00 |

Example 70

This formulation was prepared as for previous sCT formulations.

| Dried Beads | mg | mg/g | % |
|---|---|---|---|
| Salmon Calcitonin | 9.55 | 3.98 | 0.40 |
| TRANSCUTOL® HP | 542.13 | 226.03 | 22.60 |
| CREMOPHOR® EL | 232.21 | 96.82 | 9.68 |
| MIGLYOL® 810 | 176.67 | 73.66 | 7.37 |
| SDS | 80.80 | 33.69 | 3.37 |
| D-Sorbitol | 118.90 | 49.57 | 4.96 |
| C10 | 120.00 | 50.03 | 5.00 |
| Gelatin | 1118.20 | 466.22 | 46.62 |
| Total | 2398.45 | 1000.00 | 100.00 |

Example 70

This formulation was prepared as for previous sCT formulations.

| Dried Beads | mg | mg/g | % |
|---|---|---|---|
| Salmon Calcitonin | 9.75 | 4.07 | 0.41 |
| TRANSCUTOL® HP | 541.45 | 225.78 | 22.58 |
| CREMOPHOR® EL | 232.61 | 97.00 | 9.70 |
| MIGLYOL® 810 | 175.64 | 73.24 | 7.32 |
| SDS | 71.30 | 29.73 | 2.97 |
| D-Sorbitol | 116.80 | 48.70 | 4.87 |
| Plantacare 818 | 130.90 | 54.58 | 5.46 |
| Gelatin | 1119.70 | 466.90 | 46.69 |
| Total | 2398.15 | 1000.00 | 100.00 |

Example 71

Tacrolimus beads were made containing 2.5% tacrolimus dry weight and then coated with ibuprofen by drug layering using the Vector CF 360 EX granulator following the method described in the body of the specification above. Materials were used in amounts sufficient to obtain the final weights given in the table below. The ibuprofen was first mixed with PVP (a binder) in the appropriate ratio before layering was conducted (duration: less than 1 hour). The ibuprofen-layered tacrolimus beads were then coated in the manner described in previous examples with a mixture of ethylcellulose (EC 10) and a plasticiser, dibutyl sebacate (DBS) over approximately 2 hours in the appropriate ratio.

| Dried Beads | g | % |
|---|---|---|
| Tacrolimus bead | 800 | 62.39 |
| Ibuprofen | 200 | 15.60 |
| PVP K-32 | 9.4 | 0.73 |
| DBS | 24.8 | 1.93 |
| EC 10 | 248 | 19.34 |
| Total | 1282.2 | 100.00 |

The coated beads were tested by standard USP dissolution methods and had the following release profile:

Example 72

This is the same as example 71 except that the ibuprofen-layered tacrolimus beads were coated in the manner described in previous examples with 10%, 15% and 20% total weight gain of a mixture of EUDRAGIT®RL-30D, talc (as glidant) and DBS (Examples 72a, 72b and 72c respectively).

Example 72b

20% RL-30D

| Dried Beads | g | % |
|---|---|---|
| Tacrolimus bead | 920 | 56.53 |
| Ibuprofen | 230 | 14.13 |
| PVP K-32 | 11.7 | 0.72 |
| DBS | 30.8 | 1.89 |
| RL-30D | 308 | 18.92 |
| Talc | 127 | 7.80 |
| Total | 1627.5 | 100.00 |

Examples 72a and 72c were similar (same weight ratios between ingredients) except for the different amounts of RL-30D.

The release profile of the coated beads were tested by standard USP dissolution methods. Tests for ibuprofen and tacrolimus were run on separate samples of beads. Ibuprofen was tested in acid media only (24 h). Tacrolimus was tested firstly 2 hour acid & 22 hour buffer ph 6.8 (24 hours total). The USP Type II (Paddles) apparatus was used at 75 RPM and a temperature of 37'C. Media was 0.1N HCL except that for tacrolimus, after 2 hours in acid media, 0.2M Na3PO4 pH 6.8 was added.

Release profile of Example 72a (10% RL-30D)

| Time/ | % Dissolved | |
|---|---|---|
| h | Tacrolimus | Ibuprofen |
| 1 |  | 7.68 |
| 2 | 40.57 | 14.88 |
| 3 |  | 32.62 |
| 4 | 66.36 | 53.6 |
| 5 |  | 67.15 |
| 6 | 94.95 | 75.45 |
| 8 |  | 82.2 |
| 12 | 90.85 | 86.29 |
| 24 | 80.79 | 85.39 |

Release profile of Example 72b (15% RL-30D)

| Time/ | % Dissolved | |
|---|---|---|
| h | Tacrolimus | Ibuprofen |
| 1 |  | 6.76 |
| 2 | 24.82 | 11.27 |
| 3 |  | 26.03 |
| 4 | 54.51 | 48.92 |
| 5 |  | 60.81 |
| 6 | 83.62 | 69.29 |
| 8 |  | 77.69 |
| 12 | 81.17 | 81.83 |
| 24 | 76.88 | 81.72 |

Release profile of Example 72c (20% RL-30D)

| Time/ | % Dissolved | |
|---|---|---|
| h | Tacrolimus | Ibuprofen |
| 1 |  | 0.36 |
| 2 | 24.69 | 6.72 |
| 3 |  | 19.56 |
| 4 | 52.6 | 36.59 |
| 5 |  | 47.98 |
| 6 | 75.51 | 55.15 |
| 8 |  | 63.61 |
| 12 | 71.29 | 71.17 |
| 24 | 76.02 | 73.1 |

Example 73

This is the same as Example 72 except that the tacrolimus beads were first layered in the manner described in previous examples with ibuprofen and subsequently coated with theophylline by spray drying. The resulting ibuprofen-plus-theophylline-layered tacrolimus beads were then coated, as in Example 72, but with EUDRAGIT®L-30D to provide an enteric coat. The L-30D was first mixed with talc (as glidant), TEC (triethyl citrate) and HPMC E5 (Methocel).

| Dried Beads | g | % |
|---|---|---|
| Tacrolimus bead | 920 | 47.21 |
| Ibuprofen | 230 | 11.80 |
| Theopylline | 100 | 5.13 |
| PVP K-32 | 11.7 | 0.60 |
| TEC | 29 | 1.49 |
| RL-30D | 288 | 14.78 |
| HPMC E5 | 20 | 1.03 |
| Talc | 350 | 17.96 |
| Total | 1948.7 | 100.00 |

Release profile of Example 73 determined, in relation to tacrolimus and ibuprofen, as for Example 72.

| | Tacrolimus | Ibuprofen |
|---|---|---|
| 1 |  | 2.73 |
| 2 | 0.55 | 5.58 |
| 3 |  | 6.72 |
| 4 | 0 | 7.66 |
| 5 |  | 8.6 |
| 6 | 0 | 9.48 |
| 8 |  | 11.26 |
| 12 | 0 | 14.95 |
| 24 | 0 | 27.39 |

The invention claimed is:

1. A dried oil-in-water emulsion composition comprising a water-soluble polymer matrix material in which are dispersed droplets of an oil phase wherein the oil phase comprises 2-(2 ethoxyethoxy)ethanol, polyethoxylated castor oil and caprylic/capric triglyceride;

the water-soluble polymer matrix material comprises gelatin, sodium dodecyl sulphate and D-sorbitol;

the composition further comprising cyclosporin A in at least the oil phase;

and wherein
the composition comprises:
cyclosporin A in an amount of 8.0 to 12.0%;
2-(2-ethoxyethoxy)ethanol at 99.9% purity in an amount of 15.0 to 19.0%;
polyethoxylated castor oil in an amount of 8.0 to 12.0%;
caprylic/capric triglyceride in an amount of 2.0 to 6.0%;
sodium dodecyl sulphate in an amount from 1.0 to 4.5%;
D-sorbitol in an amount of 3.0 to 8.0%; and
gelatin in an amount of 45.0 to 55.0%;
wherein the % are % by weight as a proportion of the dry weight of the composition.

2. The composition according to claim 1 comprising:
cyclosporin A in an amount of about 10.9%;
2-(2-ethoxyethoxy)ethanol at 99.9% purity in an amount of about 16.5%;
polyethoxylated castor oil in an amount of about 9.3%;
caprylic/capric triglyceride in an amount of about 4.6%;
sodium dodecyl sulphate in an amount of about 4.0%;
D-sorbitol in an amount of about 5.6%;
and gelatin in an amount of about 49.0%.
wherein the % are % by weight as a proportion of the dry weight of the composition.

3. The composition according to claim 1 in the form of a mini-bead.

4. The composition according to claim 1 in the form of a mini-bead wherein the mini-bead has a diameter of from 0.5 mm to 5 mm.

5. The composition according to claim 1 in the form of a mini-bead wherein the mini-bead has a coat comprising one or more polymers.

6. The composition according to claim 5 wherein the coat comprises a pH-independent polymer.

7. The composition according to claim 5 wherein the coat comprises ethylcellulose.

8. The composition according to claim 5 wherein the coat comprises ethylcellulose and a plasticizer.

9. The composition according to claim 5 wherein the coat comprises a pH-independent polymer and a polysaccharide susceptible of degradation by a bacterial enzyme normally found in the colon.

10. The composition according to claim 5 wherein the coat comprises ethylcellulose and pectin.

11. The composition according to claim 5 wherein the coat comprises a first coat and a second coat, wherein said the second coat is outside the first coat, and wherein:
   (i) the first coat comprises a cellulosic film-forming polymer;
   (ii) and the second coat comprises a pH-independent polymer and a polysaccharide susceptible of degradation by a bacterial enzyme normally found in the colon.

12. The composition according to claim 5 wherein the coat comprises a first coat and a second coat, wherein the second coat is outside the first coat, and wherein:
   (i) the first coat comprises a cellulosic film-forming polymer selected from hyproxypropyl methyl cellulose and hydroxypropyl cellulose;
   (ii) and the second coat comprises ethyl cellulose and pectin.

13. The composition according to claim 1 in the form of a plurality of mini-beads contained in a hard gel capsule, wherein the mini-beads bear a coat comprising a pH-independent polymer.

14. The composition according to claim 2 in the form of a mini-bead.

15. The composition according to claim 2 in the form of a mini-bead wherein the mini-bead has a diameter of from 0.5 mm to 5 mm.

16. The composition according to claim 2 in the form of a mini-bead wherein the mini-bead has a coat comprising one or more polymers.

17. The composition according to claim 2 in the form of a plurality of mini-beads contained in a hard gel capsule, wherein the mini-beads bear a coat comprising a pH-independent polymer.

18. The composition according to claim 1 wherein cyclosporine A is dissolved in the oil phase.

* * * * *